(12) United States Patent
Rhead et al.

(10) Patent No.: US 10,564,116 B2
(45) Date of Patent: Feb. 18, 2020

(54) OPTICAL IMAGE CAPTURE WITH POSITION REGISTRATION AND RF IN-WALL COMPOSITE IMAGE

(71) Applicant: Fluke Corporation, Everett, WA (US)

(72) Inventors: Jamie Rhead, Plymouth, MN (US); Paul H. Heydron, Everett, WA (US); Christopher D. Corrigan, Seattle, WA (US); Brian Knight, Lake Stevens, WA (US); Nikola Mrvaljevic, Mountlake Terrace, WA (US); Luis R. Silva, Lynnwood, WA (US); Matthew F. Schmidt, River Falls, WI (US)

(73) Assignee: Fluke Corporation, Everett, WA (US)

( * ) Notice: Subject to any disclaimer, the term of this patent is extended or adjusted under 35 U.S.C. 154(b) by 313 days.

(21) Appl. No.: 15/141,102

(22) Filed: Apr. 28, 2016

(65) Prior Publication Data
US 2017/0315073 A1 Nov. 2, 2017

(51) Int. Cl.
*G01N 27/02* (2006.01)
*G01B 7/14* (2006.01)
*G01V 3/08* (2006.01)

(52) U.S. Cl.
CPC ............... *G01N 27/02* (2013.01); *G01B 7/14* (2013.01); *G01V 3/08* (2013.01)

(58) Field of Classification Search
CPC .................................................... G01N 27/02
See application file for complete search history.

(56) References Cited

U.S. PATENT DOCUMENTS 4,464,622 A 8/1984 Franklin
5,384,543 A 1/1995 Bible et al.
(Continued)

FOREIGN PATENT DOCUMENTS

DE 10 2005 052 367 A1 5/2007
EP 2 720 065 A1 4/2014
(Continued)

OTHER PUBLICATIONS

International Search Report and Written Opinion, dated Nov. 3, 2017, for International Application No. PCT/US2017/029581, 8 pages.
(Continued)

*Primary Examiner* — Huy Q Phan
*Assistant Examiner* — Adam S Clarke
(74) *Attorney, Agent, or Firm* — Seed IP Law Group LLP

(57) ABSTRACT

A radio frequency (RF) imaging device comprises a position sensor, an RF sensor assembly, an optical sensor, a processor, and a memory. The position sensor determines a position of the RF imaging device relative to a surface. The RF sensor assembly captures RF image data representing an RF image of a portion of a space behind the surface at the determined position. The optical sensor captures optical image data representing an optical image of the surface at the determined position. The processor produces a composite image in which at least one or more portions of the RF image and one or more portions of the optical image that correspond to the same position relative to the surface are simultaneously viewable. The RF image data and the optical image data are stored in the memory in association with position data derived from the determined position of the RF imaging device.

22 Claims, 28 Drawing Sheets

(56) References Cited

U.S. PATENT DOCUMENTS

| | | | |
|---|---|---|---|
| 5,457,394 A | 10/1995 | McEwan | |
| 5,519,400 A | 5/1996 | McEwan | |
| 5,541,605 A | 7/1996 | Heger | |
| 5,557,277 A | 9/1996 | Tricoles et al. | |
| 5,592,170 A | 1/1997 | Price et al. | |
| 5,704,142 A | 1/1998 | Stump | |
| 5,796,363 A | 8/1998 | Mast | |
| 5,835,054 A | 11/1998 | Warhus et al. | |
| 6,211,662 B1 | 4/2001 | Bijawat et al. | |
| 6,351,659 B1* | 2/2002 | Vilsmeier | A61B 6/12 600/407 |
| 6,417,797 B1 | 7/2002 | Cousins et al. | |
| 6,490,471 B2 | 12/2002 | Svenson et al. | |
| 6,670,906 B1 | 12/2003 | Roberts et al. | |
| 6,885,191 B1 | 4/2005 | Gleman | |
| 7,208,932 B1 | 4/2007 | Chun | |
| 7,236,120 B2 | 6/2007 | Healy et al. | |
| 7,454,242 B2 | 11/2008 | Fear et al. | |
| 7,474,256 B2 | 1/2009 | Ohta et al. | |
| 7,482,968 B2 | 1/2009 | Wuersch et al. | |
| 7,626,400 B2 | 12/2009 | Holbrook et al. | |
| 7,660,452 B2 | 2/2010 | Zwirn et al. | |
| 8,077,072 B2 | 12/2011 | Mohamadi et al. | |
| 8,095,204 B2 | 1/2012 | Smith et al. | |
| 8,253,619 B2 | 8/2012 | Holbrook et al. | |
| 8,284,027 B2 | 10/2012 | Taki et al. | |
| 8,451,162 B2 | 5/2013 | Holbrook et al. | |
| 8,494,615 B2 | 7/2013 | Melamed et al. | |
| 8,593,329 B2 | 11/2013 | Mohamadi et al. | |
| 8,686,891 B2 | 4/2014 | Krapf et al. | |
| 8,731,333 B2 | 5/2014 | Sieracki | |
| 8,981,781 B2 | 3/2015 | Haldner et al. | |
| 9,063,232 B2 | 6/2015 | McNeill et al. | |
| 9,194,950 B2 | 11/2015 | Watts et al. | |
| 9,664,808 B2 | 5/2017 | Nguyen et al. | |
| 9,784,557 B2 | 10/2017 | Sgarz et al. | |
| 9,797,756 B2 | 10/2017 | Silva et al. | |
| 10,254,398 B2* | 4/2019 | Ghazanfarpour | G01S 7/20 |
| 2002/0016541 A1* | 2/2002 | Glossop | A61B 90/10 600/407 |
| 2002/0130806 A1 | 9/2002 | Taylor, Jr. et al. | |
| 2004/0077943 A1 | 4/2004 | Meaney et al. | |
| 2004/0232329 A1 | 11/2004 | Biggs | |
| 2004/0263535 A1* | 12/2004 | Birkenbach | A61B 6/032 345/629 |
| 2005/0054910 A1* | 3/2005 | Tremblay | A61B 5/055 600/411 |
| 2005/0156776 A1 | 7/2005 | Waite | |
| 2006/0006995 A1 | 1/2006 | Tabankin et al. | |
| 2006/0055584 A1 | 3/2006 | Waite et al. | |
| 2006/0152404 A1 | 7/2006 | Fullerton et al. | |
| 2006/0170584 A1 | 8/2006 | Romero et al. | |
| 2006/0183995 A1 | 8/2006 | Bond et al. | |
| 2007/0035436 A1* | 2/2007 | Thompson | G01S 7/22 342/22 |
| 2007/0084675 A1 | 4/2007 | Kang et al. | |
| 2008/0077015 A1 | 3/2008 | Boric-Lubecke et al. | |
| 2008/0111732 A1 | 5/2008 | Bublitz et al. | |
| 2008/0143581 A1 | 6/2008 | Kreiner et al. | |
| 2008/0204322 A1 | 8/2008 | Oswald et al. | |
| 2008/0231525 A1 | 9/2008 | Krapf et al. | |
| 2008/0266172 A1 | 10/2008 | Reinpoldt | |
| 2009/0033548 A1* | 2/2009 | Boxman | G01S 13/284 342/179 |
| 2009/0135078 A1 | 5/2009 | Lindmark et al. | |
| 2009/0195435 A1 | 8/2009 | Kapilevich et al. | |
| 2009/0262006 A1 | 10/2009 | McNeill et al. | |
| 2009/0295618 A1 | 12/2009 | Beeri et al. | |
| 2010/0117885 A1 | 5/2010 | Holbrook et al. | |
| 2010/0225299 A1 | 9/2010 | Nguyen et al. | |
| 2010/0295718 A1 | 11/2010 | Mohamadi et al. | |
| 2011/0025546 A1 | 2/2011 | Cook et al. | |
| 2011/0050479 A1 | 3/2011 | Mohamadi et al. | |
| 2011/0102234 A1 | 5/2011 | Adams et al. | |
| 2011/0237939 A1 | 9/2011 | Melamed et al. | |
| 2013/0044182 A1 | 2/2013 | Chen | |
| 2013/0207830 A1 | 8/2013 | Watts et al. | |
| 2014/0176157 A1 | 6/2014 | Melamed | |
| 2014/0293007 A1* | 10/2014 | Angot | H04N 13/026 348/45 |
| 2014/0368373 A1 | 12/2014 | Crain et al. | |
| 2015/0025788 A1 | 1/2015 | Crain et al. | |
| 2015/0054671 A1 | 2/2015 | Mohamadi | |
| 2015/0071381 A1 | 3/2015 | Nadiri et al. | |
| 2015/0077282 A1 | 3/2015 | Mohamadi | |
| 2015/0153449 A1 | 6/2015 | Kosowsky | |
| 2015/0177372 A1 | 6/2015 | Poisner | |
| 2015/0212129 A1 | 7/2015 | Chayat | |
| 2015/0285900 A1 | 10/2015 | Melamed | |
| 2015/0311591 A1 | 10/2015 | Golombek | |
| 2017/0315227 A1* | 11/2017 | Ghazanfarpour | G01S 7/20 |

FOREIGN PATENT DOCUMENTS

| | | |
|---|---|---|
| WO | 2007/008204 A1 | 1/2007 |
| WO | 2011/068887 A2 | 6/2011 |
| WO | 2014/037943 A1 | 3/2014 |
| WO | 2014/141268 A1 | 9/2014 |
| WO | 2015/054601 A2 | 4/2015 |
| WO | 2015/114626 A1 | 8/2015 |
| WO | 2016/065262 A1 | 4/2016 |

OTHER PUBLICATIONS

International Search Report and Written Opinion, dated Nov. 16, 2017, for International Application No. PCT/US2017/045610, 8 pages.

Lamb, "Miscellaneous Data on Materials for Millimetre and Submillimetre Optics," *International Journal of Infrared and Millimeter Waves* 17(12):1997-2034, 1996.

"Properties of Materials," in *Reference Data for Radio Engineers*, International Telephone and Telegraph Company, New York, Jan. 1, 1962, pp. 62-71.

International Search Report, dated Aug. 3, 2017, for International Application No. PCT/US2017/029577, 6 pages.

International Search Report, dated Jul. 20, 2017, for International Application No. PCT/US2017/029581, 13 pages.

International Search Report, dated Jul. 18, 2017, for International Application No. PCT/US2017/029446, 13 pages.

International Search Report, dated Jul. 13, 2017, for International Application No. PCT/US2017/029449, 13 pages.

International Search Report, dated Jul. 20, 2017, for International Application No. PCT/US2017/029579, 15 pages.

Zizka et al., "SpeckleSense: Fast, Precise, Low-cost and Compact Motion Sensing using Laser Speckle," *UIST' 11*, Oct. 16-19, 2011, Santa Barbara, CA, US, 10 pages, 2011.

Extended European Search Report, dated Mar. 27, 2018, for European Application No. 17208418.8-1206, 9 pages.

*American Heritage Dictionary,5th* Edition, Houghton Mifflin Harcourt, Boston Massachusetts, 2016, "Panorama," downloaded from https://search.credoreference.com/content/entry/hmdictenglang/panorama/0, 2 pages.

International Preliminary Report on Patentability, dated Oct. 30, 2018, for International Application No. PCT/US2017/029446, 9 pages.

International Preliminary Report on Patentability, dated Oct. 30, 2018, for International Application No. PCT/US2017/029449, 9 pages.

International Preliminary Report on Patentability, dated Oct. 30, 2018, for International Application No. PCT/US2017/029577, 7 pages.

* cited by examiner

| RF Image (x, y, z) | Optical Image (x, y) | | Position (x, y, z) | Orientation |
| --- | --- | --- | --- | --- |
| | IR Image (x, y) | VL Image (x, y) | | |
| RF Image 1 | IR Image 1 | VL Image 1 | (0, 0, 0) | Vertical |
| RF Image 2 | IR Image 2 | VL Image 2 | (-2in, -2in, 0) | Vertical |
| RF Image 3 | IR Image 3 | VL Image 3 | (-4in, -2in, -0.01in) | Vertical |
| RF Image 4 | IR Image 4 | VL Image 4 | (-4in, -4in, +0.01in) | -4 degrees |
| RF Image 5 | IR Image 5 | VL Image 5 | (-2.1in, -4in, 0) | +2 degrees |

OPTICAL IMAGE CAPTURE WITH POSITION REGISTRATION AND RF IN-WALL COMPOSITE IMAGE

BACKGROUND

Technical Field

This application is related to a radio frequency (RF) imaging device, and, in particular, an RF imaging device that performs RF imaging of objects disposed within or behind a surface.

Description of the Related Art

Various structures such as homes and office buildings use paneling, such as drywall or lath and plaster, to separate dwelling spaces from electrical wiring systems, structural systems and plumbing systems, among others, that are disposed behind the paneling. Other structures may use other construction materials, such as cinderblock, where the wiring, plumbing, etc. may run internally to the building material. In some cases, plumbing and wiring, for example, are directly embedded into cement or plastered into masonry of various structures. During maintenance, repair, or remodeling projects, personnel often cut or excavate the paneling or building material to access these systems and later patch the paneling. For example, drywall may be cut to access a metal pipe or wooden stud of interest behind the drywall. The ability to accurately identify a position on a surface behind which an object of interest is located reduces the labor and equipment costs associated with building maintenance, repair, and remodeling.

Commercially available devices, such as stud finders, do not accurately identify positions on a wall behind which objects of interest are disposed. Furthermore, these devices do not perform imaging of spaces behind walls or characterize the material composition of the objects, such as plastic or metal pipes, so as to enable construction personnel to pinpoint excavation areas.

BRIEF SUMMARY

In various embodiments, disclosed herein is a radio frequency (RF) imaging device comprising a position sensor, an RF sensor assembly, an optical sensor, and a processor. The position sensor is configured to determine a position of the RF imaging device relative to a surface. The RF sensor assembly is configured to capture RF image data representing an RF image of a portion of a space behind the surface at the determined position. The optical sensor is configured to capture optical image data representing an optical image of the surface at the determined position. The processor is configured to produce a composite image in which at least one or more portions of the RF image and one or more portions of the optical image that correspond to the same position relative to the surface are simultaneously viewable. The RF imaging device may further comprise a memory in which the RF image data and the optical image data are stored in association with position data derived from the determined position of the RF imaging device.

In at least one embodiment, the RF sensor assembly captures a plurality of RF images at a respective plurality of positions relative to the surface, each RF image being an RF image of a portion of the space behind the surface at the respective plurality of positions. The optical sensor captures a plurality of optical images of the surface at the respective plurality of positions. The processor is configured to assemble (1) a panoramic RF image of the space behind the surface based on the plurality of RF images, and (2) a panoramic optical image of the surface based on the plurality of optical images, and produce a composite image in which at least one or more portions of the panoramic RF image and one or more portions of the panoramic optical image that correspond to the same position relative to the surface are simultaneously viewable.

The processor may be configured to assemble the panoramic RF image by collating the plurality of RF images of the space behind the surface at the respective plurality of positions, and to assemble the panoramic optical image by collating the plurality of optical images of the surface at the respective plurality of positions. Collating the plurality of RF images may include identifying RF image data in the plurality of RF images at different positions relative to the surface and assembling the RF image data at each position to form the panoramic RF image, and collating the plurality of optical images may include identifying optical image data in the plurality of optical images at different positions relative to the surface and assembling the optical image data at each position to form the panoramic optical image. The RF imaging device may further comprise a memory in which (1) the RF image data forming the panoramic RF image is stored in association with position data indicating the respective positions of the RF image data relative to the surface, and (2) the optical image data forming the panoramic optical image is stored in association with position data indicating the respective positions of the optical image data relative to the surface.

In at least one embodiment, the RF imaging device further comprises a tilt sensor that determines an orientation of the RF imaging device relative to the surface when the RF image data and the optical image data are captured. The orientation specifies a rotation of the respective RF image and optical image about an axis in relation to the surface. The RF image data and the optical image data are adjusted based on the specified rotation so that the RF image and the optical image have a common orientation relative to the surface.

In at least one embodiment, the RF image data representing the RF image at the determined position and the optical image data representing the optical image at the determined position are captured at different times. The RF imaging device may be moved to a different position relative to the surface between capturing the RF image data representing the RF image and capturing the optical image data representing the optical image.

In various embodiments, also disclosed herein is a radio frequency (RF) imaging device comprising a position sensor configured to capture signal data representing a plurality of signals respectively emitted by a plurality of position markers at known positions relative to a surface; an optical sensor configured to capture optical image data representing an optical image of the surface; and a processor operatively coupled to the position sensor and the optical sensor. The processor is configured to receive the signal data representing the plurality of signals; determine a position of the position sensor relative to the surface based on the known positions of the position markers and analysis of the signal data; associate the optical image data with position data derived from the determined position of the position sensor; and produce a composite image in which one or more portions of the optical image data are simultaneously viewable with RF image data representing an RF image of a space behind the surface at the same position relative to the surface as the optical image data, based on the position data associated with the one or more portions of the optical image data.

In at least one embodiment, the RF imaging device further comprises a memory in which the optical image data and the RF image data are stored together in association with the position data derived from the determined position of the position sensor.

In at least one embodiment, the RF imaging device further comprises a communication interface configured to transmit the composite image to a receiving device.

In at least one embodiment, a position marker of the plurality of position markers includes an active transmitter that has a power source and is configured to transmit a signal of the plurality of signals to the position sensor. Alternatively or additionally, a position marker may include a passive transmitter that is induced to transmit a signal of the plurality of signals in response to receiving an activating signal.

The position of a position sensor relative to the surface may be determined based on the known positions of the position markers and triangulation of the signal data. Alternatively or additionally, the position of a position sensor relative to the surface may be determined based on the known positions of the position markers and a determined time-of-flight for each of the plurality of signals transmitted from the respective position markers.

In at least one embodiment, the optical sensor captures optical image data representing a plurality of optical images of the surface at a respective plurality of positions. The processor is further configured to assemble a panoramic optical image of the surface based on the optical image data representing the plurality of optical images, wherein the optical image data in the panoramic optical image is associated with position data derived from determined positions of the position sensor corresponding to when the optical image data representing the plurality of optical images was captured. The processor is further configured to produce a composite image in which at least one or more portions of the optical image data in the panoramic optical image are simultaneously viewable with RF image data representing the RF image of the space behind the surface captured at the same position as the optical image data in the panoramic optical image, based on the position data associated with the one or more portions of the optical image data.

In at least one embodiment, the RF image data representing an RF image of a space behind the surface represents a three-dimensional (3D) RF image.

In various embodiments, also disclosed herein is a radio frequency (RF) imaging device comprising a position sensor configured to capture data representing a positioning image; an optical sensor configured to capture data representing an optical image of a surface; and a processor operatively coupled to the position sensor and the optical sensor. The processor is configured to receive the data representing the positioning image; determine, based on the data representing the positioning image, that a position reference marker is present in the positioning image; as a result of determining that the position reference marker is present in the positioning image, determine a reference position for the RF imaging device; associate the data representing the optical image of the surface with position data derived from the determined reference position; and produce a composite image in which one or more portions of the data representing the optical image are simultaneously viewable with data representing an RF image of a space behind the surface at the same position as the one or more portions of the data representing the optical image, based on the position data associated with the one or more portions of the data representing the optical image.

In at least one embodiment, the RF imaging device further comprises a displacement sensor configured to detect a displacement of the RF imaging device relative to the reference position and to output data representing the displacement. The optical sensor is configured to capture data representing a subsequent optical image of the surface after the displacement of the RF imaging device has occurred. The processor is configured to receive the data representing the displacement; determine a subsequent position of the RF imaging device based on the data representing the displacement and the reference position; and associate the data representing the subsequent optical image with position data derived from the determined subsequent position of the RF imaging device.

In at least one embodiment, the processor is further configured to assemble a panoramic optical image of the surface based on the data representing the optical image at the reference position and each subsequent position of the RF imaging device, wherein the data in the panoramic optical image is associated with position data derived from the reference position or a subsequent position of the RF imaging device corresponding to when the data representing the optical image or the subsequent optical image was captured. The processor is further configured to produce a composite image in which at least one or more portions of the data in the panoramic optical image are simultaneously viewable with RF image data representing the 3D RF image of the space behind the surface at the same position as the data in the panoramic optical image, based on the position data associated with the one or more portions of the data in the panoramic optical image. In at least one embodiment, the data representing an RF image of a space behind the surface represents a three-dimensional (3D) RF image.

DETAILED DESCRIPTION

Figure 1:
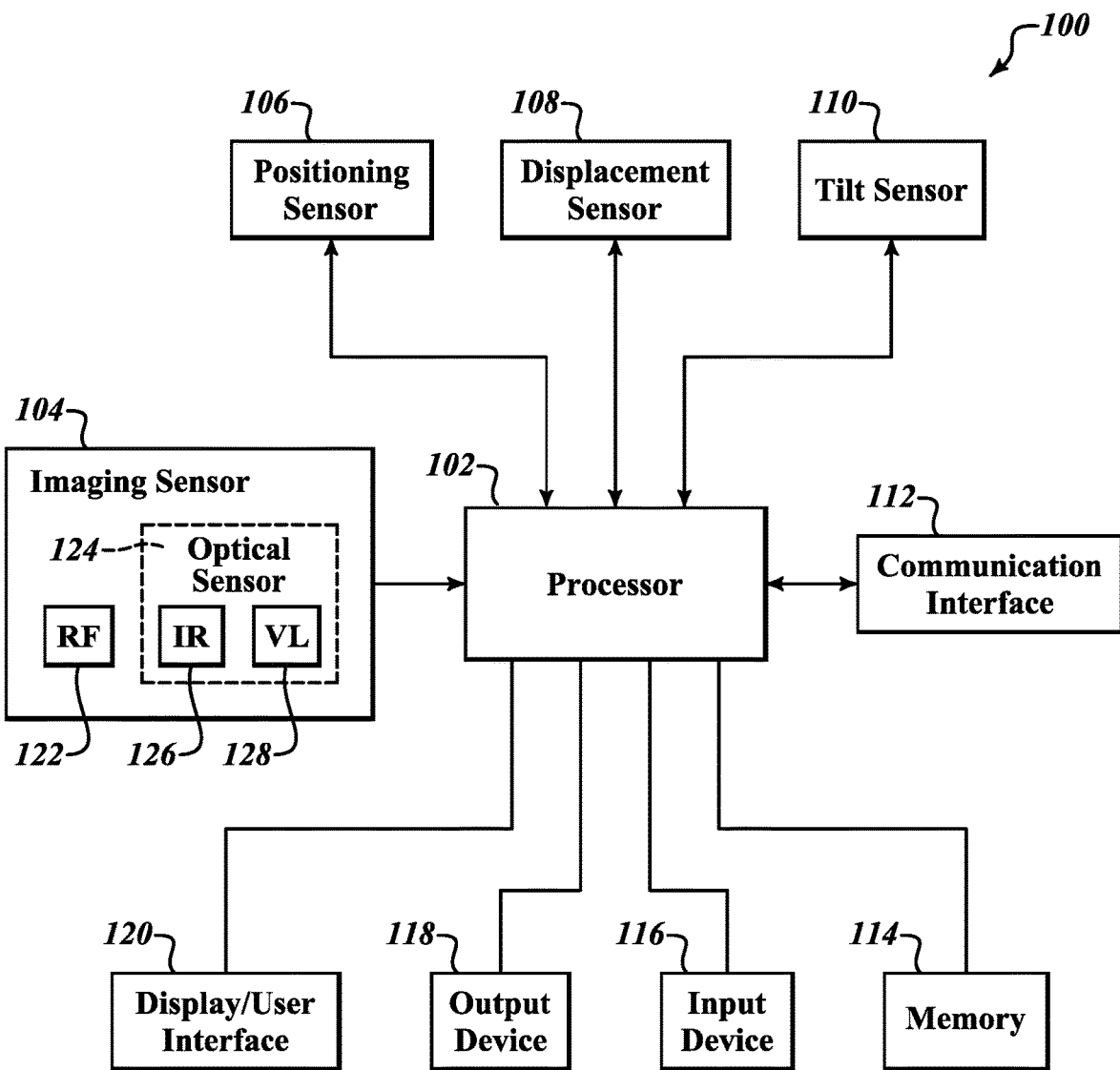
FIG. 1 shows a block diagram of a radio frequency (RF) imaging device in accordance with at least one embodiment.

FIG. 1 shows a block diagram of a radio frequency (RF) imaging device 100 in accordance with at least one embodiment. As configured in FIG. 1, the RF imaging device 100 comprises a processor 102 along with imaging sensors 104, a positioning sensor 106, a displacement sensor 108, a tilt sensor 110, a communication interface 112, a memory 114, an input device 116, an output device 118, and a display 120, that are operatively coupled to the processor 102. The imaging sensors 104 include an RF sensor assembly 122 and an optical sensor 124. The optical sensor 124 shown in FIG. 1 may include an infrared (IR) sensor 126 configured to capture images in infrared wavelengths and a visible light (VL) sensor 128 configured to capture images in visible light wavelengths. In various embodiments, the optical sensor 124 may only include the IR sensor 126 or the VL sensor 128, or may include sensors configured to capture images in other wavelengths of the electromagnetic spectrum.

The RF imaging device 100 may be used to perform imaging of a space disposed behind a surface, such as a wall. In typical circumstances, the surface is opaque and objects in the space behind the surface are occluded from view. In some circumstances, objects in the space behind the surface of the wall may run internally to or be embedded in the building material that forms the wall. Using signals in the RF spectrum, the RF imaging device 100 may capture RF images of the objects in the space at different positions relative to the surface. In addition to capturing the RF images, the RF imaging device 100 may capture optical images of the surface that may include IR images and VL images. In yet other embodiments, an RF imaging device may access other sources such as another RF imaging device or a data repository in a separate computer or remote server to obtain RF images of a space behind a surface, and display those RF images, separately or together with optical images of the surface.

Objects behind a surface such as a wall may include, for example, structural objects such as studs and beams, and electrical wiring, such as wires, cables and fixtures, that are positioned within or behind the building materials forming the wall surface. Further, the space may include objects used for a plumbing system, such as pipes, drains and valves, and temperature insulation, such as glass wool and urethane foam. The objects may be made from a variety of materials including plastic (for example, polyvinyl chloride (PVC)), wood and metal (for example, copper, iron and lead). Each type of material may reflect an impinging RF wave differently and may, thus, have a unique RF signature. The unique RF signature of different materials may be utilized by the RF imaging device to distinguish between the materials of the objects detected behind the surface.

Furthermore, different objects behind a surface may have different temperatures. The temperature difference between two objects is identifiable using IR imaging. For example, a hot water pipe and a cold water pipe have differing temperatures are identifiable/visible via IR imaging of the surface. In addition, because a stud has higher heat conductivity than surrounding insulation, a stud may be readily identifiable using IR imaging when there is a temperature differential between an exterior and an interior of a walled structure.

The RF sensor assembly 122 includes one or more RF sensors (for example, antennas). In cases where the RF sensor assembly 122 has multiple RF sensors, the sensors may be arranged in a one-dimensional array (for example, in a row) with intra-sensor spacing therebetween. The arrangement and intra-sensor spacing may be uniform. Alternatively, the RF sensor assembly 122 may include multiple RF sensors arranged in a planar array that has rows and columns of sensors.

In some cases, the RF sensor assembly 122 may include multiple RF sensors arranged in a three-dimensional (3D) array whose sensors are arranged in a 3D matrix. It is worth noting that in various cases the spacing between the sensors of the RF sensor assembly 122 may not be uniform and the intra-sensor spacing may differ for various pairs of sensors.

The RF sensor assembly 122 senses an RF wave reflected by the objects disposed behind the surface and captures reflection data representing the sensed reflection of the RF wave. The RF wave that impinges upon the objects may be emitted by the RF sensor assembly 122 or, alternatively, another RF emitter (not shown in FIG. 1) may emit the RF wave.

The RF sensor assembly 122 outputs the reflection data to the processor 102. The processor 102 utilizes the reflection data to generate an RF image of the space behind the surface. For example, U.S. Pat. Nos. 8,494,615, 8,077,072, United States Pre-Grant Publication No. 2015/0311591, and International Patent Application Publication No. WO 2011/068887, whose contents are hereby incorporated by reference herein, describe technology that may be used for the RF sensor assembly 122 to perform through-the-wall RF imaging of objects in a space behind a wall. The resulting RF image may be a three-dimensional (3D) image or a two-dimensional (2D) image.

As will be described in greater detail herein, the processor 102 may generate a composite image that combines the RF image with another image, such as an optical image. In some cases, the composite image superposes the RF image of the space behind the surface at a position with an IR image of the surface at the same position and/or a visible light image of the surface at the same position. A composite image that includes a visible light image of the surface may be used, for example, by construction or maintenance personnel to accurately identify a position on the surface behind which an object of interest, such as a PVC pipe or electrical wiring, is located.

When the composite image includes an IR image, the IR image further enhances the composite image. For example, whereas a hot water metal pipe and a cold water metal pipe may not be distinguishable based on a reflected RF wave used to generate the RF image, the distinct heat signatures of the two pipes visible in the IR component of the composite image may help distinguish the two pipes.

In addition to composite images, the processor 102 may generate a panoramic RF image by collating the RF image with other RF images captured at other positions relative to the surface. The panoramic RF image may provide a sweeping view of a larger space, or even an entire space, disposed behind the surface as opposed to localized RF images of portions of the space.

Figure 2:
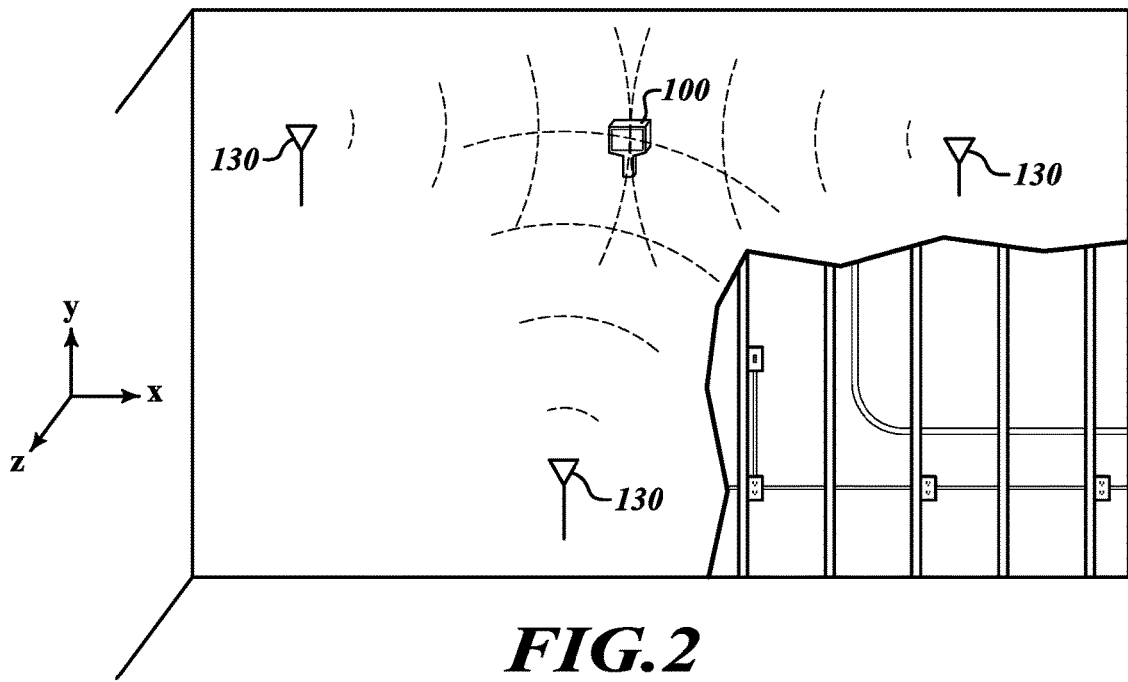
FIG. 2 shows the RF imaging device positioned relative to a surface having a plurality of position markers disposed thereon.
Figure 7:
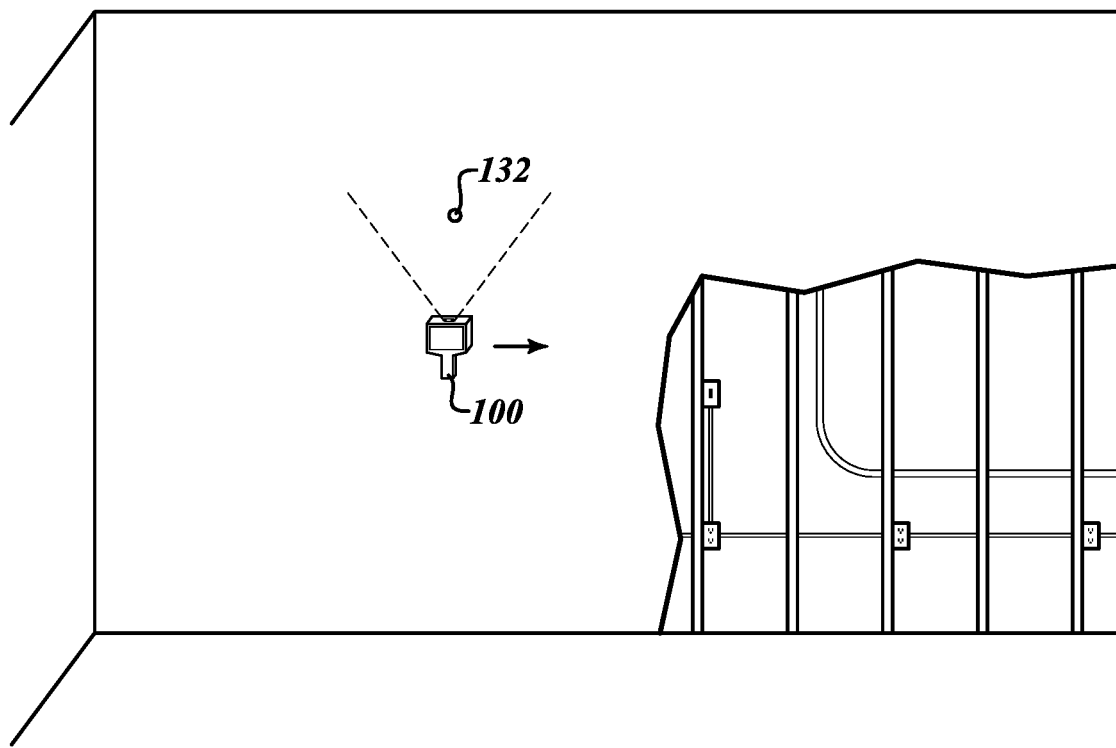
FIG. 7 shows the RF imaging device positioned relative to a surface having a reference marker disposed thereon.

In some embodiments, the positioning sensor 106, which may include one or more RF antennas, receives a plurality of signals that are respectively emitted by a plurality of positions markers (see, e.g., FIGS. 2 and 7). The plurality of position markers may be wireless emitters and may respectively emit (either passively or actively) the plurality of signals. The plurality of position markers may have known positions relative to the surface, or have positions that become known through interaction of the RF imaging device 100 with the position markers. For example, the plurality of position markers may be placed on the surface or at other known locations in an area of a structure, such as a room.

In some embodiments, the plurality of signals may be used for determining a position of the RF imaging device 100 by triangulation as described herein. Other embodiments may involve time-of-arrival estimation or angle-of-arrival estimation of signals emitted by position markers and received by the positioning sensor 106. Triangulation typically uses information from which both angle and distance from the RF imaging device to the position marker can be determined. In cases where the position marker is an active emitter, the angle between the device and the position marker can be determined, and if both the position marker and the RF imaging device 100 are synchronized to a common time at a sufficient resolution, the distance between the device and the position marker can also be determined. In cases where the position marker "emits" a signal by reflecting a signal emitted by the RF imaging device, the transit time of the signal between the RF imaging device and the position marker can be measured and used to determine the distance between the device and the position marker.

The positioning sensor 106 outputs data representing the plurality of signals to the processor 102. The processor 102, in turn, determines the position of the RF imaging device 100 based on the plurality of signals. The position may be an absolute position or a relative position in relation to a reference position.

For example, if the position of the RF imaging device 100 is determined by triangulation, time-of-arrival estimation, or angle-of-arrival estimation, of signals emitted by position markers having known position, the determined position is an absolute position. However, if the position is determined in relation to a position marker having an unknown position, the position may be said to be a relative position. The processor may associate the absolute or relative position of the RF imaging device 100 with the captured image data used to generate the RF or optical image and cause the position together with the captured RF or optical image to be stored in the memory 114. The captured and stored RF or optical image and position data may be subsequently used to produce panoramic images or composite images.

In some embodiments, the positioning sensor 106 may be an optical sensor, such as a visible light sensor or an IR sensor, having a field of view. The positioning sensor 106 may accordingly capture an optical image of the field of view of the positioning sensor 106. The optical image may be used for detecting an optical signature (for example, a unique optical signature) of an optical position reference marker that is present in the optical image. In various embodiments, the presence of the optical signature in the optical image causes the processor 102 to deem the position of the positioning sensor 106, at the time when the optical image is captured, a reference position.

If the positioning sensor 106 determines a relative position, the RF imaging device 100 may include a displacement sensor 108 for detecting displacement of the RF imaging device 100 relative to the reference position as the RF imaging device is moved about the surface. In some cases, the displacement sensor 108 may be an optoelectronic sensor or an inertial sensor. The displacement sensor 108 may sense a displacement of the RF imaging device 100 from a position, such as the reference position. The displacement sensor 108 outputs data representing the displacement to the processor 102.

The tilt sensor 110, which in some cases may be a gyroscope or an accelerometer, detects an orientation of the RF imaging device 100 and outputs data representing the detected orientation to the processor 102. The orientation may be an angle that an axis of the RF imaging device 100 makes relative to an axis, such a vertical axis or a horizontal axis, that lies in a plane defined by the surface. The processor 102 may cause the data representing the detected orientation to be stored together with the captured RF or optical image data in the memory. The processor 102 may use the orientation to determine whether the RF imaging device 100 was tilted when the RF or optical image was captured. If the RF imaging device was determined to have been titled differently when an RF or optical image is captured as compared to the orientation of the device 100 when other RF or optical images were captured, the processor 102 may adjust or reorient the RF or optical image such that its resulting orientation matches that of the other RF or optical images. Thus, all the RF or optical images used to produce a panoramic image will have the same orientation. Scaling of captured RF or optical images may also be performed to ensure that all the RF or optical images used to produce a panoramic image have the same scale.

In some embodiments, motion of the RF imaging device 100 may be determined by comparing subsequent images from any imager within the device, and tracking the displacement of objects within the subsequent images using known image processing techniques. This process may be performed with any type of imagery (IR, VL, RF, etc.). In some embodiments, relative motion and/or absolute motion of the RF imaging device 100 may be determined by combining one or more of the aforementioned data types, i.e., data obtained from the positioning sensor 106, displacement sensor 108, tilt sensor 110, and/or data derived from image processing.

The communication interface 112, which may be any type of communication port or transceiver, communicates data between the RF imaging device 100 and another device. The communication interface 112 may be used to send data, such as RF images, optical images, panoramic images or composite images to the other device, which may be a display device, such as a projector, a computer, a tablet, a server, a smartphone, etc. The communication interface 112 may also be used to receive data, such as firmware updates and image data, and provide such data to the processor 102.

The communication interface 112 may be a wired interface or a wireless interface and may communicate in accordance with any wired or wireless communication protocol. For example, the communication interface 112 may be a universal serial bus (USB) port or an Ethernet port. Further, the communication interface 112 may be a cellular communications port that is capable of communicating over a cellular wireless network. The communication interface 112 may also communicate in accordance any Institute for Electrical and Electronics Engineers (IEEE) 802 communication protocol or a lower-power Bluetooth or ZigBee protocol, or the like.

The memory 114 may be any type of non-transitory computer readable media, such as static or dynamic random access memory (RAM) or read-only memory (ROM), or storage media such as disk drives or flash memory, among others. The memory 114 may store executable instructions that, when executed by the processor 102, cause the processor 102 to perform the techniques and actions described herein.

Furthermore, the memory 114 may store image data representing RF images or optical images together with associated data. The associated data as described herein may include, for example, a position of the RF imaging device 100 (or the imaging sensors 104 thereof) at the time the RF images or optical images are captured. Alternatively or in addition, the associated data may include an orientation or displacement of the RF imaging device 100 or the imaging sensors 104 thereof. The memory 114 may also store a composite image, a panoramic, RF image, a panoramic IR image, and/or a panoramic optical image.

The input device 116 receives a user input specifying a command and outputs data representing the command to the processor 102. The input device 116 may be, for example, a joystick, press button, keyboard or scroll wheel, among others. In some embodiments, the input device 116 may be used to manipulate display of an image (such as an RF image) displayed on the display 120. For example, input device 116 may include a plurality of joysticks, whereby a first joystick is used to specify pan command to pan over the image and a second joystick is used to specify rotate command to rotate the image. In addition, the input device 116 may include press buttons for zooming in or out of the image.

The output device 118, which in some embodiments may be an ink or a label marker, receives data from the processor 102 indicating an object detected in the space behind the surface, which may include indicating a type of material of which the object is made, and produces a physical output that is placeable on the surface. For example, the physical output may be a label specifying the type of material detected. The label may be removably attached to the surface at the location that the object is detected. In another example, the physical output may be a color-coded ink mark indicating the type of material of the detected object (for example, using a specific color assigned to the type of material). The color-coded ink mark may be placed on the surface at the location that the object is detected. In cases where the type of material of the object is not determined or cannot be determined, the output device 118 may still produce a physical output that is placeable on the surface at the point of detection to indicate the position of the detected object. In some embodiments, the output device 118 may automatically produce and place the physical output, without requiring user interaction or instruction.

The display 120 receives from the processor 102 data representing an image (such as an RF image, optical image, panoramic image or composite image) and displays the image. Furthermore, the display 120 may receive data representing a user interface and display the user interface. The user interface may be graphical user interface as described herein.

It is noted that different embodiments of the RF imaging device 100 may not include all of the features and devices shown in FIG. 1. In some embodiments, the RF imaging device 100 may include more features and devices than those shown in FIG. 1. Further, the RF imaging device 100 may have different forms of construction, both internal and external. The RF imaging device 100 may have different forms of housing and the like.

FIG. 2 shows the RF imaging device 100 positioned relative to a surface having a plurality of position markers 130 disposed thereon. For purposes of illustration, FIG. 2 also shows a portion or all of a panoramic RF image depicting objects that have been detected in a space behind the surface, including a number of studs, a pipe, electrical junctions and a wire. The RF imaging device 100 may be in contact with the surface (for example, held against the surface) or positioned a distance away from the surface. Although the plurality of position markers 130 (singularly referred to herein as position marker 130) in FIG. 2 are shown to be disposed on the surface, the plurality of position markers 130 may not necessarily lie in one plane and may be placed anywhere in a 3D space.

A position marker 130 may be an active or a passive RF emitter. Examples of an active RF emitter include a battery-operated transmitting antenna that actively emits an RF signal. A passive emitter, on the other hand, may be a radio frequency identification (RFID) tag that may or may not have a battery or other independent power source. The passive emitter may be induced to transmit an RF signal in response to receiving an activating signal. Yet other examples of a passive RF emitter include one or more materials that reflect an incoming RF signal. Such passive RF emitters, or reflectors. may not generate or transmit an RF signal in a classic sense, but instead, by reflection, they cause an incoming RF signal to become an outbound RF signal appearing to originate, or be "emitted," from the position of the reflector. The reflector may be constructed of materials having known RF reflection characteristics, and such materials may be arranged in a predetermined pattern so as to cause the reflected RF signal to have a specific, detectable characteristic(s) that identifies the reflector when the reflected signal is received and processed by the RF imaging device 100.

The plurality of position markers 130 are positioned at locations or positions, typically defined relative to the surface, that are known or become known to the RF imaging device 100 or other device interacting with the position markers 130. In some circumstances, the position markers 130 may be randomly positioned, and the locations or positions of the position markers 130 are then determined, either by interaction of the RF imaging device 100 or other device with the position markers 130 or by user input to the RF imaging device 100 or other device indicating the positions of the position markers 130. As described earlier, the plurality of position markers 130 emit a respective plurality of signals. In various embodiments, the plurality of signals are received by the positioning sensor 106 of the RF imaging device 100. The positioning sensor 106 outputs data representing the plurality of signals to the processor 102. The processor 102 determines, based on angle-of-arrival (AOA) (also known as direction-of-arrival (DOA)), time-of-arrival (TOA), or other position determination or triangulation techniques, a position of the positioning sensor 106 (and by extension, a position of the RF imaging device 100 and sensors thereof) relative to the known positions of the plurality of position markers 130.

In accordance with direction-of-arrival positioning, the positioning sensor 106 may comprise a plurality of sensors (or antennas) with known intra-sensor spacing therebetween. Each sensor of the plurality of sensors receives a signal emitted by a respective position marker 130. The difference in time between receipt of the signal by the sensors of the positioning sensor 106 may be used to determine an angle at which the signal arrives at the positioning sensor 106 (or the angle-of-arrival). The angle-of-arrival is the direction of the position marker 130 in relation to the positioning sensor 106. The angle-of-arrival determination is repeated for the remaining signals of the plurality of signals. As a result, a plurality of angles-of-arrival respectively corresponding to the plurality of position markers 130 is determined. The angles-of-arrival are triangulated to identify the position in space of the RF imaging device 100. Although three position markers are shown in FIG. 2, it is recognized that more position markers may be used to increase the accuracy of position determination. Furthermore, in some embodiments two position markers may be used to determine the position of the RF imaging device 100 in a two-dimensional (2D) plane rather than 3D space. For example, position markers may be placed in an area of the 2D plane (e.g., in each of two corners of the area) and the angle-of-arrival of the signals from the position marker may be used to identify the position of the RF imaging device 100 in the defined area. With additional constraints, such as an area of known size and location relative to a position marker, a single position marker (placed, e.g., in a corner of the area) may be used to determine the position of the RF imaging device. In some embodiments, a sensed strength of the RF signals received from the position markers 130 by the positioning sensor 106 may be used as an indication of distance between the positioning sensor 106 and the one or more position markers 130.

In accordance with time-of-arrival positioning techniques, the plurality of position markers 130 may emit the respective plurality of signals simultaneously. Because the plurality of signals traverse space at the same speed (the speed of light), the time-of-arrival of a signal at the positioning sensor 106 is a function of (and proportional to) a distance between the positioning sensor 106 and the respective position marker 130 that emits the signal. The times-of-arrival of the respective plurality of position markers 130 may be determined by the processor 102 and triangulated to determine a position of the RF imaging device 100 relative to the plurality of position markers 130. Where the positions of the position markers 130 are known relative to the surface, determining the position of the RF imaging device 100 relative to the plurality of position markers 130 also enables determination of the position of the RF imaging device 100 relative to the surface.

Figure 3:
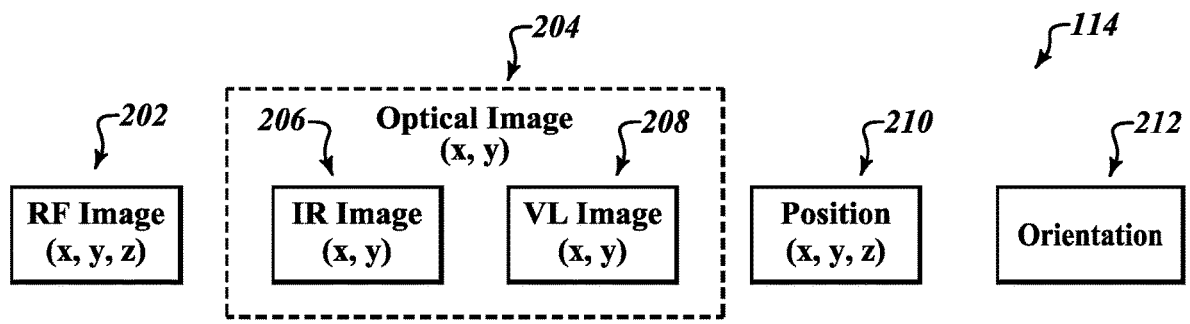
FIG. 3 shows an example of storing data representing images and associated position and orientation data of the RF imaging device.

FIG. 3 shows an example of storing data representing images and associated position and orientation data of the RF imaging device 100. The data representing images and associated position and orientation data of the RF imaging device 100 are provided by the processor 102 and stored in the memory 114. In this example, the data representing the images includes data representing an RF image 202 and data representing an optical image 204. The data representing the optical image 204 may include data representing an IR image 206 and/or data representing a VL image 208.

The associated data includes data representing a position 210 of the RF imaging device 100 when the RF image or the optical image is captured and data representing an orientation 212 of the RF imaging device 100 when the RF image or the optical image is captured. The RF image may be a 3D or 2D image of the space behind a surface at the associated position. The optical image may be an optical image of the surface that is also captured at the associated position. The RF image and the optical image may be captured at the same time or at different times. The data representing the position 210 of the RF imaging device 100 may be determined based on triangulation of the plurality of signals respectively emitted by the plurality of position markers 130.

The coordinate system shown in FIG. 3 is applicable at least to a single wall environment. The data that is generated and stored according to FIG. 3 may be expanded to account for multiple walls, e.g., by providing three-dimensional coordinates (x,y,z) for the images (RF, IR and VL images) and including additional data to indicate a wall facing direction for each wall (for example, 0 degrees to 360 degrees, detected by compass direction relative to the earth's magnetic north). The data in FIG. 3 may also (or alternatively) be expanded to include a predetermined number assigned to each wall for identification and reference purposes.

The three-dimensional datasets for the RF images 202 may be expanded to include coordinate data indicating depths behind the wall surface that specify edges or other aspects of objects behind the surface detected by the RF signals. For instance, the RF image (x,y,z) coordinates shown in FIG. 3 may be expanded to be (x, y, z1, z2) where z1 represents a depth from the surface of the wall to the nearest RF data in the RF image dataset and z2 represents the depth to the furthest RF data in the RF image dataset. In cases where a two-dimensional plane of RF data is captured, z1 equals z2.

As shown in FIG. 3, the position of the RF imaging device 100 in 3D space when a first RF image or optical image is captured may be deemed as a point of origin. The positions of the RF imaging device 100 when subsequent RF or optical images are captured may be determined and stored in relation to the deemed point of origin. In other embodiments, however, the position of the RF imaging device 100 at a time when any other RF image is captured may be deemed as a point of origin and the positions of the RF imaging device 100 at times when other RF images including the first RF image are captured may be determined and stored in relation to the deemed point of origin.

The data representing the position 210 may be used when collating a plurality of RF or optical images to produce a panoramic RF image or panoramic optical image. For example, to produce a panoramic RF image, a plurality of RF images are collated (or "stitched together") in accordance with the position of the RF imaging device 100 at each instance when the RF images were respectively captured, taking into account any overlap between adjacent images. The data representing the position 210 is also useful at later times when retrieving previously-captured RF or optical image data from the memory to reproduce an RF image or optical image at a current position of an RF imaging device being used to display the previously-captured RF and optical images.

The orientation of the RF imaging device 100 about a vertical axis (y-axis, for example) when an RF image is captured may also be used for producing a panoramic RF image. It is recognized that a person using an RF imaging device 100 to capture a plurality of RF images at a plurality of respective positions may not ensure that the RF imaging device 100 has the same orientation (for example, vertical orientation) at the plurality of positions. Due to the variation of the orientation of each image, some captured RF images may be titled (for example, by any number of degrees to the left or right of the vertical axis). To counteract the tilt in this example, the data representing the orientation 212 is used by the processor to reorient the captured RF image to a desired orientation (for example, the vertical orientation). After the RF image is reoriented, the RF image is collated together with other RF images having the same orientation to produce the panoramic RF image.

While FIG. 3 illustrates an embodiment in which a tilt or orientation of the RF imaging device is determined according to a single axis, it is appreciated that the RF imaging device 100 may have a multi-axial tilt sensor that detects the orientation of the RF imaging device in more than one axis, and the tilt data stored in association with the image data as shown in FIG. 3 may indicate tilt parameters measured in more than one axis. Reorientation of an image prior to collating the image data into a panoramic image may include adjustment of the image data in each of the images to account for differences in tilt over multiple axes.

Figure 4:
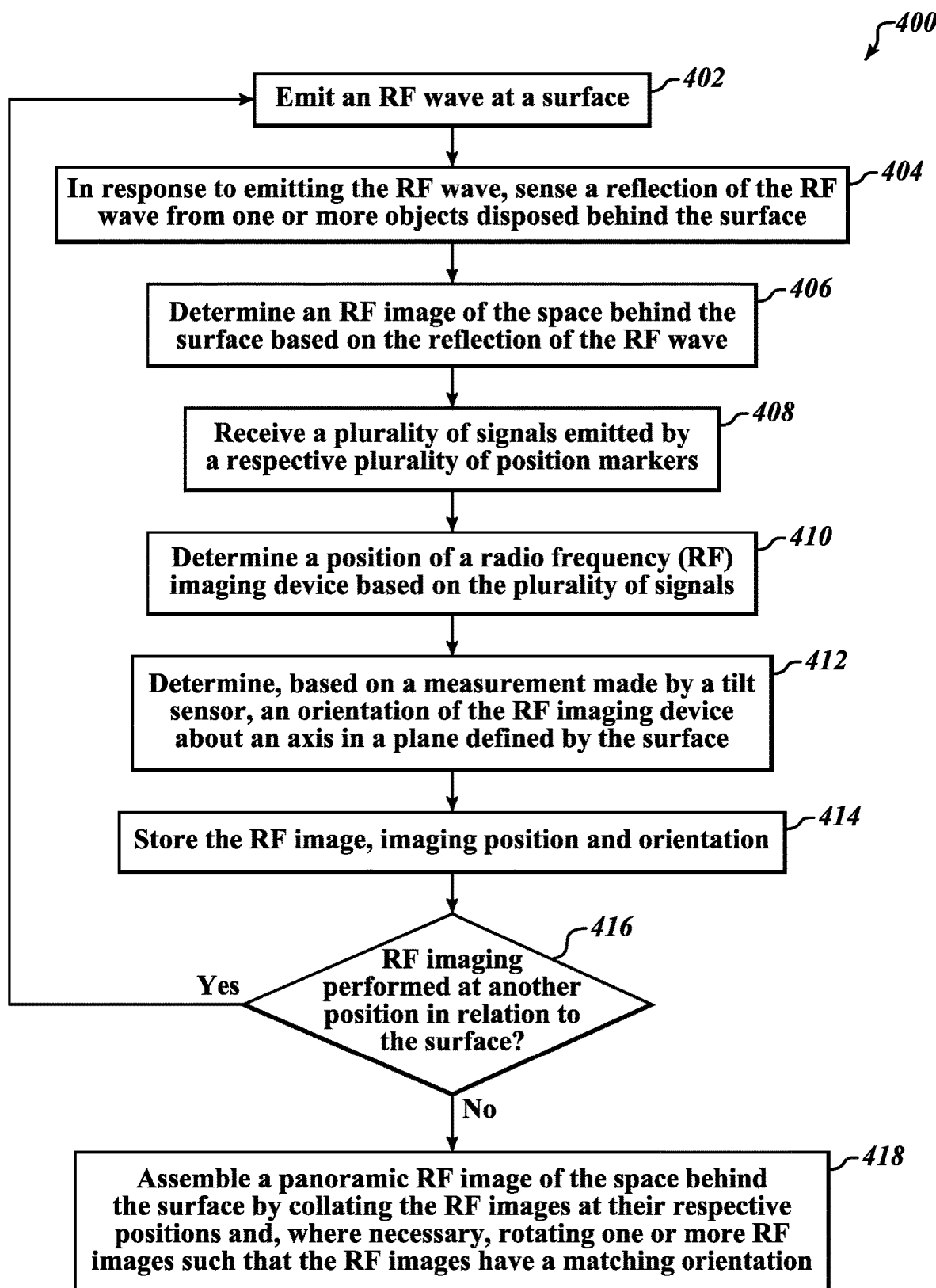
FIG. 4 shows a flow diagram of a method for assembling a panoramic RF image of a space behind a surface.

FIG. 4 shows a flow diagram of a method 400 for assembling a panoramic RF image of a space behind a surface. In the method 400, an RF sensor assembly of an RF imaging device, such as the RF sensor assembly 122 described with reference to FIG. 1, or a separate RF emitter, emits, at 402, an RF wave toward the surface. After the RF wave is emitted, the RF sensor assembly senses, at 404, one or more reflections of the RF wave from one or more objects disposed behind the surface. As described herein, the RF sensor assembly outputs data representing the reflection(s) of the RF wave to a processor, such as the processor 102 described with reference to FIG. 1. The processor determines, at 406, an RF image of the space behind the surface based on the reflection(s) of the RF wave.

A positioning sensor, such as the positioning sensor 106 described with reference to FIG. 1, receives a plurality of signals emitted by a respective plurality of position markers at 408. The positioning sensor outputs data representing the plurality of signals to the processor. The processor at 410 determines a position of the RF imaging device based on the plurality of signals. The processor also at 412 determines, based on a measurement made by a tilt sensor, an orientation of the RF imaging device about an axis in a plane defined by the surface.

At 414, the processor stores the RF image, position and orientation data in a memory, such as the memory 114 described with reference to FIG. 1. At 416, the processor determines whether RF imaging is performed at another position relative to the surface. If a positive determination is made, the method reverts to block 402, where another RF wave is emitted at the surface at the other position. The method continues to block 414, where the RF image taken at the other position is stored together with the other position and the orientation of the RF imaging device. This is repeated until a negative determination at block 416 is made.

If a negative determination is made, the processor, at 418, assembles a panoramic RF image of the space behind the surface by collating the RF images at their respective positions. Assembly of a panoramic RF image is optional. Where necessary, the processor adjusts the data in one or more RF images so that the RF images have a matching orientation.

Figure 5:
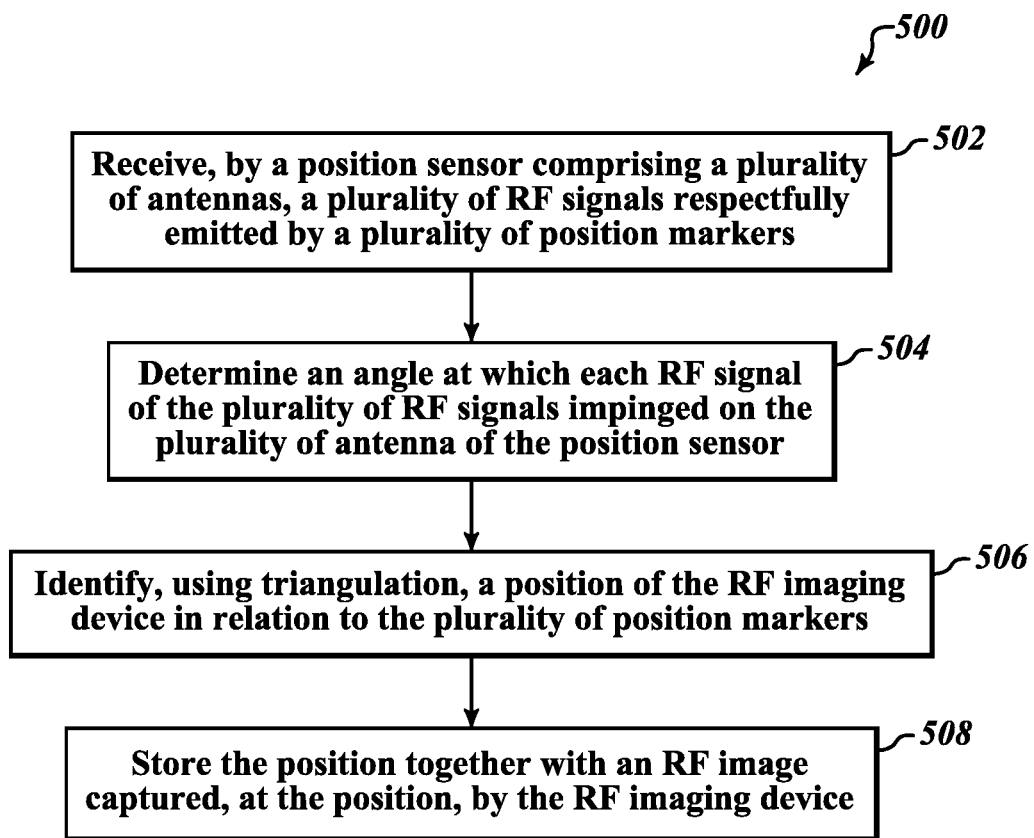
FIG. 5 shows a flow diagram of a method for determining a position of the RF imaging device based on angles-of-arrival.

FIG. 5 shows a flow diagram of a method 500 for determining a position of the RF imaging device based on angles-of-arrival of the RF signal that emanates from the active or passive position markers. In one example of the method 500, a positioning sensor comprising a plurality of antennas (such as the positioning sensor 106 described with reference to FIG. 1) receives, at block 502, a plurality of RF signals respectively emitted by a plurality of position markers. Each of the RF signals carries information or is otherwise configured to identify the respective position marker from which the RF signal was emitted. The positioning sensor outputs data representing the plurality of RF signals to a processor. The processor, at block 504, determines an angle at which each RF signal of the plurality of RF signals impinged on the plurality of antennas of the positioning sensor.

The processor, at block 506, determines a position of the RF imaging device relative to the plurality of position markers. As described herein, the plurality of position markers may have known positions. Further, in this embodiment, determining the position of the RF imaging device relative to the plurality of position markers is performed by triangulating the determined plurality of angles at which the plurality of RF signals respectively impinge on the plurality of antennas of the positioning sensor. At block 508, the processor stores the position together with an RF image captured at the position by the RF imaging device. As described herein, the RF image is determined by the processor based on data representing an RF wave reflected by objects behind a surface.

Figure 6:
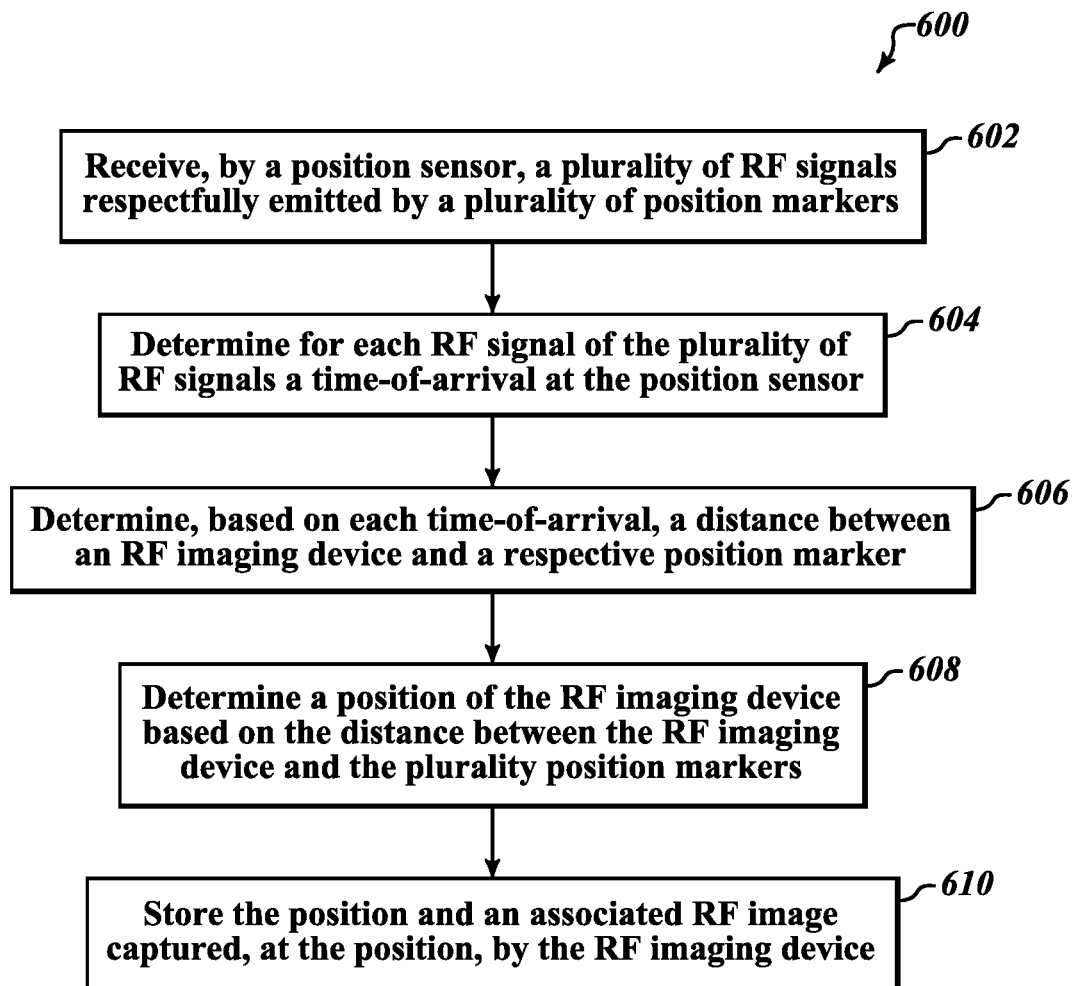
FIG. 6 shows a flow diagram of a method for determining a position of the RF imaging device based on times-of-arrival.

FIG. 6 shows a flow diagram of a method 600 for determining a position of the RF imaging device based on times-of-arrival. In the method 600, a positioning sensor (such as the positioning sensor 106 described with reference to FIG. 1) receives, at block 602, a plurality of RF signals respectively emitted (active, passive, or reflected) by a plurality of position markers. Each of the RF signals carries information or is otherwise configured to identify the respective position marker from which the RF signal was emitted. In this embodiment, the positioning sensor may only include one antenna, in contrast with angle-of-arrival-based position determination which requires the positioning sensor to include two or more sensors. The positioning sensor outputs data representing the plurality of RF signals to a processor, such as the processor 102 described with reference to FIG. 1.

At block 604, the processor determines for each RF signal of the plurality of RF signals a time-of-arrival at the positioning sensor. The plurality of position markers may be configured to emit the plurality of signals at the same time. The plurality of signals will arrive at the positioning sensor at the same time if the positioning sensor is equidistant to the plurality of position markers. The plurality of signals will arrive at the positioning sensor at different times if a distance between the positioning sensor and each of the position markers is different.

The processor, at block 606, determines based on each time-of-arrival, a distance between the RF imaging device and a respective position marker. Because the plurality of position markers have known positions, the processor determines, at block 608, a position of the RF imaging device based on the distance between the RF imaging device and the plurality position markers. The determined position of RF imaging device is an absolute position. The processor at block 610 stores the position and an associated RF image captured at the position by the RF imaging device.

In an embodiment, only one position marker may be used rather than a plurality of position markers. The one position marker may have a known position. When one position marker is used, the positioning sensor 106 may include a 2D or a 3D array of sensors. The 2D or 3D array of sensors may be used to determine both the range (i.e., distance) between the array and the position marker and the angle at which a signal emitted by the position marker impinges on the array. Based on the range and the angle, the absolute position of the positioning sensor 106 and, thus, the RF imaging device, may be determined.

FIG. 7 shows the RF imaging device 100 positioned relative to a surface having a reference marker 132 disposed thereon. FIG. 7 also shows a sample cutaway view of the space behind a portion of the surface that the RF imaging device is capable of imaging. The reference marker 132 may be removably affixed to the surface. The reference marker 132 may include, for example, a magnet, adhesive, or thumbtack, among others, for removably affixing the reference marker 132 to the surface.

In some embodiments, the reference marker 132 may have a known shape, color, pattern, reflection, composition of material, or any combination thereof that provides an optical signature of the reference marker 132. Detected in a visual image, the optical signature may be used to uniquely identify the reference marker 132. The optical signature of the reference marker 132 distinguishes the reference marker 132 from other objects in an environment.

In some embodiments, the reference marker 132 may be a mark made on the surface with an ink pen, pencil, or marker pen, such as a felt-tip pen, or a label adhesively attached to the surface. The mark may be a particular shape or symbol and may have a particular color or combination of colors that alternatively provide an optical signature of the reference marker 132 and may be used to distinguish the reference marker 132 from other objects in an environment.

The positioning sensor 106 of the RF imaging device 100 may be an optical sensor. The optical sensor may be, for example, a visible light sensor, an IR sensor, or an ultraviolet (UV) sensor. The positioning sensor 106 in these embodiments captures an optical image of the surface and outputs data representing the optical image to the processor 102. The processor 102 evaluates the optical image and determines whether the optical signature of the reference marker 132 is present in the optical image. For example, the reference marker 132 may be a cylinder whose curved surface has longitudinal stripes that alternate between red and blue, which are detectable by known image processing techniques. As another example, if the positioning sensor 106 includes an IR sensor, the detection of a particular heat signature or other IR output by the reference marker 132 may be used by the processor 102 to determine the presence of the marker 132 in the optical image.

In operation, the RF imaging device 100 is positioned at a first position relative to the surface. The RF sensor assembly 122 of the RF imaging device 100 senses one or more reflections of an RF wave from objects disposed behind the surface at the first position. As described earlier herein, the reflection(s) of the RF wave are processed to obtain a first RF image of the space behind the surface at the first position, including objects disposed in the space. Along with sensing the reflection(s) of the RF wave, the positioning sensor 106 of the RF imaging device captures an optical image of a portion of the surface including the reference marker 132. The positioning sensor 106 outputs the data representing the optical image to the processor 102.

The processor 102 knows the optical signature of the reference marker 132, whereby, for example, attributes or features of the optical signature may be stored in the memory 114. The processor 102 retrieves the features of the optical signature from the memory 114 and evaluates the optical image to determine whether the optical signature is present in the optical image. If the optical signature is found in the optical image, the processor 102 in this case may deem the first position to be a reference position. The reference position may be a point of origin and is used as a baseline or reference point for other positions as described herein. The processor 102 may then store the data representing the first RF image in association with position data representing the reference position in the memory 114.

In some embodiments, one or more of the reference markers 132 may alternatively (or additionally) be configured to reflect RF signals, similar to the "reflector" position markers 130 described earlier with regard to FIG. 2. Such reference marker(s) 132 may have a known shape, pattern, composition of material or the like, or any combination thereof, that affects the marker's reflection of an RF signal and provides an outbound reflected RF signal with a detectable RF signature that preferably uniquely identifies the respective reference marker 132. For example, the reference marker 132 may be constructed of materials having known RF reflection characteristics. In some cases, such materials may be arranged in a predetermined pattern (e.g., alternating wood and metal) so as to cause a reflected RF signal to have specific, detectable characteristics that identify the respective reference marker 132 when the RF signal reflected by the reference marker 132 is received and processed by the RF imaging device 100. The RF signature of the reference marker 132 distinguishes the reference marker 132 from other objects or reference markers 132 positioned on or near the wall surface.

Returning to FIG. 7, subsequent to obtaining the RF and optical images at the first position, the RF imaging device 100 may be moved to a second position relative to the surface. At the second position, the RF sensor assembly 122 senses one or more reflections of another RF wave from objects disposed behind the surface at the second position. The other RF wave is used for obtaining a second RF image of the space, including objects in the space, behind the surface at the second position. In at least one embodiment, the RF imaging device 100 determines the second position as a relative position based on data representing a displacement of the RF imaging device 100 from the first position.

As described herein, the RF imaging device 100 includes a displacement sensor 108, which may be an optoelectronic sensor, an inertial sensor, or other sensor capable of detecting relative positional displacement of the RF imaging device 100 relative to the surface. The displacement sensor 108 detects displacement of the RF imaging device 100 relative to the surface and outputs data representing the displacement to the processor 102. The displacement may be a movement in a relation to a plane defined by the surface. In at least one example, the displacement has a distance magnitude and units (for example, 3 inches) and a direction (for example, up/down and left/right, or an angular measurement from a defined axis in the plane). Further, in another example, the displacement may be a displacement in 3D space, where an additional axis of the 3D space is a distance of displacement away from or towards the surface.

When the displacement sensor 108 is an optoelectronic sensor, it may be directed to or pointed at the surface such that it can detect displacement of the RF imaging device 100 based on detected movement of features of the surface, such as the contours, texture, or patterns on the surface beneath the RF imaging device 100. However, if the displacement sensor 108 is an inertial sensor, then displacement of the RF imaging device 100 may be sensed based detected accelerations and decelerations of the RF imaging device. For example, the displacement sensor 108 may include one or more inertial accelerometers that consist of a mass-spring system residing in a vacuum. Exerting acceleration forces on the accelerometer results in a displacement of the mass in the spring system, and detected accelerations and decelerations enable the displacement sensor 108 to determine the direction and distance of movement of the RF imaging device 100 from one position to another.

The processor 102 determines the second position, in this case, as a relative position based on the sensed displacement of the RF imaging device 100 from the reference position. The processor 102 stores the data representing the second RF image in association with position data representing the determined second position. Having a plurality of RF images (or data representing the RF images) stored in association with a respective plurality of relative positions at which the RF images were captured, the processor 102 may produce a panoramic RF image of the space behind the surface. The panoramic RF image in this case includes the reference position.

Figure 8:
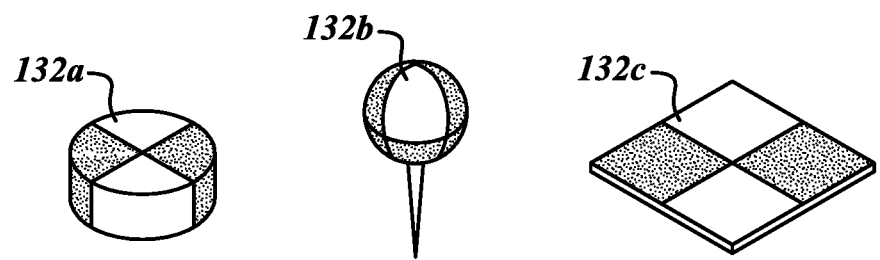
FIG. 8 shows various, non-limiting examples of reference markers.

FIG. 8 shows various, non-limiting examples of reference markers. Three reference markers 132a-c are shown in FIG. 8. The first reference marker 132a is a cylindrical magnet that is removably affixable to a surface. The cylindrical shape of the first reference marker 132a as well as the color patterns of both its curved surface and its flat surface serve as an optical signature that distinctively identifies the first reference marker 132a. The second reference marker 132b is a sphere disposed atop a pushpin. The pushpin is used for removably affixing the second reference marker 132b to a surface. The shape and/or color of the sphere of the second reference marker 132b serve as its optical signature that distinctively identifies the second reference marker 132b. The third reference marker 132c is a patch or label having an adhesive on a first side and a distinct pattern on second side. The third reference marker 132c may be removably affixed to a surface by the adhesive. The second exposed side of the third reference marker 132c provides its optical signature and distinctively identifies the third reference marker 132c. In other embodiments, the patterns shown by the reference markers 132a-c may represent different physical materials that reflect an incoming RF signal with detectable characteristics that can be used to identify the respective reference marker 132 based on the reflected RF signal.

In at least one embodiment, the positioning sensor 106 may use the visible light sensor 128 of the RF imaging device 100 to capture an optical image of the surface for sensing the position of the RF imaging device. The optical image is then used to identify the presence of the reference marker's 132 optical signature. In accordance with this embodiment, the positioning sensor 106 may not necessarily include its own optical sensor. Instead, the visible light sensor 128 may be used for the dual purpose of capturing optical images of the surface (for example, for generating panoramic optical images or composite images of the surface) and for position sensing based on the reference marker 132. As mentioned earlier, the reference marker 132 may even be, for example, a mark on the surface. In other embodiments, the positioning sensor 106 may alternatively (or additionally) use an RF emitter of the RF imaging device 100 to transmit RF signals. The transmitted RF signals are reflected by one or more of the reference markers 132 with unique RF characteristics that are usable to identify the presence and position of the one or more respective reference markers 132.

Figure 9:
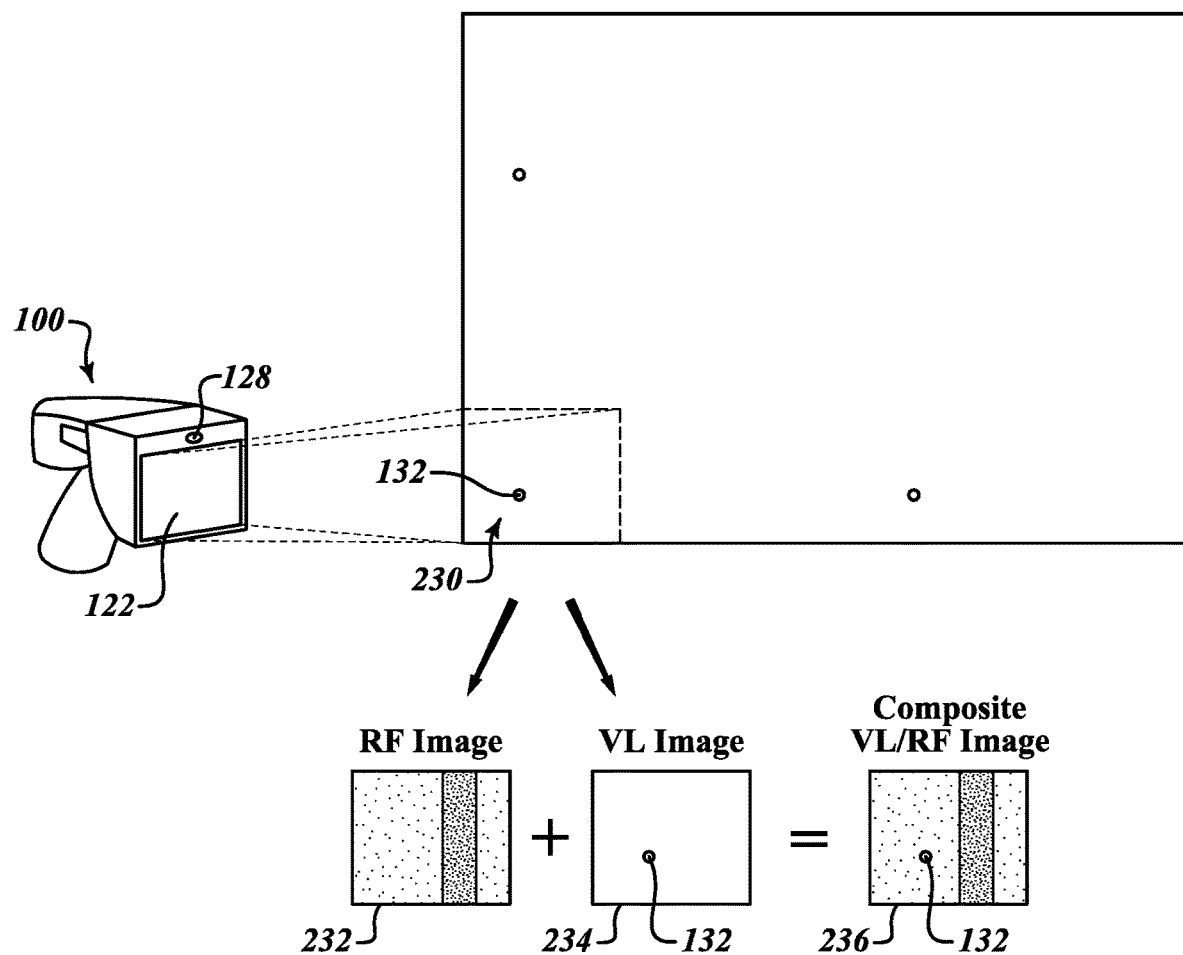
FIG. 9 shows an RF imaging device capturing both an RF image of a space behind a surface and an optical image of the surface.

FIG. 9 shows an RF imaging device 100 capturing both an RF image 232 of a space behind a surface and an optical image 234 of the surface. The surface has a reference marker 132 disposed thereon. The RF imaging device 100 includes the RF sensor assembly 122 and an optical sensor 124 that includes a visible light sensor 128.

In operation, the RF imaging device 100 is positioned in relation to the surface to take into account a directivity of a gain of the RF sensor assembly 122. As may be recognized, the gain of the RF sensor assembly 122 may or may not be isotropic. If the gain of the RF sensor assembly 122 is not isotropic, then the RF imaging device 100 may be positioned in relation to the surface such that the gain of the RF sensor assembly 122 is maximized in a direction relative to the surface. Accordingly, the RF sensor assembly 122 senses, with minimal loss, RF waves that are reflected from objects disposed behind the surface. This results in improved RF imaging of the space behind the surface. FIG. 9 illustrates an embodiment of the RF imaging device 100 positioned a distance away from the surface, while FIG. 7 illustrates an embodiment of the RF imaging device 100 positioned directly on or near the surface.

As shown in FIG. 9, the RF imaging device 100 is positioned at a first position such that a broadside of the RF sensor assembly 122 or sensors thereof is substantially parallel to a first portion of the surface (denoted as first portion 230). After an RF wave is emitted toward the surface, the RF sensor assembly 122 senses echoes of the RF wave as reflected from objects disposed behind the first portion 230 of the surface. As the field of view of the optical sensor 124 encompasses at least a portion of the first portion 230 of the surface, a primary axis of the field of view of the optical sensor 124 may be perpendicular to a plane defined by the surface.

The first portion 230 of the surface has a reference marker 132 disposed thereon. The optical sensor 124 captures an optical image 234 of the surface including the reference marker, whereby the reference marker 132 has a known optical signature. The RF imaging device 100 identifies that the optical signature of the reference marker 132 is present in the optical image 234. Based on identifying the optical signature, the first position is deemed as a reference position. Further, both the RF image of the space behind the surface and the optical image of the surface are associated with the reference position.

After capturing the RF image 232 and the optical image 234, the two images may be combined to produce a composite image 236 as shown in FIG. 9. The composite image, in some embodiments, is a superposition of the RF image on the optical image, or vice versa. As a feature that is captured in the optical image 234, the reference marker 132 will appear in the composite image 236. The presence of the reference marker 132 identifies the position of various objects behind the surface (as captured in the RF image 232) in relation to the position of the reference marker 132 on an exterior of the surface.

Figure 10:
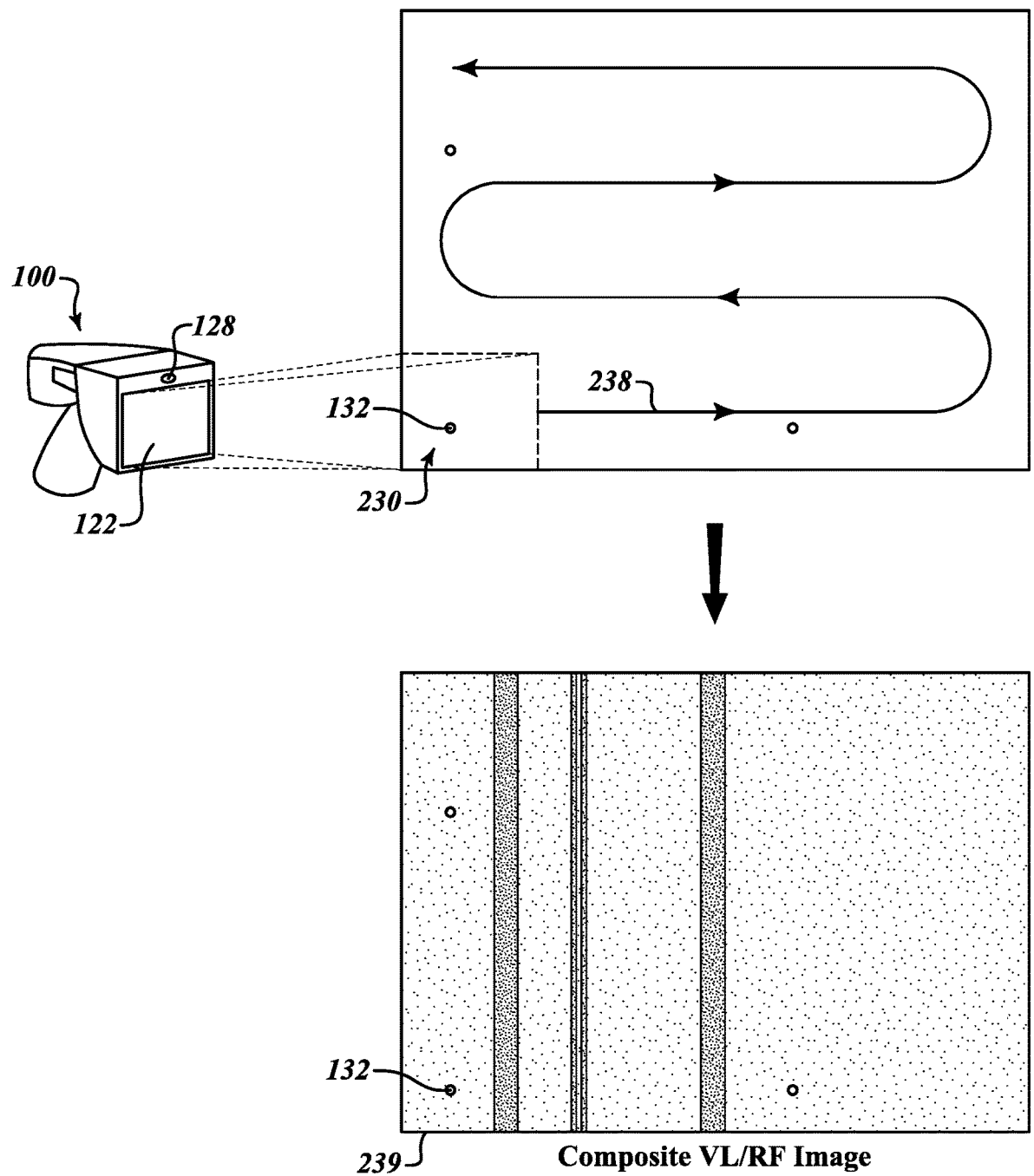
FIG. 10 shows the RF imaging device described with reference to FIG. 9 scanning the surface.

FIG. 10 shows the RF imaging device 100, described with reference to FIG. 9, scanning the surface. As described with reference to FIG. 9, the RF imaging device 100 comprises an RF sensor assembly 122 and an optical sensor 128 that is a visible light sensor. Further, the surface includes a reference marker 132. The RF imaging device 100 captures a plurality of RF images of the space disposed behind the surface using the RF sensor assembly 122. The plurality of RF images is captured at a respective plurality of positions in relation to the surface, e.g., along a scanning pattern or trajectory 238 as illustrated in FIG. 10. The RF imaging device 100 also captures a plurality of optical images of the surface at the respective plurality of positions. A first RF image and first optical image captured by the RF imaging device 100 at a first position 230 are shown in FIG. 10, whereby the first optical image includes the reference marker 132 having the known optical signature.

In the embodiment shown, the RF imaging device 100 detects the presence of the optical signature in the first optical image and deems the first position 230 as a reference position. As the RF imaging device 100 is used to scan the surface (for example, in a zigzag fashion as shown), a displacement of the RF imaging device 100 is determined for each position at which the RF imaging device 100 captures RF and optical images. Based on the sensed displacement from position to position, the remaining plurality of positions after the initial reference position are determined relative to the reference position.

The RF imaging device 100 then generates a panoramic composite image 239 based on the plurality of RF images and the plurality of optical images. To generate the panoramic composite image 239, a panoramic RF image and a panoramic optical image are generated. The panoramic RF image is generated by collating the plurality of RF images at the respective plurality of positions at which they were captured. Similarly, the panoramic optical image is generated by collating the plurality of optical images at the respective plurality of positions. The panoramic RF image and the panoramic optical image are combined (e.g., blended or superposed) to produce the panoramic composite image 239. Alternatively, the panoramic composite image 239 may be generated by producing a composite image for each position from the respective RF and optical images for each position. The plurality of composite images are then collated to generate the panoramic composite image 239.

Figure 11:
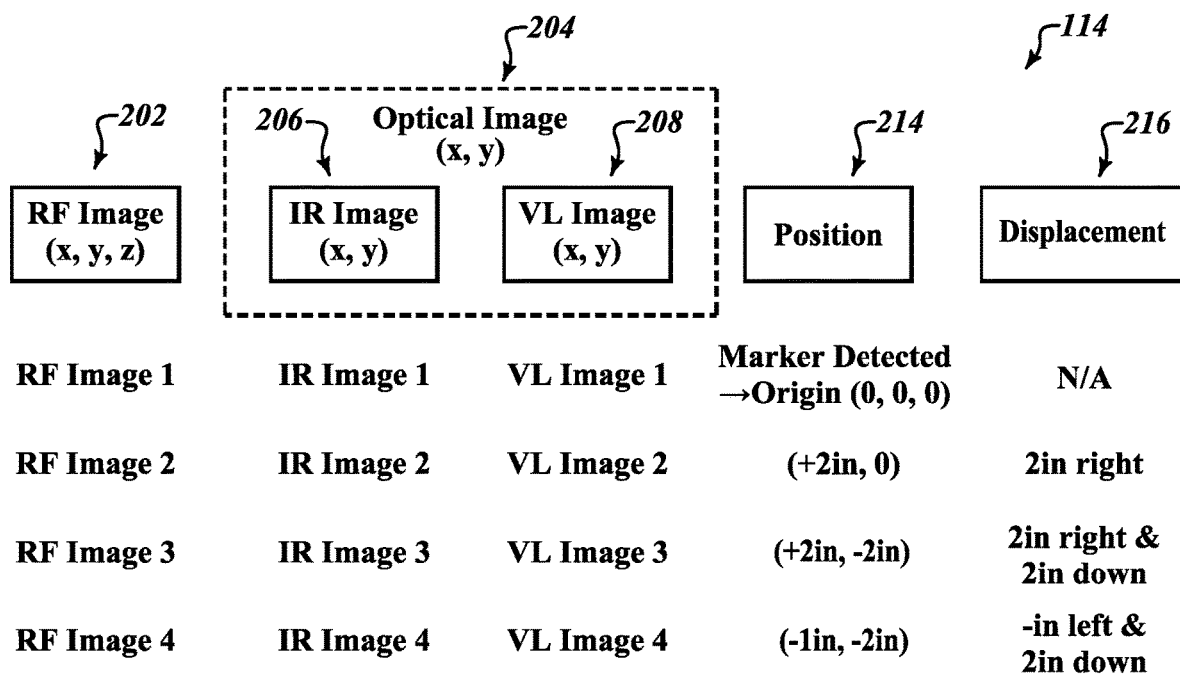
FIG. 11 shows an example of storing data representing images and associated relative position and displacement data.

FIG. 11 shows an example of storing data representing images and associated relative position and displacement data. The data representing the images and associated relative position and displacement data may be stored in the memory 114. The data representing the images includes data representing an RF image 202 and data representing an optical image 204, for example as discussed earlier in reference to FIG. 3. The data representing the optical image 204 may include data representing an IR image 206 and/or data representing a visible light image 208.

The associated data includes data representing a relative position 214 of the RF imaging device 100 when the RF image or the optical image is captured and data representing a displacement 216 of the RF imaging device 100 when the RF image or the optical image is captured.

As shown in FIG. 11, the position of the RF imaging device 100 when the signature of the reference marker 132 is detected is deemed as a reference position. The reference marker 132 may be detected by the positioning sensor 106 using its own optical sensor or using another optical imaging sensor, such as the optical sensor 124, of the RF imaging device 100. The RF imaging device 100 associates the data representing the RF image 202 captured at the reference position with the reference position. Similarly, the RF imaging device 100 associates the data representing the optical image 204 captured at the reference position with the reference position.

When the RF imaging device 100 is moved to other positions to capture other RF and optical images, the RF imaging device 100 obtains data representing the displacement 216 of the RF imaging device 100. The displacement is used to determine a position of the RF imaging device 100 relative to the reference position. The data representing the position 214 is stored together with the data representing the RF image 202 captured at the other position and the data representing the optical image 204 captured at the other position. As described herein, the stored data representing the images 202, 204 together with the data representing the position 214 of the RF imaging device 100 are used to produce panoramic and/or composite images.

Similar to the data stored in FIG. 3, the data stored in FIG. 11 may be expanded to account for multiple walls by providing three-dimensional coordinates (x,y,z) for the images (RF, IR and VL images) and/or by including additional data to indicate a wall facing direction for each wall (for example, 0 degrees to 360 degrees, detected by compass direction relative to the earth's magnetic north). The data in FIG. 11 may also (or alternatively) be expanded to include a predetermined number assigned to each wall for identification and reference purposes. Furthermore, the three-dimensional datasets for the RF images 202 may be expanded to include coordinate data indicating depths behind the wall surface specifying the location of edges or other features of objects behind the surface detected by the RF signals. For instance, the coordinates (x, y, z) shown in FIG. 11 may be expanded as (x, y, z1, z2), where the value of z1 represents a depth behind the surface of the wall to the nearest RF data in the RF image dataset, and the value of z2 represents the depth to the furthest RF data in the RF image dataset. When a two-dimensional plane of RF data is captured, z1 and z2 are equal.

Figure 12:
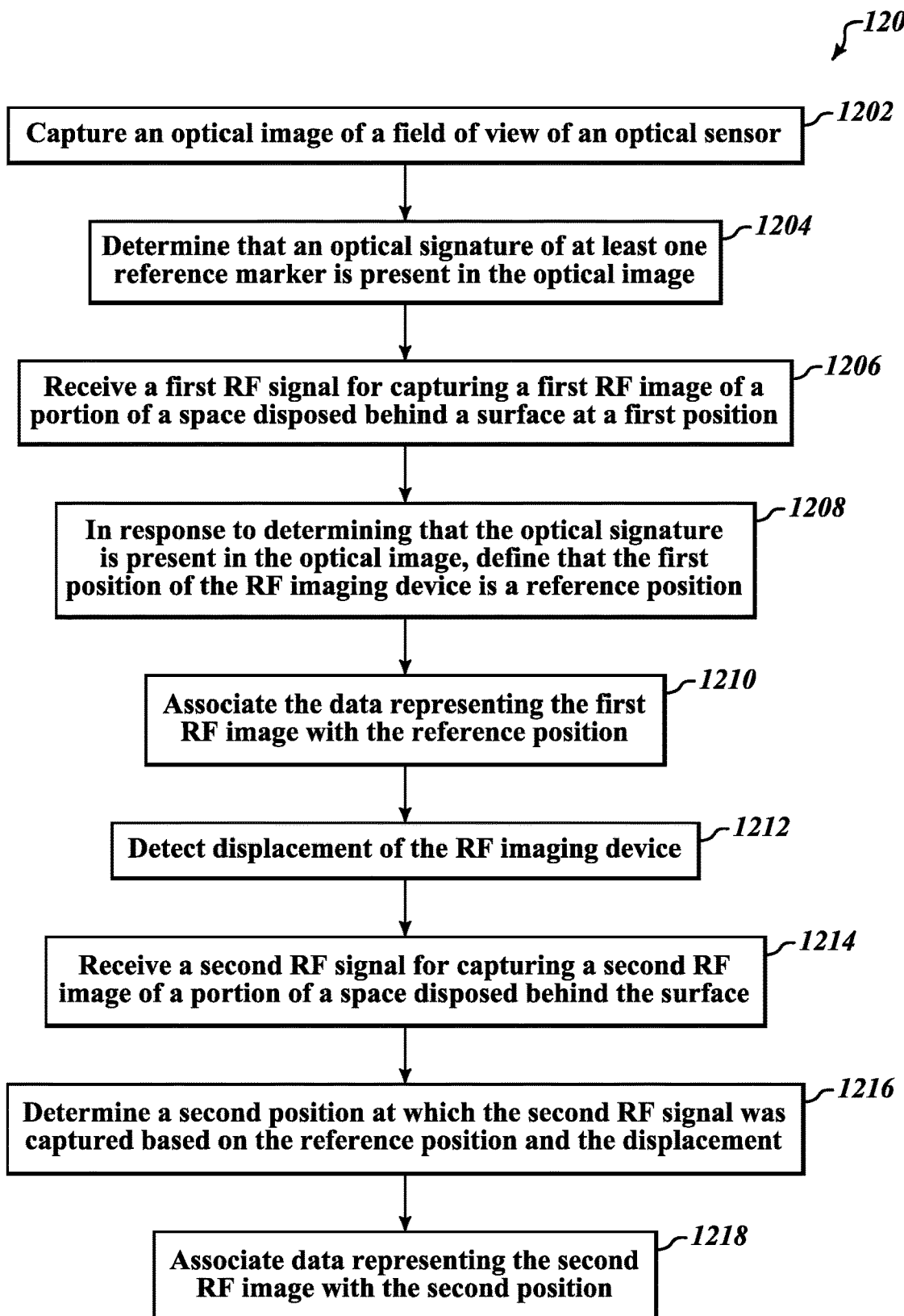
FIG. 12 shows a flow diagram of a method for associating data representing RF and optical images with position data representing positions of the images relative to the surface.

FIG. 12 shows a flow diagram of a method for associating data representing RF and optical images with position data representing positions of the images relative to the surface. In the method, an RF imaging device, such as the RF imaging device 100, captures, at block 1202, an optical image of a field of view of an optical sensor. The RF imaging device 100 at block 1204 determines that an optical signature of at least one reference marker is present in the optical image.

At block 1206, the RF imaging device 100 receives a first RF signal (i.e., reflections of a first RF wave emitted toward a surface) for capturing a first RF image of a portion of a space behind the surface at a first position. In response to determining that the optical signature is present in the optical image captured at block 1202, the RF imaging device 100 at block 1208 defines that the first position of the RF imaging device is a reference position. The RF imaging device 100 at block 1210 associates the data representing the first RF image and the first optical image with the reference position. The data representing the first RF and optical images associated with the reference position may be stored in a memory, such as the memory 114.

The RF imaging device 100 at block 1212 detects displacement of the RF imaging device from the reference position. The RF imaging device 100 at block 1214 receives a second RF signal (i.e., reflections of a second RF wave emitted toward a surface) for capturing a second RF image of a portion of the space behind the surface. The RF imaging device 100 determines, at block 1216, a second position at which the second RF signal was captured. The second position is determined based on the reference position and the displacement. The RF imaging device may also capture an optical image of the surface. The RF imaging device 100 then associates the data representing the second RF image and the data representing the second optical image with the second position at block 1218. The data representing the second RF and optical images may be stored in the memory in association with the position data representing the second position.

Figure 13:
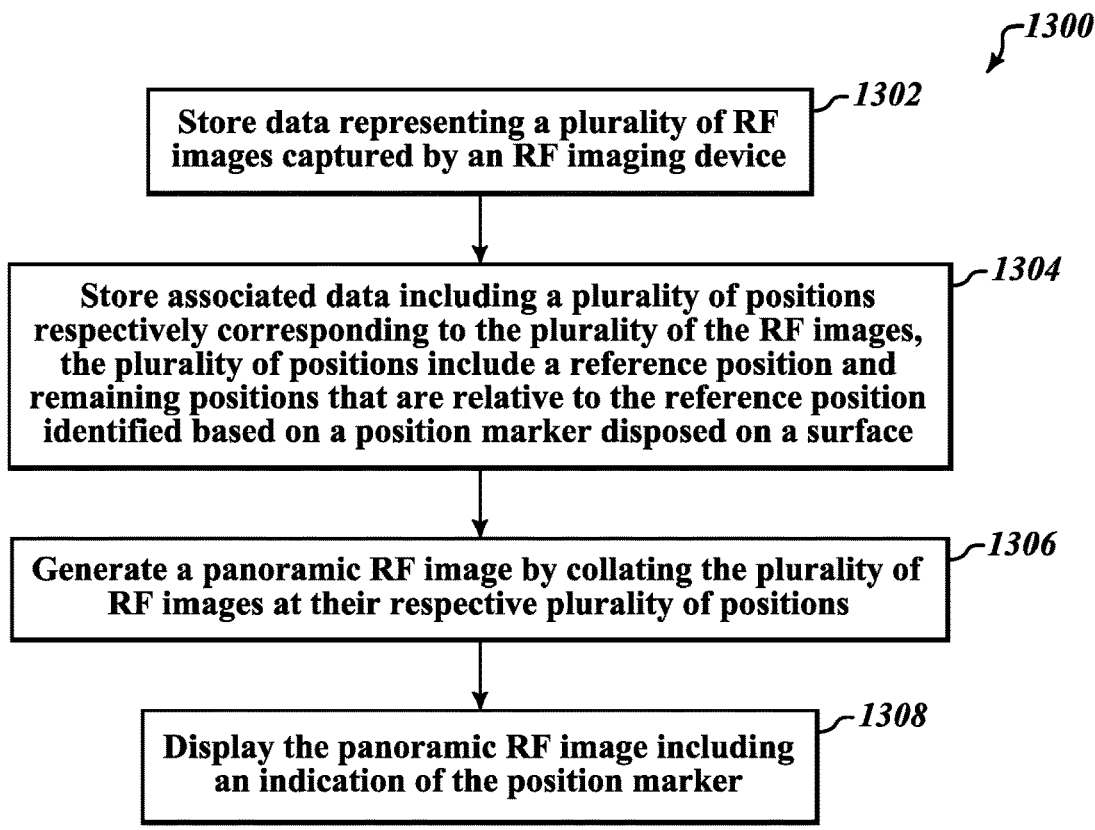
FIG. 13 shows a flow diagram of a method for generating and displaying a panoramic RF image.

FIG. 13 shows a flow diagram of a method for generating and displaying a panoramic RF image. In the method shown, an RF imaging device, such as the RF imaging device 100, stores, at block 1302, data representing a plurality of RF images captured by the RF imaging device. The RF imaging device at block 1304 stores associated data including position data representing a plurality of positions respectively corresponding to the plurality of RF images. The plurality of positions includes a reference position and additional positions that are defined relative to the reference position. The reference position in this embodiment is identified based on detection of an optical signature of a position marker disposed on the surface.

At block 1306, the RF imaging device generates a panoramic RF image by collating the plurality of RF images at their respective plurality of positions. Collating the plurality of RF images at the respective plurality of positions at which they were captured may provide a sweeping view of a larger space, or even an entire space, disposed behind the surface as opposed to localized RF images of portions of the space. For example, collating the plurality of images may include "stitching together" the images in accordance with respective plurality of positions at which they were captured. The panoramic RF image and the panoramic optical image are combined (e.g., blended or superposed) to produce the panoramic composite image.

At block 1308, the RF imaging device displays the panoramic RF image, including an indication of the position marker. It is noted that in various embodiments, the RF imaging device may send the panoramic RF image to a display device, such as a projector or a display screen, and the display device may display the panoramic RF image. Alternatively or in addition, the RF imaging device may send the panoramic RF image to another device, e.g., by wired or wireless transmission, for displaying the panoramic RF image.

In various embodiments, the reference marker 132 may have a signature that is detectable in the visible light range, IR range, UV range, or RF range. Further, the positioning sensor 106 may a visible light, IR, UV, or RF sensor that senses the signature of the reference marker 132.

In various embodiments, the positioning sensor 106 may be an RF sensor. The reference marker 132 may comprise material that produces an identifiable signature in a reflected signal in the RF range. The reference marker 132 may include a wireless transmitter that actively emits an RF beacon having the signature in the RF range. In other embodiments, the reference marker 132 may be a tag, such as an RFID tag, that passively transmits an RF beacon having the signature in the RF range in response to receiving a transmission-inducing activating signal.

The positioning sensor 106 outputs data representing one or more captured RF signals to the processor 102. The processor 102 evaluates the data to determine whether the signature of the RF beacon is present in the data representing the one or more captured RF signals. If the RF beacon is determined to be present in the data, then a position of the RF imaging device 100 may be deemed as the reference position.

In an embodiment, the RF imaging device 100 may include an ultrasonic sensor (or transducer) that senses a distance between the RF imaging device 100 and ceilings, floors and/or side walls. For example, a position of the RF imaging device 100 relative to a surface, such as a wall, may be determined based on a distance between the RF imaging device 100 and a floor or ceiling and the distance between the RF imaging device 100 to one or more side walls. Alternatively, the RF imaging device 100 may include a laser sensor (or transducer) that senses one or more distances between the RF imaging device 100 and a side wall, ceiling or floor. The one or more distances may be used to determine a position of the RF imaging device 100 relative to the surface.

The RF images captured by the RF imaging device 100 are generally three-dimensional (3D) images depicting a 3D space behind a surface, including objects that are detected in the 3D space, though two-dimensional cross-sections of the space may be produced for display. As will be seen from the following description, embodiments of the RF imaging device 100 include components that provide further techniques for enhancing the visualization and understanding of RF 3D imagery of the space behind a surface. In various embodiments, visualization of the 3D RF imagery is enhanced by combining the RF imagery with one or more additional images captured by an additional, secondary imager within the RF imaging device. One example of a secondary imager is an imager that uses optical sensors, such as an IR sensor 126 and/or a VL sensor 128 as described above in relation to FIG. 1, to capture optical data representing an optical image of the surface.

In some embodiments, such as illustrated in FIG. 9, the RF imaging device 100 may have an RF sensor assembly 122 with a field of view that overlaps the field of view of a VL sensor 128. In other words, the VL sensor 128 images a portion of the surface at a position 230 while the RF sensor assembly 122 images the space behind the surface at the same position 230. This is possible with embodiments of the RF imaging device 100 configured to capture RF image data while the RF imaging device is positioned away from the surface.

Other embodiments of the RF imaging device 100 are configured to capture RF images of the space behind the surface while the RF imaging device is positioned on or close to the surface. Such embodiments where the RF imaging device 100 operates in contact with or nearly in contact with the surface make it difficult to simultaneously capture an RF image and a secondary (e.g., optical) image of the same portion of the surface. Indeed, in some cases, the RF sensor assembly 122 may itself block the field of view of the secondary imager. To address this, the RF imaging device 100 may be constructed such that the secondary imager is offset from the RF sensor assembly 122 so that the field of view of the secondary imager (e.g., the VL sensor 128) and the field of view of the RF sensor assembly 122 are not directed toward the same portion of the surface at the same time.

Figure 14:
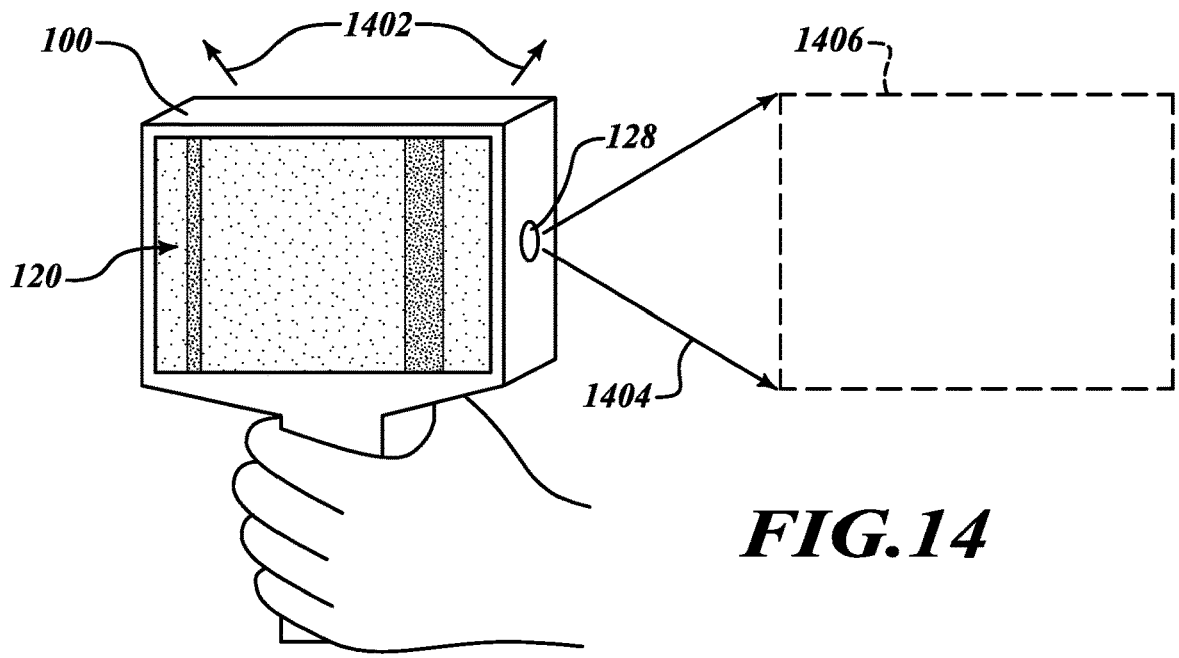
FIG. 14 shows an embodiment of an RF imaging device including an RF sensor assembly having a field of view in accordance with at least one embodiment.

For example, FIG. 14 shows an embodiment of an RF imaging device 100 in which an RF sensor assembly 122 (see FIG. 15) has a field of view toward the surface, e.g., as indicated by the arrows 1402, and captures RF image data representing an RF image of the space behind the surface that is underneath the RF imaging device 100. The RF imaging device 100 includes a VL sensor 128 positioned on a side of the RF imaging device. In this embodiment, the VL sensor 128 has a field of view, e.g., as indicated by the arrows 1404, and captures image data representing a portion of the surface to the side of the RF imaging device 100, as delineated by the dashed lines 1406. Thus the RF sensor assembly 122 and the VL sensor 128 have respective fields of view directed at different portions of the surface.

As discussed earlier, a positioning sensor 106 and/or a displacement sensor 108 operating within the RF imaging device 100 tracks the position and/or movement of the RF imaging device as the RF imaging device scans the surface and captures image data from both the RF sensor assembly 122 and the VL sensor 128 at various positions on the surface. The image data captured by both the RF sensor assembly 122 and the VL sensor 128 may be stored in a memory 114 in association with position data indicating the position relative to the surface at which the respective image data was captured, e.g., as shown and described in relation to FIGS. 3 and 11. With the embodiment of the RF imaging device 100 shown in FIG. 14, the RF image data is stored in the memory 114 in association with position data indicating the position of the RF imaging device 100, since the captured RF image data represents the space directly behind the RF imaging device. The optical image data captured by the VL sensor 128 is also stored in the memory 114, however in association with position data indicating the position of the surface area delineated by the dashed lines 1406. The position of the area delineated by the dashed lines 1406 may be quickly calculated by adjusting the position data of the RF imaging device 100 by a known offset. The offset represents the difference between the area of the surface imaged by the RF sensor assembly 122 and the area of the surface imaged by the VL sensor 128.

Eventually, as the RF imaging device 100 scans the surface and RF and optical image data is captured at various positions relative to the surface, the RF image data and the optical image data may be assembled respectively into a panoramic RF image and a panoramic optical image using the associated position data. In addition, by matching up RF image data and optical image data having the same associated position, a composite image of RF and optical image data may be produced for any position on the surface or for the entire surface.

The embodiment of the RF imaging device 100 in FIG. 14 includes a display screen 120 shown depicting a composite image for the portion of the surface to the side of the RF imaging device delineated by the dashed lines 1406. Assuming that the RF imaging device 100 has been scanning the surface from right to left, the portion of the surface delineated by the dashed lines 1406 was previously imaged by the RF sensor assembly 122 and stored in the memory 114. At the current position of the RF imaging device 100 as shown in FIG. 14, the portion of the surface delineated by the dashed lines 1406 is now within the field of view of the VL sensor 128. The composite image thus shown on the display screen 120 is a combination of the previously-captured RF image of the area 1406 and the optical image of the area 1406 being captured by the VL sensor 128.

Figure 15:
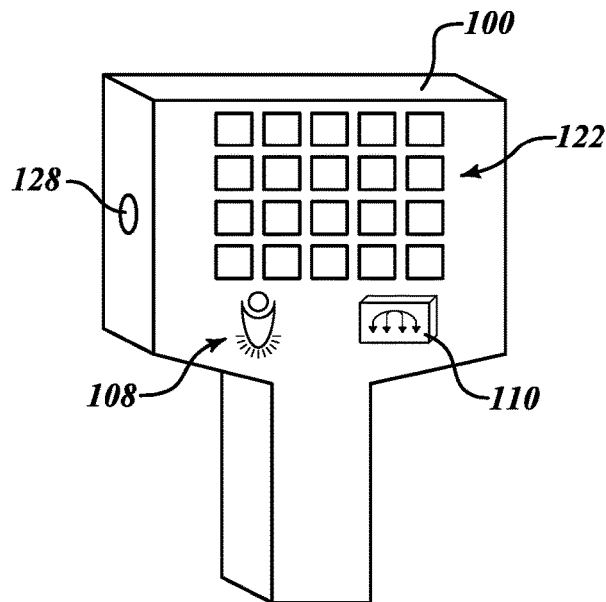
FIG. 15 shows the rear side of the embodiment of the RF imaging device shown in FIG. 14.

FIG. 15 shows the rear side of the embodiment of the RF imaging device 100 shown in FIG. 14. As described earlier, the RF sensor assembly 122 of the RF imaging device 100 may include a plurality of RF sensors arranged in a matrix, e.g., a two-dimensional matrix as illustrated in FIG. 15. The RF sensor assembly 100 further includes a displacement sensor 108 shown in FIG. 15 as an optoelectronic sensor. The optoelectronic sensor 108 may include a light emitting portion and a light receiving portion similar to an optoelectronic sensor used in an optical computer mouse. When the RF imaging device 100 is brought near to or placed in contact with the surface and moved along the surface, the light emitting portion illuminates a small portion of the surface. A reflection of this light is sensed by the light receiving portion, and movement of the RF imaging device 100 along the surface is detected as surface texture or other surface features within the illuminated portion of the surface are detected as moving through the field of view of the optoelectronic sensor 108.

The RF imaging device 100 shown in FIG. 15 further includes a tilt sensor 110, which in various embodiments may be a single axial or multi-axial gyroscope or accelerometer. As described earlier, the tilt sensor 110 detects an orientation of the RF imaging device 100 and outputs data representing the detected orientation to a processor 102 operating within the RF imaging device. If the data received from the tilt sensor 110 indicates that the RF imaging device was titled differently for different RF or optical images, the processor 102 may adjust the image data in the RF or optical images so that all of the images have a common orientation.

Accordingly, with the embodiment of the RF imaging device 100 in FIGS. 14 and 15, composite images that include RF images and optical images of the same areas of a surface can be produced as long as the relative positions and orientations of the RF and optical images are known over time as the device is moved over the surface and the RF and optical image data is obtained. The position data respectively associated with the RF and optical image data is used to map the RF and optical image onto a common coordinate plane. With this mapped data, a panoramic composite image including the obtained RF and optical data may be built up over time as the surface is scanned. Users of the RF imaging device 100 intuitively understand the meaning of RF images at any position on the surface because, in the resulting composite image, optical images corresponding to the same position are superposed on the RF images (or vice versa).

Figure 16:
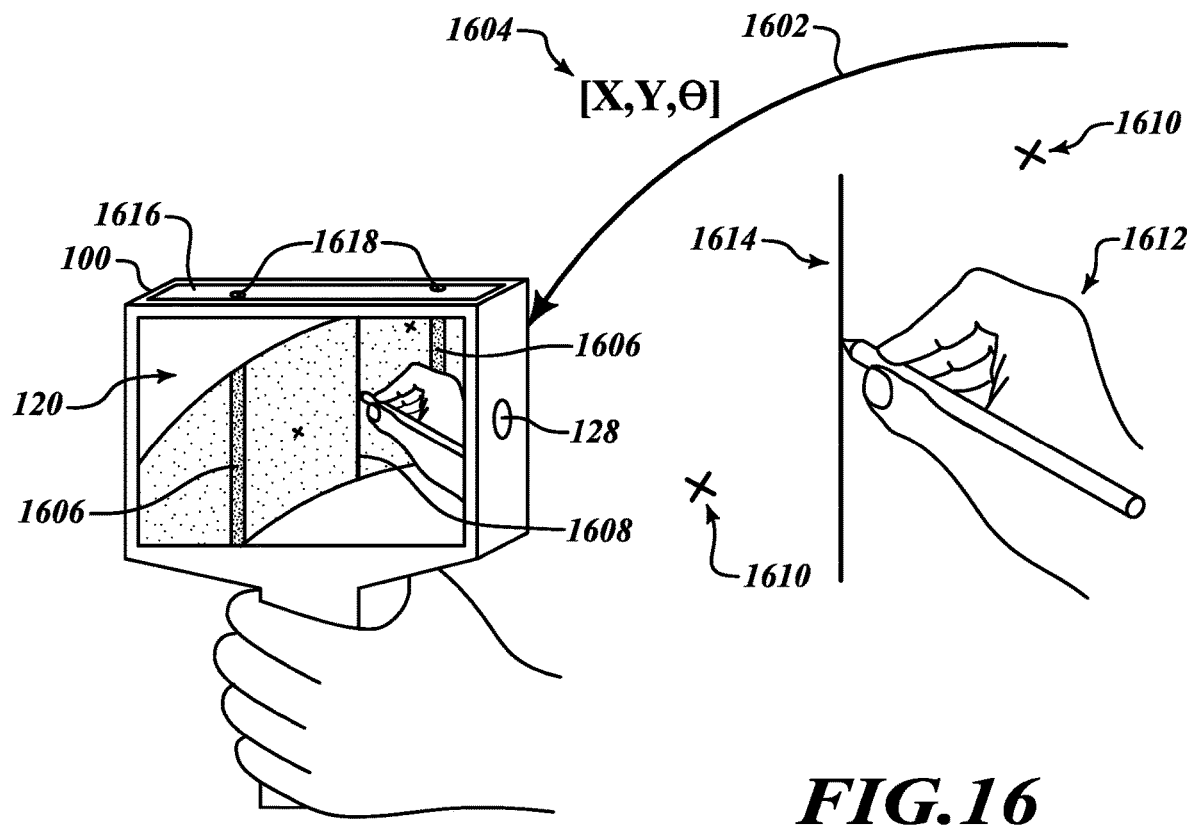
FIG. 16 shows surface scanning by the RF imaging device.
Figure 17:
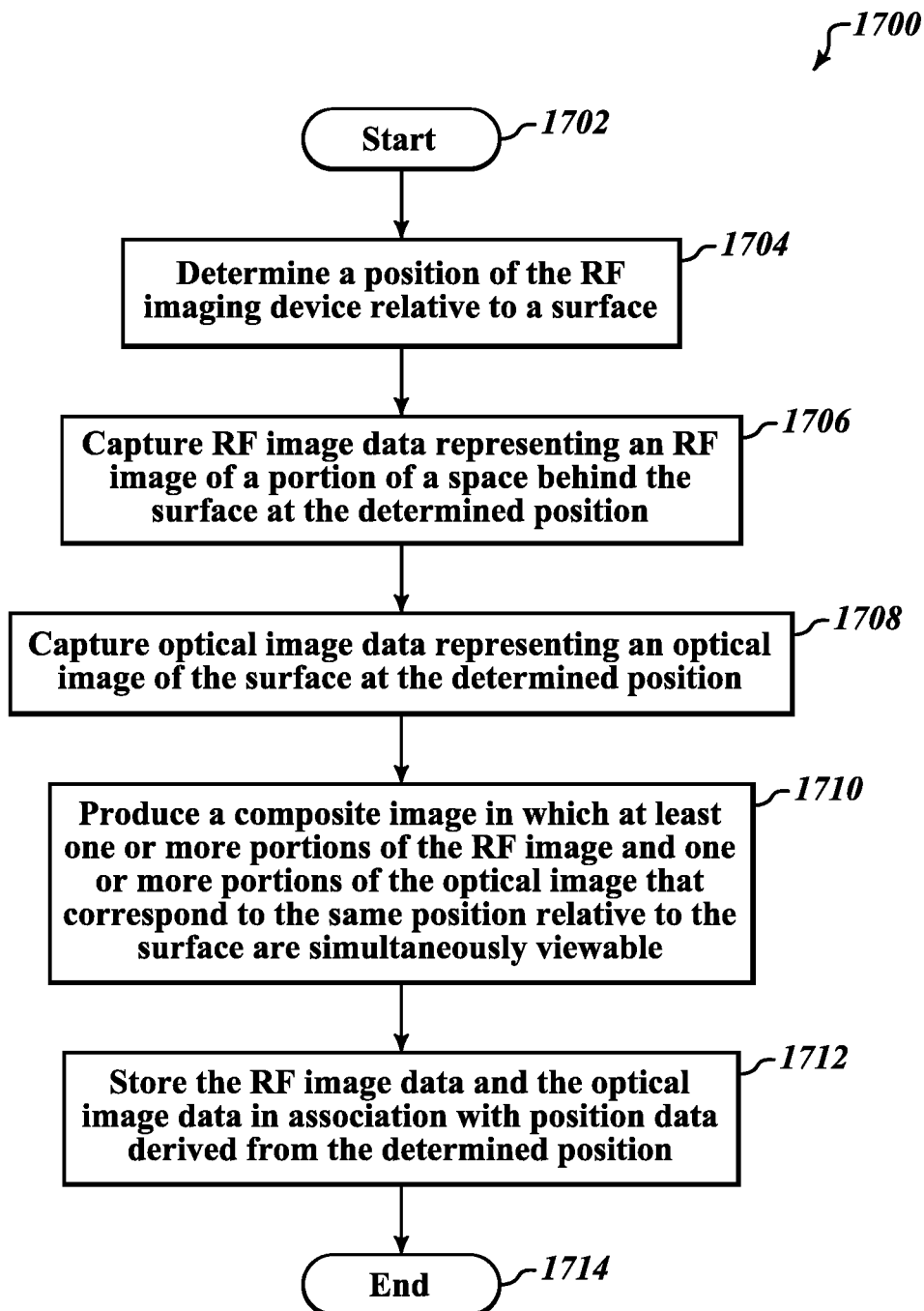
FIGS. 17-21, 23 and 24 show various methods of operation of the RF imaging device.

Furthermore, with the embodiment shown in FIG. 14, the secondary (VL) image included in the composite image shown on the display screen 120 may be a live image of the area to the side of the RF imaging device 100. Accordingly, as shown in FIG. 16, a user of the RF imaging device 100 may place markings (e.g., stickers, pencil marks, tape, etc.) on the surface within the area delineated by the dashed lines 1406 and see a superposition of the marked surface with the RF image for that area in real time, as the markings are applied. The user is therefore able to mark the surface indicating the location of objects of interest (such as pipes, cables, etc.) disposed in the space behind the surface as detected in the RF image.

With the embodiment of the RF imaging device 100 shown in FIG. 16, it is assumed that the RF imaging device 100 has scanned the surface in the direction indicated by the arrow 1602. In the process of scanning the surface, at various positions along the arrow 1602, the RF imaging device 100 captures and stores RF images of the space behind the surface in association with position and tilt data 1604 representing the various positions and orientations of the RF imaging device 100 when the RF images were obtained. The RF imaging device 100 also captures optical images of the surface to the side of the RF imaging device, as previously described with the embodiment in FIGS. 14 and 15. The RF imaging device 100 obtains the RF and optical images at a frame rate determined by the RF sensor assembly 122 and the VL sensor 128 in the device 100. The display screen 120 thereafter is able to display a composite image that includes an optical image of the area to the side of the RF imaging device (which may be a live optical image) superposed with RF image data from one or more previously-captured RF images that correspond to the same area of the surface that is shown in the optical image.

As illustrated in FIG. 16, the composite image on the display screen 120 includes RF imagery of objects 1606, such as pipes, conduits, studs, etc., behind the surface, between which another object 1608, such as an electrical wire, is disposed. For context, pre-existing surface markings 1610 in the field of view of the VL sensor 128 are also visible in the composite image. As a hand 1612 of a user enters the field of view of the VL sensor 128, the user's hand similarly becomes visible in the composite image on the display screen 120. The user is able to see their hand 1612 positioned on the surface at the same position as the object 1608 that is disposed in the space behind the surface. With this real-time visual feedback, the user is able to mark the surface with a line 1614 approximately in line with the position of the object 1608 behind the surface. The user is then able to take action with respect to the surface (e.g., cutting a hole in the surface) at a particular position knowing what object or objects are disposed in the space behind the surface at that position.

The RF imaging device shown in FIG. 16 includes an additional feature that may help a user of the RF imaging device to recognize and appreciate the relative depth of objects detected in the 3D space behind the surface. In FIG. 16, the display screen 120 is a primary display screen. The RF imaging device 100 further includes a secondary display screen 1616 disposed on a side surface of the device, such as the top side surface of the device. With this embodiment of the RF imaging device 100, the processor in the RF imaging device is further configured to produce an RF cross-sectional image of a plane in the space behind the area of the surface. The RF cross-sectional image is oriented at an angle with respect to the RF image represented by the RF image data in the composite image displayed by the primary display screen 120. The RF cross-sectional image as displayed in the secondary display screen 1616 includes cross-sectional views 1618 of the objects 1606 that are otherwise shown in the primary display screen 120. An advantage of the cross-sectional view provided in the secondary display screen 1616 is that the relative depth of each of the objects 1606 in the 3D space behind the surface is depicted by the relative position of the cross-sectional views 1618 in the secondary display screen 1616.

In some embodiments, the secondary display screen 1616 is physically oriented on the RF imaging device 100 at an angle with respect to the primary display screen 120 that approximates the angle between the RF cross-sectional image displayed by the secondary display screen 1616 and the RF image in the composite image displayed by the primary display screen 120. By physically orienting the secondary display screen 1616 at an angle with respect to the primary display screen 120 in this manner, a user of the RF imaging device is better able to appreciate the relative angle between the RF cross-sectional image in the secondary display screen 1616 and the RF image in the primary display screen 120. With the embodiment shown in FIG. 16, the secondary display screen 1616 is physically oriented at a right angle to the primary display screen 120. Consequently, with this embodiment, the RF cross-sectional image in the secondary display screen 1616 is normal to the RF image included in the composite image shown in the primary display screen 120.

While FIG. 16 illustrates an embodiment in which the secondary display screen 1616 is located on the top side of the RF imaging device, in other embodiments, the secondary display screen 1616 may be located on the left side, right side, or bottom side, of the RF imaging device. Locating the secondary display screen 1616 on a left, right, or bottom side surface may be advantageous in situations where a user of the RF imaging device is holding the device on the wall surface above his or her head. Yet further embodiments of the RF imaging device 100 may include multiple secondary display screens 1616 located on multiple side surfaces of the RF imaging device, with each secondary display screen 1616 showing an RF cross-sectional image of a plane in the space behind the wall surface. In still further embodiments, one or more secondary display screens 1616 may depict a three-dimensional image of the space behind the surface, preferably with an orientation that matches the orientation of the secondary display screen 1616 relative to the primary display screen 120.

Other embodiments of the RF imaging device 100 may be configured to display only the RF image (not a composite image) on the primary display screen 120 while displaying an RF cross-sectional image on the secondary display screen 1616. As with the previous embodiments, the RF cross-sectional image on the secondary display screen 1616 may be at an angle, such as a right angle, to the plane of the RF image displayed in the primary display screen 120.

In yet further embodiments, the RF imaging device 100 may have a single physical display screen, in which a first area or region of the display screen may depict an image of the space behind the surface (e.g., as described above for the primary display screen), and a second area or region of the display screen may depict a cross-sectional image (e.g., as described above for the secondary display screen). In other words, different views of the RF image may be shown by primary and secondary "display screens" that are implemented as different areas or regions of the same physical display screen.

Embodiments of the RF imaging device 100 as described herein enable various methods of operation of the RF imaging device as shown in FIGS. 17-21. The method 1700 shown in FIG. 17 begins at a starting block 1702. At block 1704, a position sensor in the RF imaging device determines a position of the RF imaging device relative to a surface. As described earlier, position sensing may be accomplished using techniques such as triangulation or time-of-flight or time-of-arrival of RF signals emitted by position sensors at known locations or by detection of optical signatures of position markers placed on the surface.

At block 1706, an RF sensor assembly in the RF imaging device captures RF image data representing an RF image of a portion of the space behind the surface at the determined position of the RF imaging device. At block 1708, an optical sensor in the RF imaging device captures optical image data representing an optical image of the surface at the determined position of the RF imaging device. The RF image at the determined position and the optical image at the determined position may be captured at different times. Thus, the optical image may be captured before, at the same time, or after the RF image is captured.

It should also be recognized that the RF imaging device may be moved to a different position relative to the surface between capturing the RF image data and capturing the optical image data. This may occur, for example, when the field of view of the RF sensor assembly is different than the field of view of the optical sensor in the RF imaging device.

At block 1710, the processor in the RF imaging device produces a composite image in which at least one or more portions of the RF image and one or more portions of the optical image that correspond to the same position relative to the surface are simultaneously viewable. This composite image may be displayed on a display screen of the RF imaging device, or it may be transmitted by the RF imaging device to another device for display. Typically, though optional, the RF imaging device stores the RF image data and the optical image data in a memory in association with position data derived from the determined position of the RF imaging device, as indicated at block 1712. The method 1700 ends at block 1714.

Figure 18:
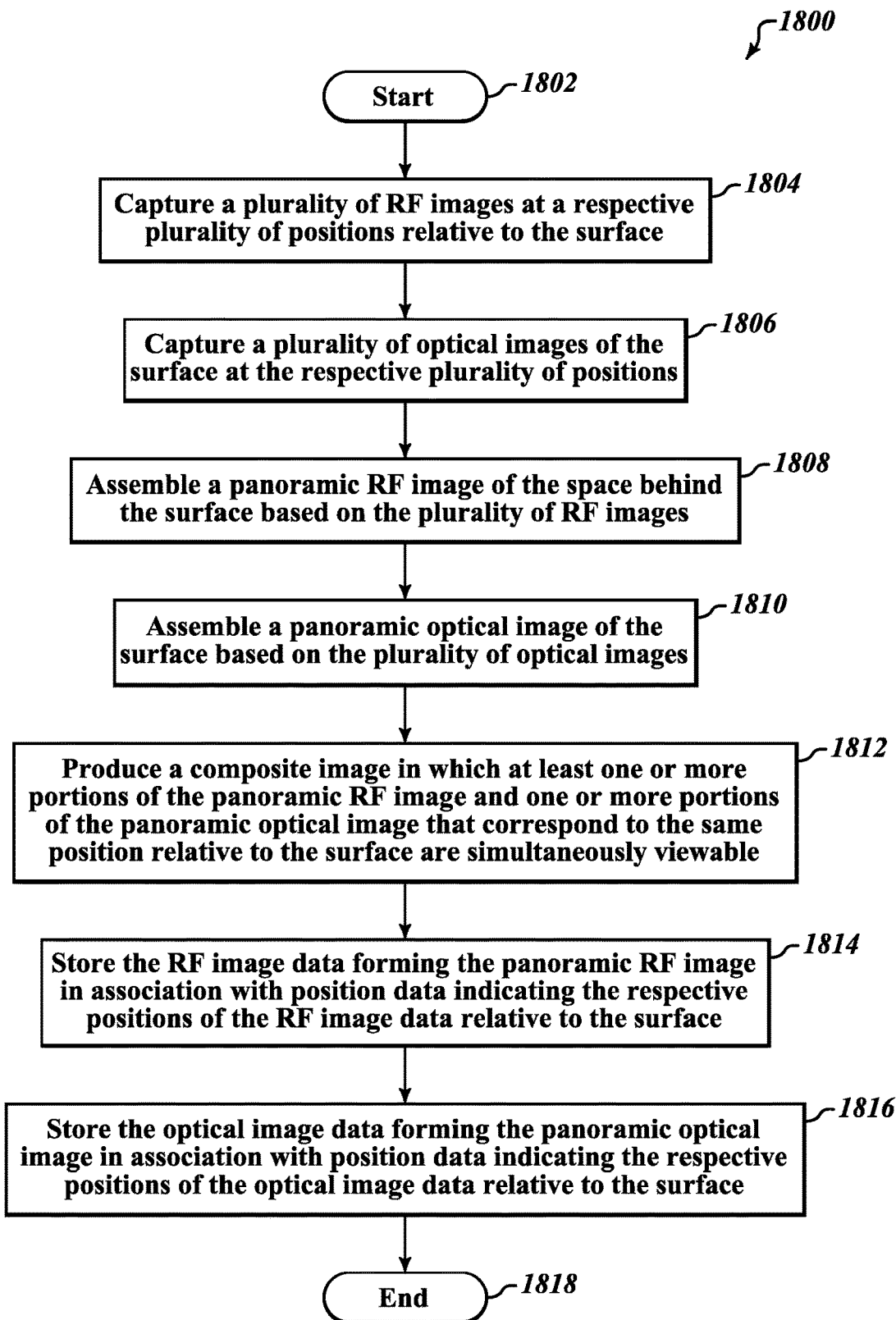

FIG. 18 shows a method 1800 that begins at a starting block 1802. At block 1804, the RF sensor assembly of the RF imaging device captures a plurality of RF images at a respective plurality of positions relative to the surface. Each RF image thus captured is an RF image of a portion of the space behind the surface at the respective plurality of positions.

At block 1806, the optical sensor of the RF imaging device captures a plurality of optical images of the surface at the respective plurality of positions. The plurality of optical images may be captured before, at the same time as, or after the plurality of RF images are captured.

A processor in the RF imaging device is configured, at block 1808, to assemble a panoramic RF image of the space behind the surface based on the plurality of RF images that were captured. The processor is also configured, at block 1810, to assemble a panoramic optical image of the surface based on the plurality of optical images that were captured. The panoramic optical image may be assembled before, at the same time as, or after the panoramic RF image is assembled.

The panoramic RF image may be assembled by collating the plurality of RF images of the space behind the surface at the respective plurality of positions. Collating the plurality of RF images may include, for example, identifying RF image data in the plurality of RF images at different positions relative to the surface and assembling the RF image data at each position of the surface to form the panoramic RF image.

Similarly, the panoramic optical image may be assembled by collating the plurality of optical images of the surface at the respective plurality of positions. Collating the plurality of optical images may include, for example, identifying optical image data in the plurality of optical images at different positions relative to the surface and assembling the optical image data at each position of the surface to form the panoramic optical image.

At block 1812, the processor produces a composite image in which at least one or more portions of the panoramic RF image and one or more portions of the panoramic optical image that correspond to the same position relative to the surface are simultaneously viewable. Optionally, though expected, the processor may store the RF image data forming the panoramic RF image, as indicated at block 1814, in association with position data indicating the respective positions of the RF image data relative to the surface. Likewise, the processor may store the optical image data forming the panoramic optical image in association with position data indicating the respective positions of the optical image data relative to the surface, as indicated at block 1816. At block 1818, the method 1800 ends.

As shown in FIG. 15, the RF imaging device 100 may include a tilt sensor 110 that determines an orientation of the RF imaging device relative to the surface when the RF image data and the optical image data are captured. In various embodiments, the determined orientation specifies a rotation of the respective RF image and optical image about an axis in relation to the surface. The RF image data and the optical image data thereafter are adjusted based on the specified rotation so that the RF image and the optical image have a common orientation relative to the surface.

Figure 19:
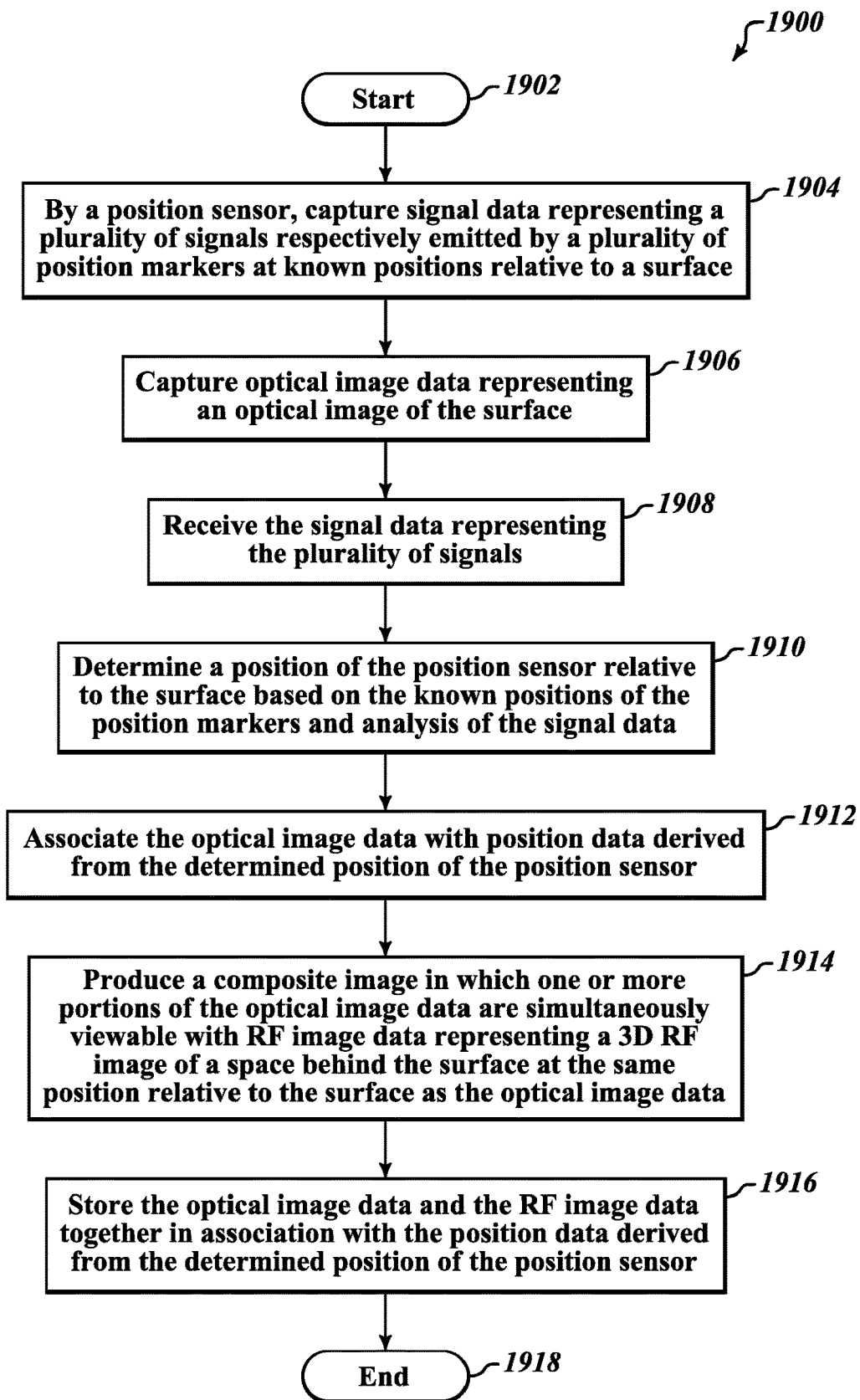

FIG. 19 illustrates a method 1900 that begins at a starting block 1902. At block 1904, the method includes, by a position sensor, capturing signal data representing a plurality of signals respectively emitted by a plurality of position markers at known positions relative to a surface. One or more of the position markers may include an active transmitter that has a power source and is configured to transmit a signal of the plurality of signals to the position sensor. Alternatively or in addition, one or more of the position markers may include a passive transmitter that is induced to transmit a signal of the plurality of signals in response to receiving an activating signal. The position of the position sensor relative to the surface may be determined based on the known positions of the position markers and triangulation of the signal data or a determined time-of-flight or time-of-arrival for each the signals transmitted from the respective position markers. At block 1906, optical image data representing an optical image of the surface is captured by an optical sensor.

At block 1908, a processor in the RF imaging device receives the signal data representing the plurality of signals captured by the position sensor. The processor, at block 1910, determines the position of the position sensor relative to the surface based on the known positions of the position markers and analysis of the signal data. The processor thereafter associates the optical image data with position data that is derived from the determined position of the position sensor, as indicated at block 1912.

With the optical image data and associated position data in hand, the processor produces a composite image, as indicated at block 1914, in which one or more portions of the optical image data are simultaneously viewable with RF image data representing a three-dimensional (3D) RF image of the space behind the surface at the same position relative to the surface as the optical image data. The 3D RF image data may have been previously captured by the RF imaging device and stored with associated position data, or received by the RF imaging device from another RF imaging device or data source. The optical image data and the RF image data may also be stored in a memory in association with the position data derived from the determined position of the position sensor, as indicated at block 1916. Furthermore, the RF imaging device may comprise a communication interface that is configured to transmit the composite image to a receiving device.

In some cases, the optical sensor captures optical image data representing a plurality of optical images of the surface at a respective plurality of positions. The processor of the RF imaging device is configured to assemble a panoramic optical image of the surface based on the optical image data representing the plurality of optical images. The optical image data in the panoramic optical image is associated with position data derived from determined positions of the position sensor corresponding to when the optical image data was captured. A composite image may be produced in which at least one or more portions of the optical image data in the panoramic optical image are simultaneously viewable with RF image data representing a 3D RF image of the space behind the surface captured at the same position as the optical image data, based on the position data associated with the one or more portions of the optical image data.

Figure 20:
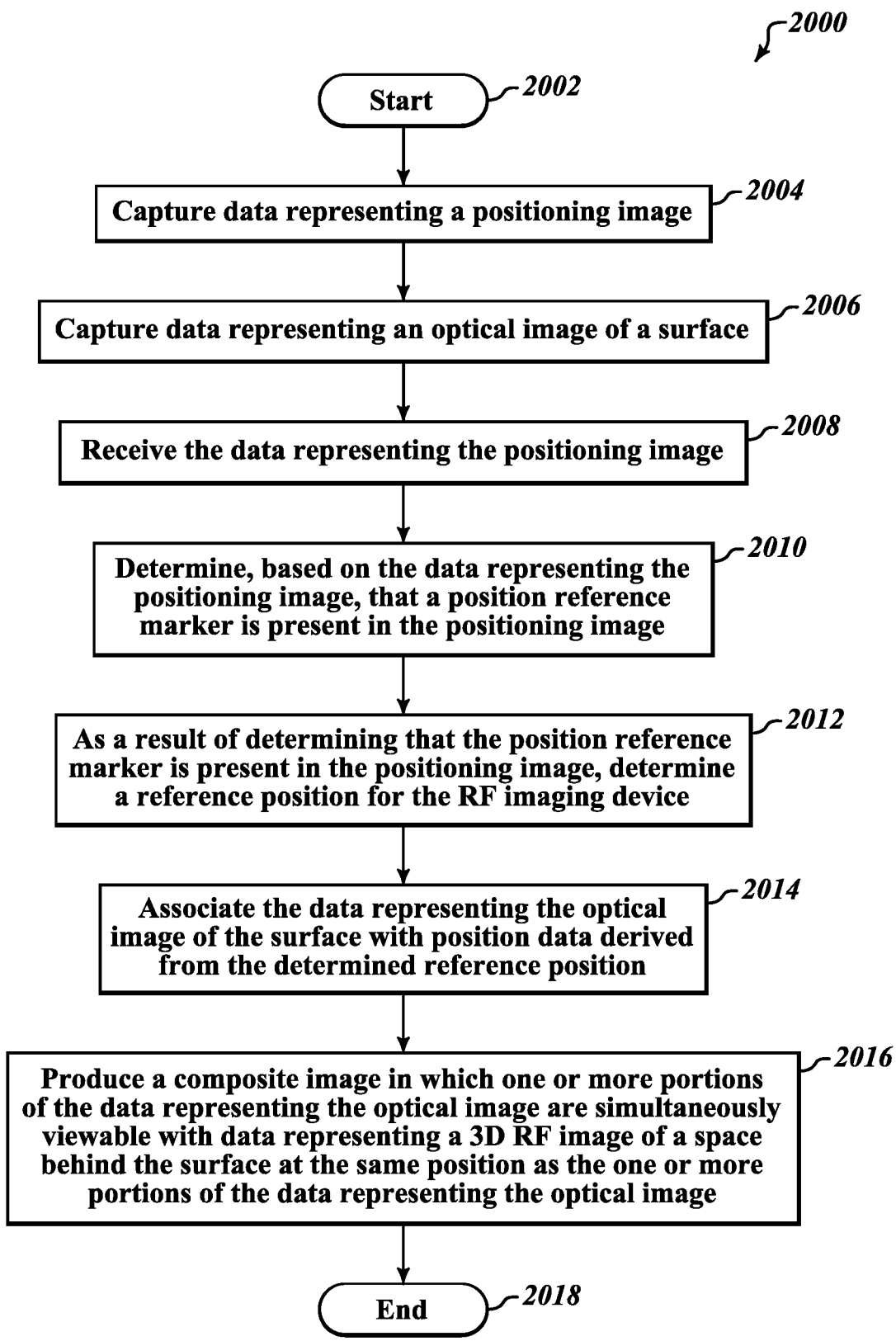

FIG. 20 shows a method 2000 that begins at a starting block 2002. At block 2004, a position sensor in the RF imaging device captures data representing a positioning image, and at block 2006, an optical sensor captures data representing an optical image of a surface. A processor operatively coupled to the position sensor and the optical sensor receives the data representing the positioning image, as indicated at block 2008, and determines, based on the data representing the positioning image, that a position reference marker is present in the positioning image, as indicated at block 2010. As a result of determining that a position reference marker is present in the positioning image, at block 2012 the processor determines a reference position for the RF imaging device. The data representing the optical image of the surface is associated at block 2014 with position data derived from the determined reference position of the RF imaging device. As with previous methods described herein, at block 2016, a composite image may thereafter be produced in which one or more portions of the data representing the optical image are simultaneously viewable with data representing a 3D RF image of the space behind the surface at the same position as the one or more positions of the data representing the optical image, based on the position data associated with the one or more portions of the data representing the optical image. The method 2000 thereafter ends at block 2018.

Figure 21:
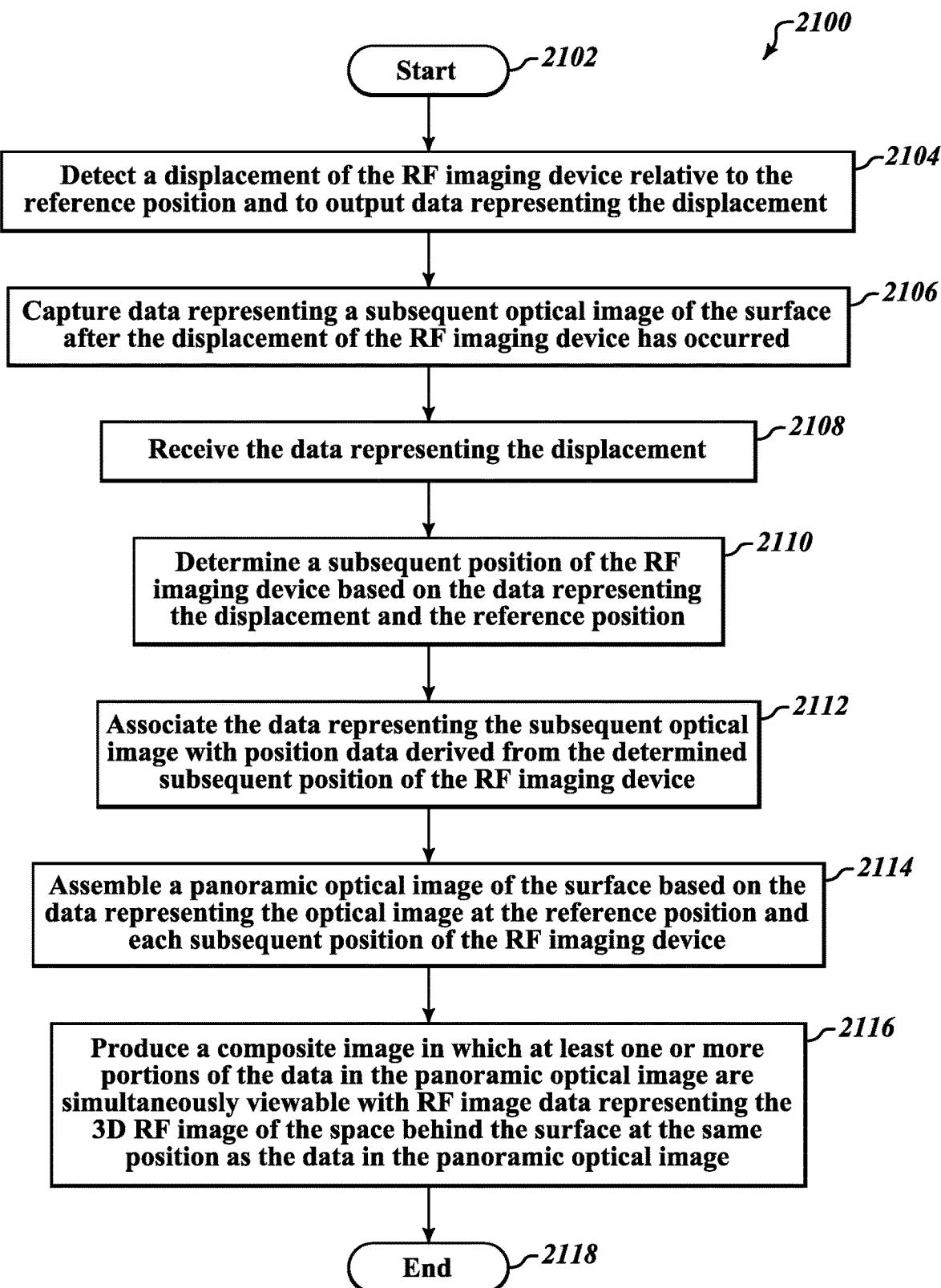

FIG. 21 shows a method 2100 that begins at a starting block 2102. At block 2104, the RF imaging device uses a displacement sensor to detect a displacement of the RF imaging device relative to the reference position (e.g., as determined at block 2012 in FIG. 20) and to output data representing the displacement. At block 2106, an optical sensor captures data representing a subsequent optical image of the surface after displacement of the RF imaging device has occurred (i.e., the RF imaging device has moved). At block 2108, the processor in the RF imaging device is configured to receive the data representing the displacement, and at block 2110, the processor determines a subsequent position of the RF imaging device based on the data representing the displacement and the reference position. Thereafter, at block 2112, the processor associates the data representing the subsequent optical image with position data derived from the determined subsequent position of the RF imaging device.

The RF imaging device may further be configured to assemble a panoramic optical image of the surface, as indicated at block 2114, based on the data representing the optical image at the reference position and each subsequent position of the RF imaging device. The data in the panoramic optical image is associated with position data derived from the reference position or a subsequent position of the RF imaging device corresponding to when the data representing the optical image or the subsequent optical image was captured. A composite image may thereafter be produced as indicated at block 2116, in which at least one or more portions of the data in the panoramic optical image are simultaneously viewable with RF image data representing the 3D RF image of the space behind the surface at the same position as the data in the panoramic optical image. This is accomplished based on the position data associated with the one or more portions of the data in the panoramic optical image.

It should be recognized that further variations and embodiments of the RF imaging device are possible. For example, while the RF imaging device 100 shown in FIGS. 14-16 has a VL sensor 128 (e.g., a VL camera) on the right-hand side of the device with a field of view pointed toward the surface, other embodiments of the RF imaging device may have the VL camera aimed out from any direction (top, left, right, or bottom of the RF imaging device). Also, the RF imaging device may include multiple VL cameras with fields of view simultaneously pointed at the surface in different directions. Multiple display screens may display multiple composite images based on combinations of RF image data and the optical image data from the respective VL cameras.

The RF imaging device 100 described above in relation to FIG. 15 utilizes a displacement sensor 108 that detects motion along the surface using an optoelectronic device. Other embodiments of the RF imaging device may use other motion tracking devices, such as an inertial sensor, to detect displacement of the device. In these embodiments and yet other embodiments, triangulation of the position of the RF imaging device may be determined using multiple external transmitters and an internal receiver.

Moreover, embodiments of the RF imaging device 100 described above employ a VL sensor 128 that is offset from, and does not share the same field of view as, the RF sensor assembly 122. Alternatively, the VL sensor 128 may be arranged coincident with (and share the same field of view of) the RF sensor assembly 122.

Additional embodiments of the RF imaging device 100 may include or provide for visualization of RF imagery of a space behind the surface by projection of the RF imagery onto the surface from which the RF imagery was captured. In such embodiments, a panoramic RF image is generated from RF image data captured by one or more previous scans of the surface using an RF imaging device. While scanning the surface, RF image data representing a three-dimensional (3D) RF image of the space behind the surface is obtained by the RF imaging device 100. The RF image data is assembled into the panoramic RF image. With corresponding position and orientation data relating to the RF imaging device and the conditions under which the RF image data was captured, appropriate mapping, shifting, and/or scaling of the RF image data may be performed when the composite image is produced.

Figure 22:
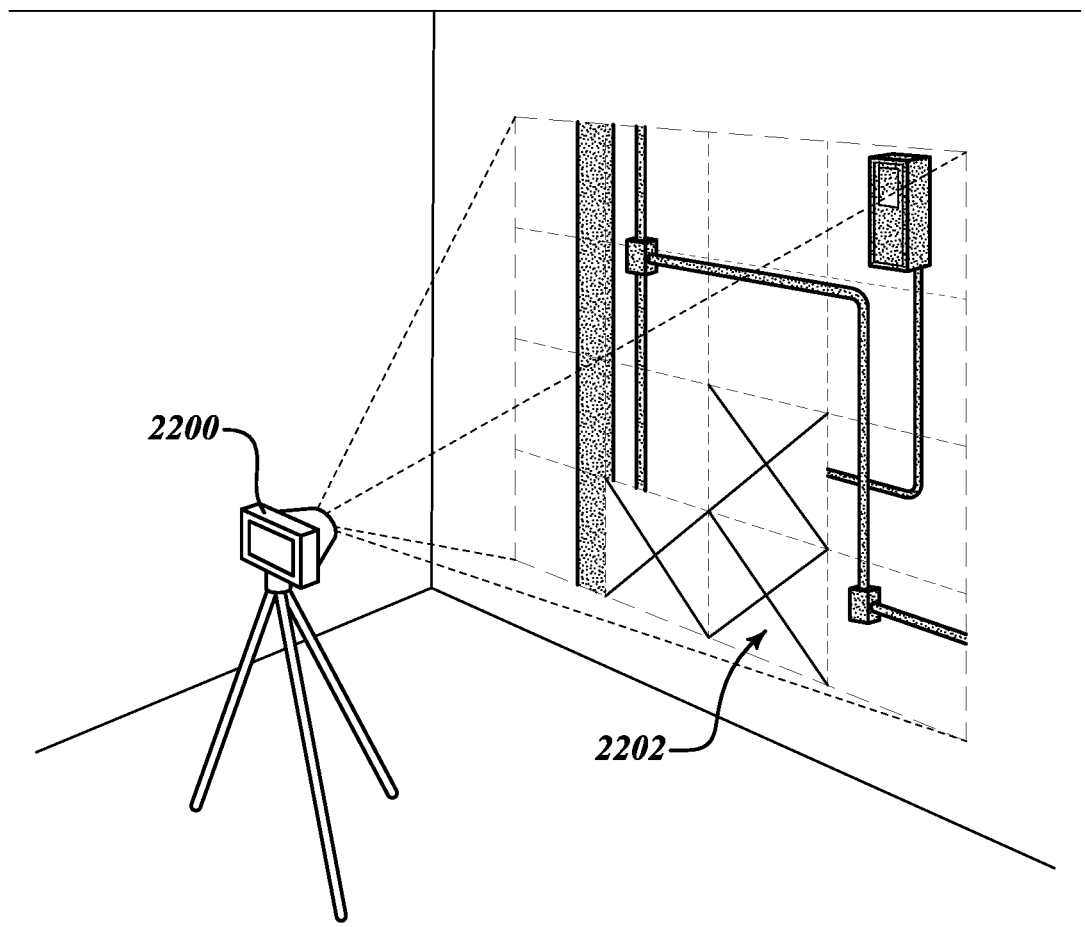
FIG. 22 shows the panoramic RF image projected onto the surface using a projector.

As shown in FIG. 22, the panoramic RF image may be projected onto the surface using a projector 2200. If there are portions of the surface that were not scanned by the RF imaging device, the panoramic RF image may so indicate by one or more notations 2202 in the particular portions of the surface that were not scanned. The projected panoramic RF image provides a user with an intuitive representation of the objects disposed in the space behind the surface. If desired, the user may mark directly on the surface (e.g., using a pencil, tape, stickers, etc.) while the projected image is displayed, to indicate the positions of objects (such as pipes, wires, etc.) within the space behind the surface.

For proper projection of the panoramic RF image onto the surface, the RF image data should be correctly registered (i.e., positioned, shifted, and scaled as needed) with the surface so that the projected objects in the RF image are aligned with the actual objects disposed within the 3D space behind the surface. One method for correct registration of the image data includes capturing RF and VL image data with position and orientation information, and providing a registered panoramic image from both the RF and optical imagers of RF imaging device. A VL imager is also incorporated into the projector 2200. The previously-captured VL panoramic image data is registered (i.e., correlated) with a live VL image obtained by the VL imager in the projector 2200 using known image processing techniques. Because the stored RF image data has been registered to match the stored VL image data, the panoramic RF image will be appropriately registered (i.e., position, shifted, and scaled) for projection onto the surface.

Another method for correct registration of the image data includes capturing RF and VL image data with position and orientation information, and providing a registered panoramic image from both the RF and optical imagers of the RF imaging device. As with the previous method, a VL imager is also incorporated into the projector 2200. The previously-captured panoramic VL image is projected from the projector onto the surface. A user thereafter manually adjusts the projected VL image (i.e., positions, shifts, and/or scales the projected VL image) using reference marks or other features on the surface that are also shown in the projected VL image, until the projected VL image is aligned with the actual reference marks or other features visible on the surface. The user may then select an RF image, or a composite RF/optical image, for projection by the projector 2200. Because the stored RF image has been registered to match the stored VL image, which was manually adjusted, the projected RF image or composite image will also automatically be adjusted and appear appropriately registered with the actual surface.

Yet another method for correct registration of the image data includes acquiring absolute positioning data along with the previously-captured RF image data. A combination of sensors within the projector 2200 are used to determine the position and orientation of the projector relative to the surface (e.g., using one or more laser range finders, tilt sensors, triangulation from position reference markers at known locations, etc.), and the previously-captured RF image data is automatically adjusted (i.e., positioned, scaled, and/or shifted) according to the determined position and orientation of the projector for correct projection of the RF image or composite image onto the surface.

Figure 23:
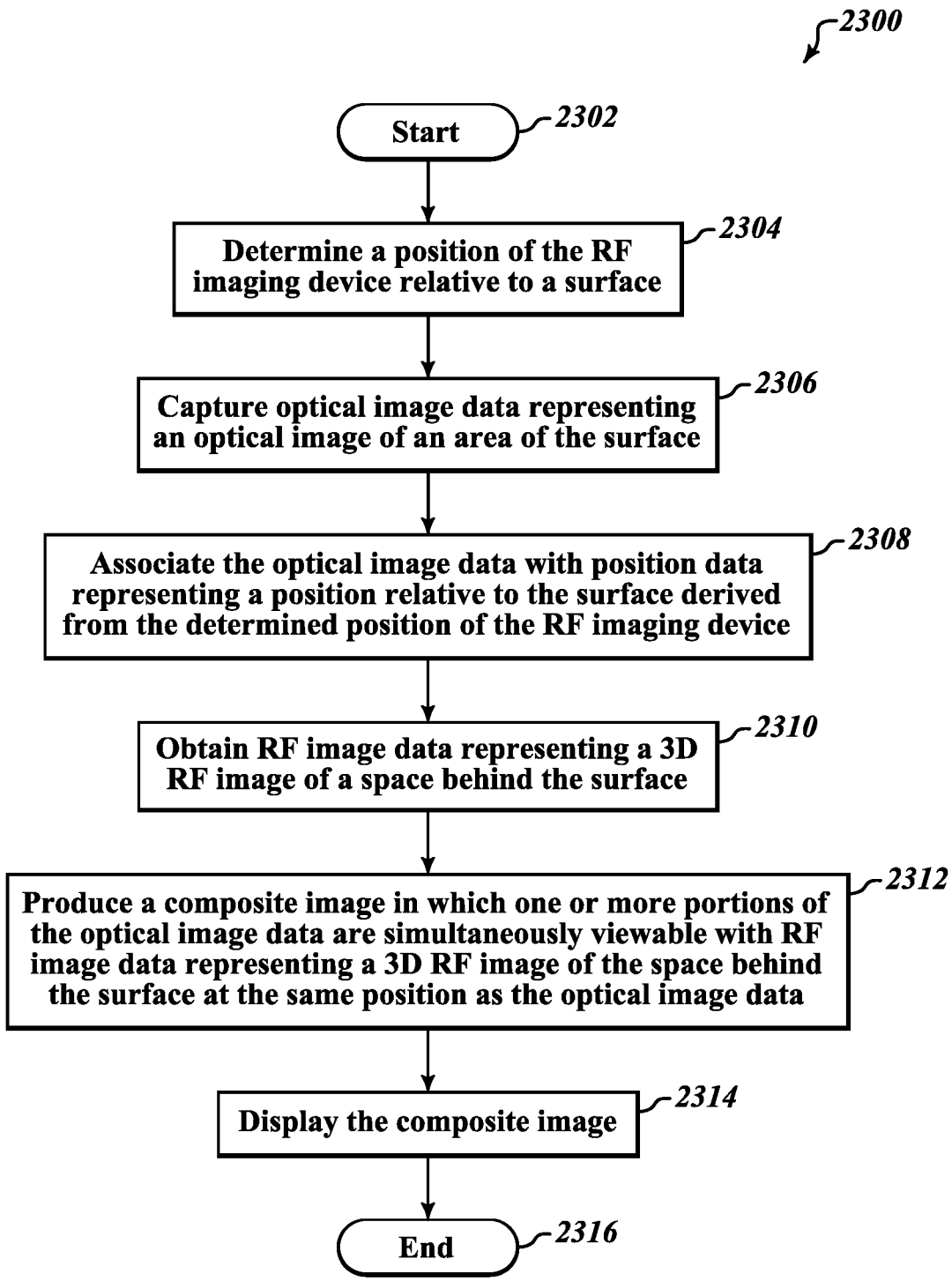

FIG. 23 shows a method 2300 that includes some elements similar to other method elements previously described herein. The method 2300 begins at a starting block 2302. At block 2304, a position sensor in an RF imaging device determines a position of the RF imaging device relative to a surface. At block 2306, an optical sensor captures optical image data representing an optical image of an area of the surface. At block 2308, the captured optical image data is associated with position data representing a position relative to the surface derived from the determined position of the RF imaging device. The derived position data corresponds to the area of the surface imaged by the optical sensor. At block 2310, the RF imaging device obtains RF image data representing a 3D image of the space behind the surface. The RF imaging device may obtain the RF image data by scanning the surface with its own RF sensor assembly, or if the RF imaging device does not have an RF sensor assembly (i.e., the RF imaging device is capable of displaying RF image data but not generating RF image data), the RF imaging device may obtain the RF image data from another RF imaging device or a remote data source that does have an RF sensor assembly. In some cases, the RF imaging device without RF sensors obtains the RF image data from another RF imaging device or from a remote data source by wireless communication using a communication interface in the RF imaging device.

A processor in the RF imaging device is configured to produce a composite image in which one or more portions of the optical image data are simultaneously viewable with RF image data representing a 3D RF image of the space behind the surface at the same position as the optical image data, as indicated at block 2312. Thereafter, at block 2314, the composite image is displayed. For example, the composite image may be shown on a display screen of the RF imaging device. Alternatively or in addition, the composite image may be projected by a projector, such as the projector 2200 described in relation to FIG. 22, onto a surface such as the surface scanned by the RF imaging device. The method 2300 ends at block 2316.

As with previous embodiments described herein, the RF imaging device may further comprise an RF sensor assembly configured to capture RF image data representing the 3D RF image of the space behind the surface. At a given time, the RF sensor assembly may image the space behind an area of the surface that is different than the area of the surface imaged by the optical sensor. In some cases, the optical sensor may be disposed on a side of the RF imaging device and the area of the surface imaged by the optical sensor is an area of the surface to the side of the RF imaging device, as described in relation to FIG. 14. The RF imaging device may also comprise a memory in which the RF image data is stored in association with position data representing one or more positions relative to the surface where the space behind the surface was imaged by the RF sensor assembly.

In some embodiments, the optical image data in the composite image may be real-time optical image data captured by the optical sensor while the RF image data in the composite image includes previously-captured RF image data. The optical image of the area of the surface may include an image of a real-time physical marking of the surface in the area of the surface, as described in relation to FIG. 16.

The position data associated with the optical image data may represent the same position relative to the surface as the determined position of the RF imaging device. In other embodiments, the position data associated with the optical image data represents a position relative to the surface that is different than the determined position of the RF imaging device.

The RF image data in the composite image may be obtained from a panoramic RF image of the space behind the surface that is comprised of previously-captured RF image data assembled into the panoramic RF image.

Alternatively, or in addition, the RF imaging device may comprise multiple optical sensors that are configured to capture optical image data representing optical images of different areas of the surface. The optical image data for each area of the surface is associated with position data representing a position relative to the surface derived from the determined position of the RF imaging device. The derived position data corresponds to each respective area of the surface imaged by the multiple optical sensors.

According to yet another embodiment of an RF imaging device, the RF imaging device may include a memory in which optical image data and RF image data are stored, wherein the optical image data represents an optical image of a surface and the RF image data represents an RF image of a space behind the surface, and wherein the optical image data and the RF image data are respectively associated in the memory with position data representing one or more positions relative to the surface. With this embodiment, the RF imaging device may also include an output configured to provide an image display along with a processor that is operatively coupled to the memory and the output. The processor is configured to produce at least one image for display based on one or more portions of the RF image data that are selected and retrieved from the memory based on a specified position relative to the surface, and to provide the produced image to the output for display.

As described above, the output may comprise a projector (e.g., as shown in FIG. 22) that projects the produced image for display on the surface. The specified position for selection of the RF image data may be determined based on a projection, by the projector, of an optical image of the surface based on optical image data in the memory and a determined field of projection of the projector relative to the surface. The projection of the optical image is adjusted so that features on the surface in the projected optical image line up with the same features presently on the surface, after which the field of projection of the projector is determined based at least in part on a position and orientation of the RF imaging device relative to the surface. The position and orientation of the RF imaging device are determined based at least in part on a known scale of the projected optical image having features in the image that line up with the same features presently on the surface.

The RF imaging device may further comprise an optical sensor configured to capture optical image data representing a real-time optical image of the surface, wherein the optical image projected by the projector is based on the optical image data captured in real time by the optical sensor. The position of the RF imaging device relative to the surface may be determined based on a determination that a position reference marker is present in the real-time optical image projected by the projector. The position reference marker indicates a unique position on the surface that is usable by the RF imaging device to determine the position of the RF imaging device relative to the surface. The orientation of the RF imaging device relative to the surface may be determined based on at least one distance parameter obtained from a range sensor and at least one tilt parameter obtained from a tilt sensor that are operatively coupled to or incorporated into the RF imaging device.

Alternatively, the specified position for selection of the RF image data may be determined based on a determined field of projection of the projector relative to the surface, wherein the field of projection of the projector is determined based at least in part on a position and orientation of the RF imaging device relative to the surface, and wherein the position of the RF imaging device relative to the surface is determined based on triangulation of a plurality of signals received by the RF imaging device from a plurality of position markers at known positions relative to the surface. The orientation of the RF imaging device relative to the surface may be determined based on at least one distance parameter obtained from a range sensor and at least one tilt parameter obtained from a tilt sensor that are operatively coupled to or incorporated into the RF imaging device.

With yet another alternative, the specified position for selection of the RF image data may be determined based on a determined field of projection of the projector relative to the surface, wherein the field of projection of the projector is determined based at least in part on a position and orientation of the RF imaging device relative to the surface, and wherein the position of the RF imaging device relative to the surface is determined based on a time-of-flight for a plurality of signals received by the RF imaging device from a plurality of position markers at known positions relative to the surface. As with previous alternatives, the orientation of the RF imaging device relative to the surface may be determined based on at least one distance parameter obtained from a range sensor and at least one tilt parameter obtained from a tilt sensor that are operatively coupled to or incorporated into the RF imaging device.

Still another embodiment of the RF imaging device includes an optical sensor that is configured to capture optical image data representing a real-time optical image of the surface. The specified position for selection of the RF image data is determined based at least in part on a determined position and orientation of the RF imaging device relative to the surface. The position of the RF imaging device relative to the surface is determined based on a known field of view of the optical sensor and a determination that a position reference marker is present in the real-time optical image. The position reference marker indicates a unique position on the surface that is usable by the RF imaging device to determine the position of the RF imaging device relative to the surface. As with previous embodiments, the orientation of the RF imaging device relative to the surface may be determined based on at least one distance parameter obtained from a range sensor and at least one tilt parameter obtained from a tilt sensor that are operatively coupled to or incorporated in the RF imaging device.

With any of the above embodiments, the produced image may be a composite image that includes RF image data and optical image data selected based on the specified position relative to the surface.

With another embodiment, the RF imaging device may comprise (1) an RF sensor assembly that is configured to capture RF image data representing an RF image of a three-dimensional space behind an area of a surface; (2) an optical sensor that is configured to capture optical image data representing an optical image of the area of the surface; (3) a processor operatively coupled to the RF sensor assembly and the optical sensor, wherein the processor is configured to produce a composite image in which one or more portions of the optical image data are simultaneously viewable with one or more portions of the RF image data for the same area of the surface; and (4) an output configured to provide the composite image for display. The RF imaging device may further comprise a display screen, wherein the output provides the composite image to the display screen for display.

As discussed earlier in relation to FIG. 16, the display screen may be a primary display screen and the RF imaging device may further comprise a secondary display screen. With this embodiment, the processor may be further configured to produce an RF cross-sectional image of the space behind the area of the surface that is oriented at an angle with respect to the RF image represented by the RF image data in the composite image displayed by the primary display screen. In some cases, the secondary display screen may be physically oriented on the RF imaging device at an angle with respect to the primary display screen that approximates the angle between the RF cross-sectional image and the RF image in the composite image displayed by the primary display screen.

Figure 24:
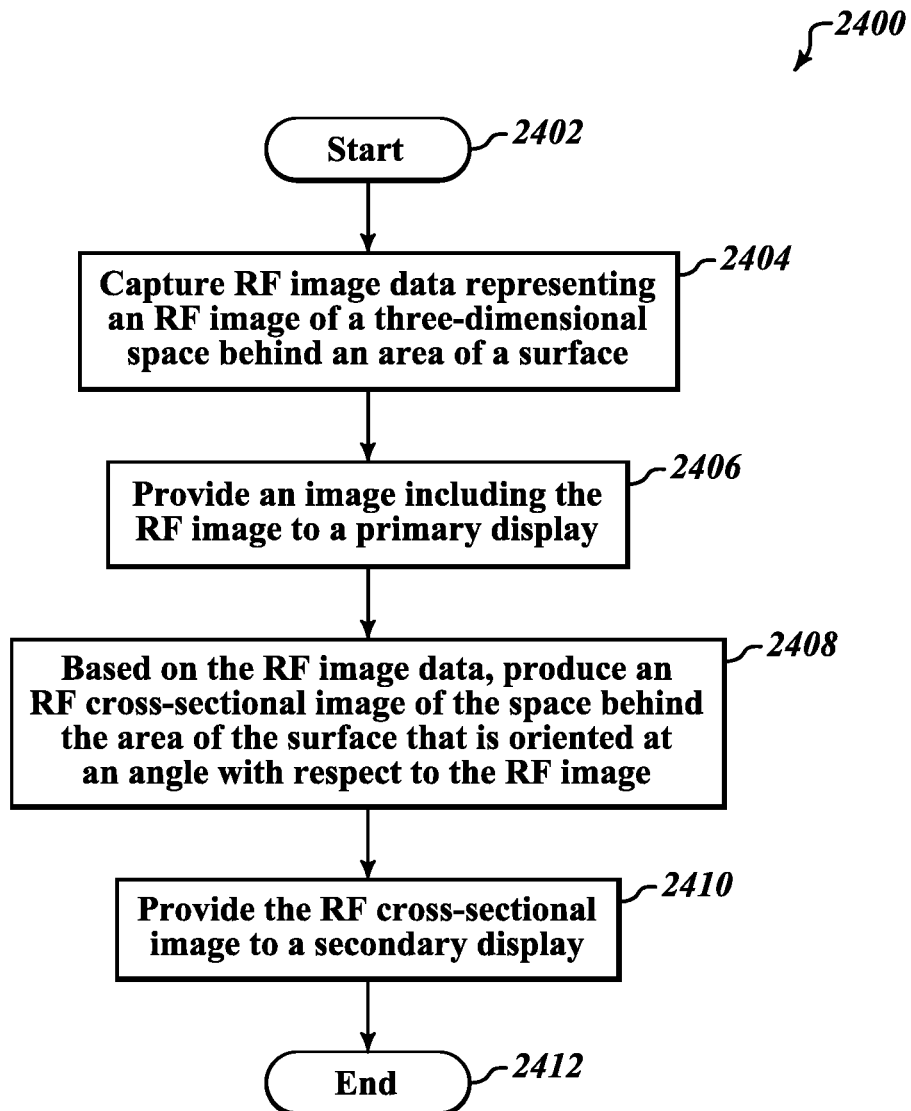

FIG. 24 shows a method 2400 that begins at a starting block 2402. In accordance with the method 2400, at block 2404, RF image data representing an RF image of a three-dimensional space behind an area of the surface is captured. At block 2406, an image including the RF image is provided to a primary display. At block 2408, based on the RF image data, an RF cross-sectional image of the space behind the area of the surface is produced. The RF cross-sectional image is oriented at an angle with respect to the RF image in the primary display. Thereafter, the RF cross-sectional image is provided to a secondary display, as indicated at block 2410. The method 2400 ends at block 2412.

The output may provide the composite image to a projector that projects the composite image for display. Alternatively or in addition, the output may provide the composite image to a device separate from the RF imaging device, wherein the separate device does not have RF sensors for imaging the space behind the area of the surface. The composite image may be provided to the separate device by wireless communication.

Figure 25:
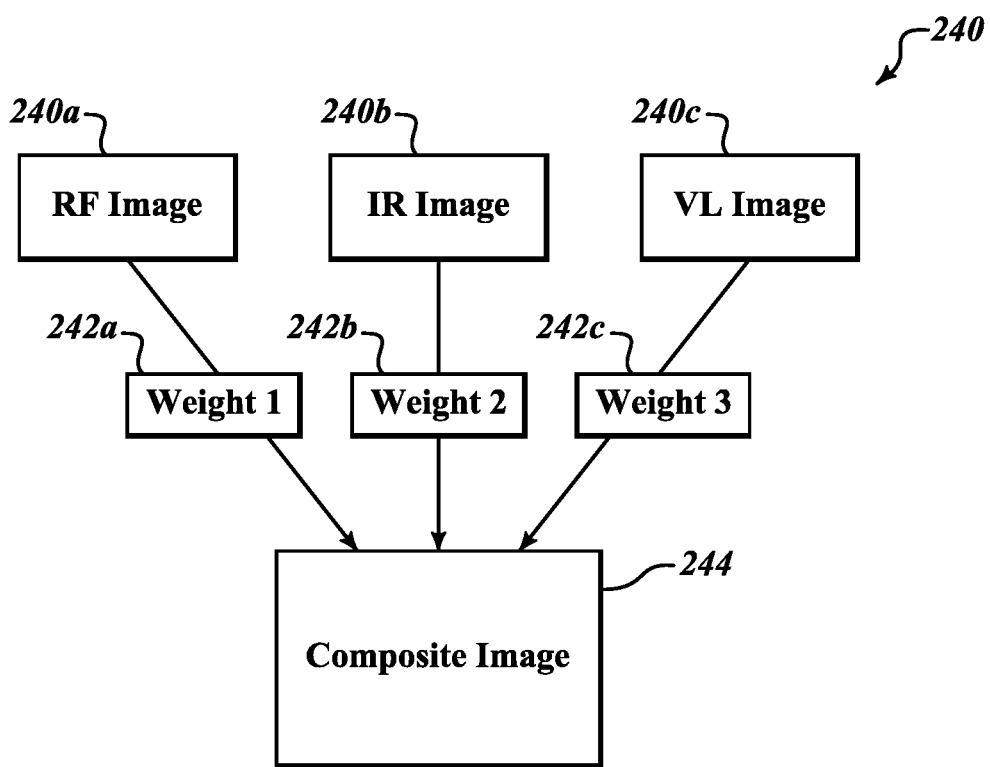
FIG. 25 shows an example of forming a composite image as a weighted combination of a plurality of images.

As previously described, the RF imaging device may produce a composite image formed by combining multiple images including an RF image of a space behind a surface. FIG. 25 shows an example of forming a composite image 244 as a weighted combination of a plurality of images 240a-c. The plurality of images 240 (singularly referred with reference to FIG. 25 as image 240) include an RF image 240a of objects behind a surface, an IR image 240b of the surface and a visible light image 240c of the surface. A contribution of each image 240 to the composite image 244 is dictated by a respective weight 242 associated with the image 240. A first weight 242a dictates the contribution of the RF image 240a, a second weight 242b dictates the contribution of the IR image 240b, and a third weight 242c dictates the contribution of the visible light image 240c.

A weight 242 may range from a minimum value to a maximum value, such as zero and one, respectively. In at least one case, if the weight 242 has the minimum value, the associated image 240 does not contribute to the composite image 244. Conversely, if the weight 242 has the maximum value, then the composite image 244 is made up entirely of the image 240 associated with the weight 242.

In at least one embodiment, the composite image 244 is a superposition of the plurality of images 240a-c in accordance with their respective plurality of weights 242a-c. The composite image 244 may, accordingly, show the RF image 240a of objects behind a surface superposed with the IR image 240b of the surface and/or the visible light image 240c of the surface.

In another embodiment, the composite image 244 is a superposition of one or more images 240a-c and also of additional images produced from one or more of the images 240a-c. These additional images may be, for example, produced from the images 240a-c using image processing techniques, in order to provide an improved visualization, e.g., to the user of the system, of details or features of the imagery that are important. One such additional image type that may be produced and incorporated into the composite image is a high frequency or edge-enhanced image. Another such image type that may be produced and incorporated into the composite image is an idealization of an image created by object-replacement. In this image type, objects within an image are identified, and replaced by, a graphical representation of the object stored in an image library, of the same size, shape, and orientation. These structure types to be replaced in the imagery might include pipes, wires, wood studs, etc. Other additional image types produced from images 240a-c are possible. As the composite image consists of weightings of the original images and/or images created from the images 240a-c, many weighted combinations are possible. The user of the device might be provided with an interface to adjust the weightings of the possible image types as desired.

Figure 26:
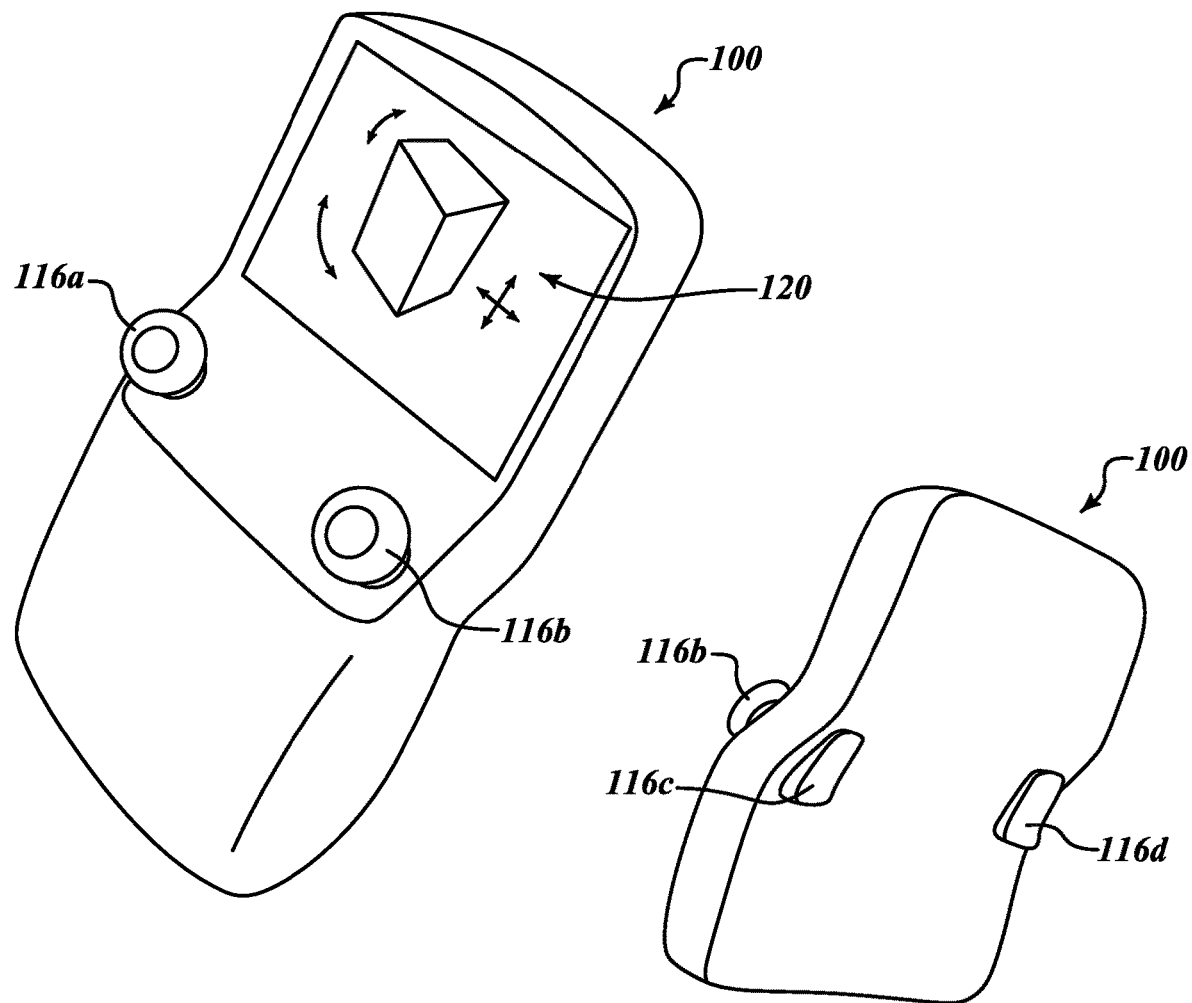
FIG. 26 shows front and rear perspective views of an RF imaging device in accordance with one embodiment.

FIG. 26 shows front and rear perspective views of an RF imaging device 100 in accordance with at least one embodiment. In particular, a plurality of input devices 116a-d (singularly referred to as input device 116) and a display 120 of the RF imaging device 100 are shown. First and second input devices 116a,b are joysticks and third and fourth input devices 116c,d are press buttons. Although joysticks and press buttons are shown, it is noted that an input device 116 may be of another type, such as a scroll wheel, keypad, or touchscreen, among others.

The display 120 receives data representing an image and displays the image. The image may be an RF image of objects behind a surface, an IR image of the surface, a visible light image, or a composite image. The RF image may be a 3D RF image and the composite image may have a 3D RF image component.

Users, such as building or construction contractors for example, may operate the plurality of input devices 116a-d to provide user inputs to manipulate the display of the image. For example, the first input device 116a may be used to provide a user input that is a pan command, the second input device 116b may be used to provide a user input that is a rotate command. Further, the third input device 116c may be used to provide a user input that is a zoom in command and the fourth input device 116d may be used to provide a user input that is a zoom out command.

If a pan command is input by a user, the point of view of the displayed image is translated linearly to the right or left, or up or down. If a rotate command is input by the user, a perspective of view of the image is rotated about an arc centered within the perspective of view. Further, if a zoom in command is input by the user an area of the image is enlarged, whereas if a zoom out command is input by the user, an area of the image is shrunk.

In response to receiving user input via an input device 116, the input device 116 outputs data representing the user input to a processor of the RF imaging device, such as the processor 102 described with reference to FIG. 1. The processor manipulates the displayed image to produce another image in accordance with the command. The other image may be a pan over of the displayed image or a rotation of the displayed image. Furthermore, if a zoom in command is input by the user, the other image may be an enlargement of the displayed image. If a zoom out command is input by the user, the displayed image may be shrunk to produce the other image. The processor manipulates the displayed image in accordance with the command to produce the other image. The processor outputs data representing the other image to the display.

Various types of input device 116a-d offer flexibility to a user of the RF imaging device 100 in inputting the commands to manipulate display of the image. For example, when the input device 116 is a joystick, an angle of actuation of the joystick dictates an angle of rotation of the displayed image. The angle of actuation of the joystick may correspond to an angle between a horizontal plane and the arc about which the displayed image is rotated.

Figure 27:
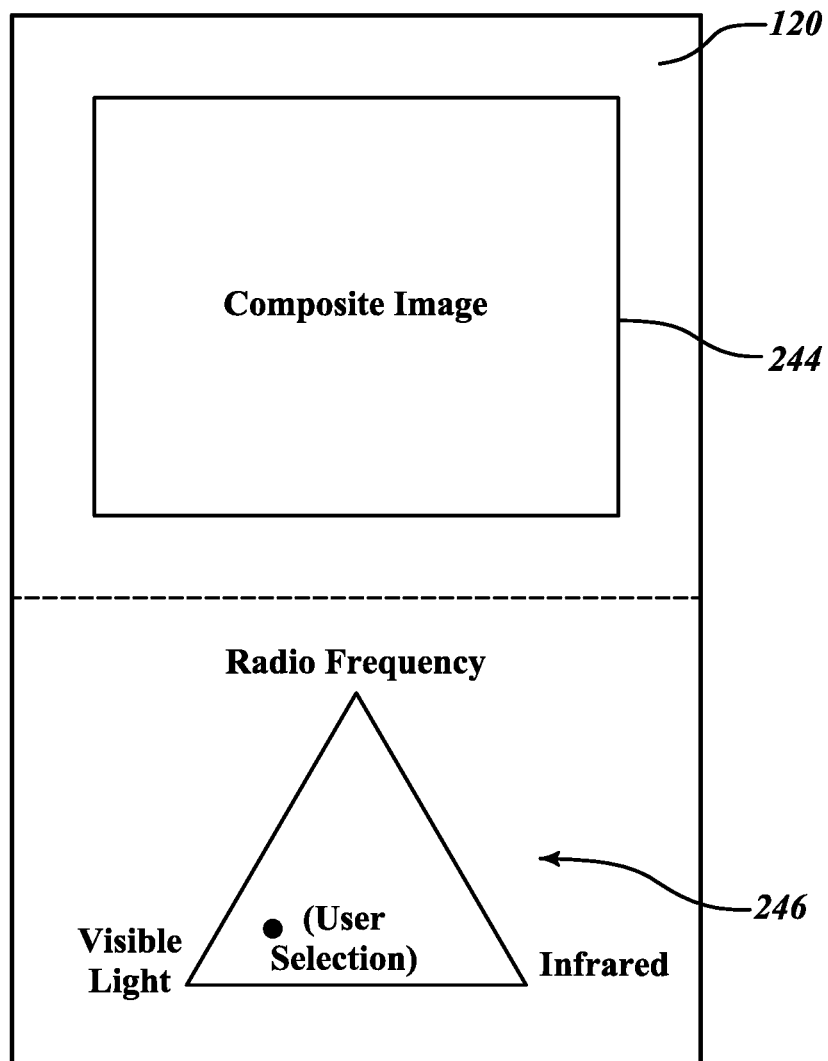
FIG. 27 shows a display of the RF imaging device in accordance with at least one embodiment.

FIG. 27 shows a display 120 of the RF imaging device 100 in accordance with at least one embodiment. The display 120 displays a composite image 244 and a user interface 246. As described herein, the composite image 244 is a weighted combination of a plurality of images, such as the images 240a-c described with reference to FIG. 25. The plurality of images are combined in accordance with a plurality of weights, such as the plurality of weights 242a-c, associated with the plurality of images, respectively.

The user interface may be used to indicate and adjust the plurality of weights. The user interface 246 is shown in this embodiment to be a triangle having three vertices that respectively correspond to the plurality of weights. The user interface also includes a user selection indicator disposed within the triangle. The position of the user selection indicator within the triangle simultaneously indicates the plurality of weights.

Each vertex of the triangle corresponds to an image that contributes or may potentially contribute to the composite image 244. The distance between the user selection indicator and the vertex is indicative of the weight assigned to the image. The distance may be inversely proportional to the weight such that if the user selection indicator is positioned on the vertex, the contribution of the respective image to composite image 244 is at a maximum and a contribution of remaining images is at a minimum.

In FIG. 27, the user selection indicator is shown closer to the vertex corresponding to the visible light image than vertices corresponding to the RF image or the IR image. Accordingly, a greater amount of contribution is made by the visible light image to the composite image 244 than either the RF image or the IR image. Further, because the user selection indicator is substantially equidistant to the vertices corresponding to the RF image and the IR image, the contribution of the RF image and the IR image to the composite image 244 is substantially the same. It is noted that if the user selection indicator was positioned in the center of the triangle (i.e., equidistant to the three vertices) then the contribution of the three images to the composite image 244 would be the same.

Although a triangle is shown in FIG. 27, it may be recognized that another geometrical shape may be used instead as part of the user interface 246. For example, if only two types of images (such as an RF image and an IR image) were available to be combined to form the composite image 244, the geometrical shape may be a line drawn between two end points that each correspond to an image. The position of the user selection indicator on the line may represent the contribution of both images to the composite image 244. Should four images be available to contribute to the composite image 244, the user interface 246 may use a square, for example, with each corner of the square corresponding to one of the images that contributes (or may contribute) to the composite image. A circle may be used to indicate the contribution of any number of images to the composite image, with nodes for each image being distributed, preferably equidistant, around the circumference of the circle and a user selection indicator being disposed within the circle.

The RF imaging device 100 may include an input device that is operable to receive a user input to change the plurality of weights. For example, the input device may be a joystick that, when actuated, permits the user to move or relocate the user selection indicator to another position within the displayed geometric image. The other position corresponds to different weights than those of the previous position. Relocation of the user selection indicator to the other position results in changing the plurality of weights used to combine the plurality of images. The displayed composite image 244 will be updated to reflect the changed weights. In some embodiments, the RF imaging device may be configured to automatically update the displayed composite image at regular intervals while the user selection indicator is being moved so that the user receives immediate feedback by viewing the changes to the composite image 244 while moving the user selection indicator.

Upon receiving the user input, the input device outputs data representing the user input to the processor. The processor receives the data and generates another composite image based on the changed weights. To generate the other composite image, the processor combines the plurality of images in accordance with the changed weights. The processor outputs data representing the other composite image to the display, and the display displays the other composite image.

The user interface may also specify whether the RF image (for example, used in generating the composite image 244 is a 3D RF image or a 2D RF image). The input device may permit the user to select between use of a 3D RF image or a 2D RF image to generate the composite image 244.

As mentioned earlier herein, in RF imaging, different types of materials reflect RF waves differently. For example, an RF wave that impinges on wood is reflected differently by the wood than by metal. The differences in the reflection of the RF wave are distinguishable and the manner in which a material reflects an RF wave amounts to an RF signature of the material. The RF signature of one material has characteristics and attributes that differentiate it from RF signatures of other materials.

As described herein, in walled structures such as homes and offices, living or working spaces are separated by paneling, such as dry wall or lath and plaster paneling, from electrical wiring, plumbing systems and structural objects, among others, that are disposed behind paneling surfaces. When performing RF imaging on a space behind a surface, an RF wave is emitted and one or more reflections of the RF wave from objects disposed behind the surface are sensed. The material composition of the sensed objects may be identified based on determining that the RF signature of the material is present in the reflection of the RF wave.

The respective RF signatures (or characteristics or attributes thereof) of various types of materials may be known to the RF imagining device 100. For example, the RF signatures may be stored in the memory 114 and may be accessible by the processor 102. The processor 102 of the RF imaging device 100 may receive data representing a reflection of an RF wave from one or more objects disposed behind a surface. The data representing the reflection of the RF wave may be provided by the RF sensor assembly 122. The processor 102 may then evaluate the data representing the reflection of the RF wave to determine whether a signature of the known signatures is present in the data.

If the RF signature of a type of material is determined to be present in the data representing the reflection of the RF wave, the processor 102 may output data indicating detection of the type of material to an output device, such as the output device 118. The output device 118, which may for example be a marker or a label maker, among others, may produce a physical output that is placeable on the surface. The physical output may indicate the detected type of material. For example, the physical output may indicate detection of wood, PVC, aluminum or copper, among others. The physical output may be outputted at a position where the RF imaging device 100 or the processor 102 thereof has detected the RF signature. The physical output indicates to personnel presence of the material at the position behind the surface. Placing (or outputting) the physical output at the position facilitates pinpoint cutting or excavating of the surface, for example, to access the object having the detected type of material.

Figure 28:
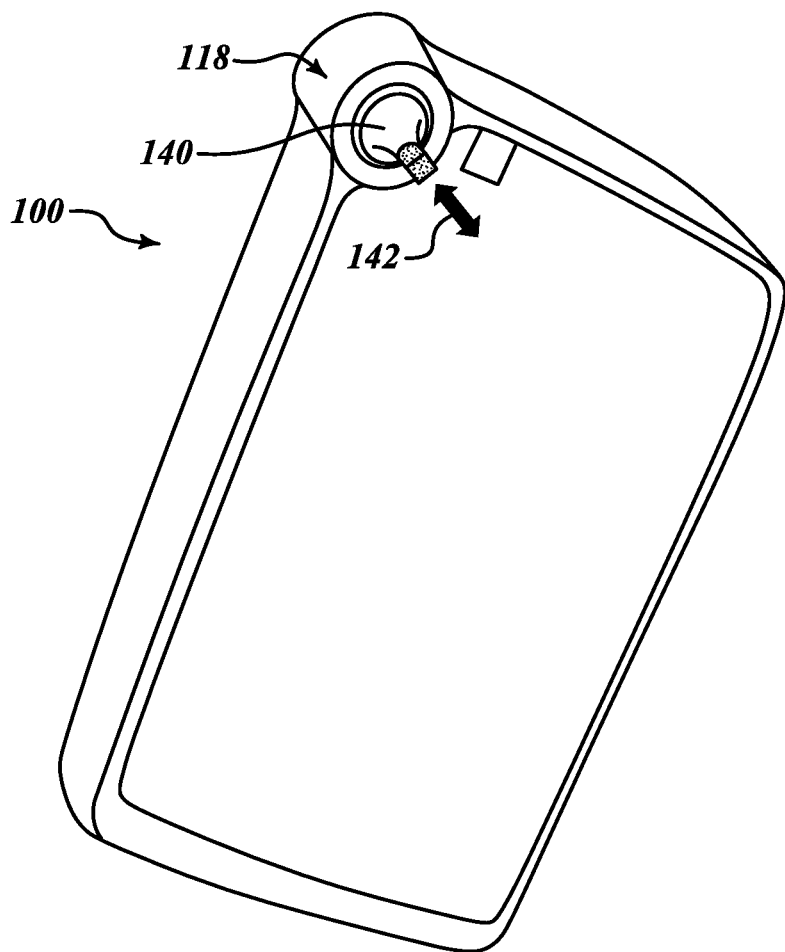
FIG. 28 shows a perspective view of an RF imaging device having an ink marker as an output device.

FIG. 28 shows a perspective view of an RF imaging device 100 having an ink marker 140 as an output device 118. The ink marker may be configured to translate in an axial direction as indicated by the arrow 142 to mark a surface with a plurality of colors. Each color may respectively correspond to a type of material of a plurality of types of material that the RF imaging device 100 may detect. The materials may be color-coded and each type of material may be assigned a different color than other types of materials. Alternatively, the ink marker 140 may be configured to output, or stamp, a certain symbol, such as a letter, on the surface for each type of detected material. In operation, the RF imaging device 100 may be positioned near the surface such that the ink marker may mark the surface upon detection of a type of material.

In yet other embodiments, the ink marker 140 may be configured to mark the surface with a "blacklight" ink (which generally is difficult to see except under a UV/blacklight source) and/or a color fading ink that does not leave any noticeable trace after a period of time. The marking indicates the location of an object behind the surface, and potentially the type of material of the object.

The ink marker 140 marks the surface at the position where the RF sensor assembly 122 sensed the RF wave reflection in which the RF signature of the type of material was detected. The ink marker 140 may, in some embodiments, be positioned centrally in relation to a broadside of the RF sensor assembly 122. Accordingly, the surface may be marked at the position where the RF wave having the RF signature was in fact reflected.

Alternatively, the ink marker 140 may be positioned away from the RF sensor assembly 122 or, as shown in FIG. 28, at an edge of the RF imaging device 100. The ink marker may be positioned away from the RF sensor assembly 122 so that it does not interfere with the receiving capabilities of the RF sensor assembly 122. In this case, the RF imaging device 100 may be configured to mark the surface after the RF imaging device 100 has been displaced by a known distance between a center of the RF sensor assembly 122 and the ink marker.

In some embodiments, the ink marker 140 may be spring loaded or otherwise actuated by the RF imaging device to mark the surface. In other embodiments, the ink marker may be guided by the RF imaging device but manually actuated by a user of the device to mark the surface.

Figure 29:
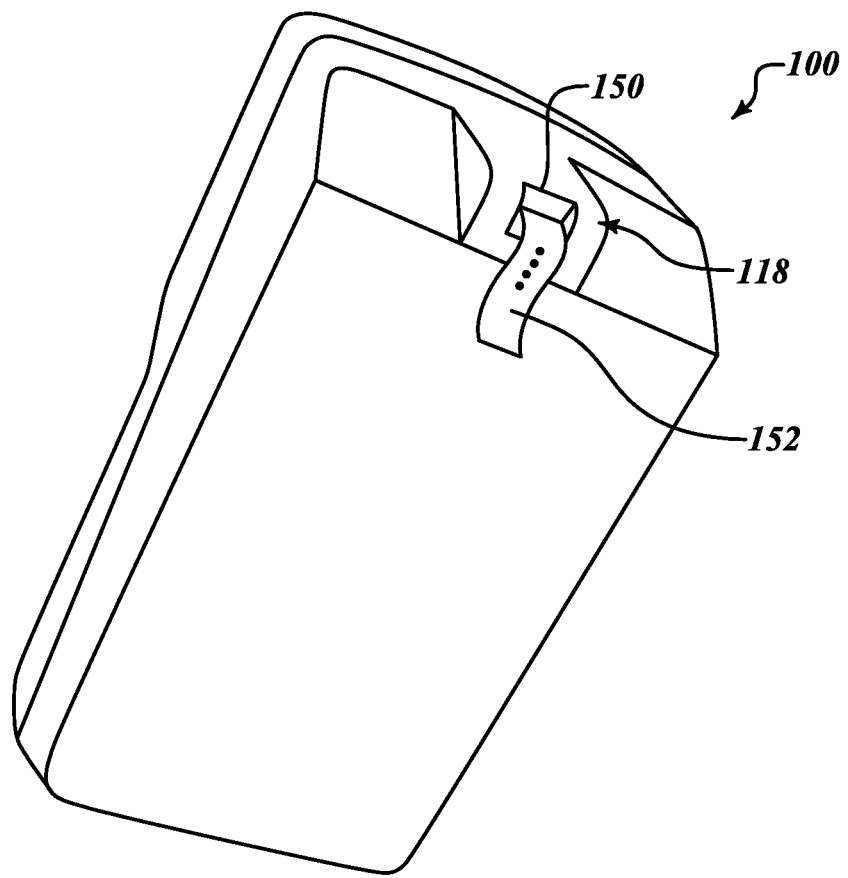
FIG. 29 shows a perspective view of an RF imaging device having a label maker as an output device.

FIG. 29 shows a perspective view of an RF imaging device 100 having a label maker 150 as an output device 118. Similar to the ink marker 140, the label maker 150 may produce a label 152 specifying the type of material that is detected. The type of material may be typed on the label 152 or a symbol or color representing the type of material may be present on the label. The label 152 may have an adhesive that facilitates removably affixing the label to the surface at the position where the RF signature corresponding to the type of material was detected.

Figure 30:
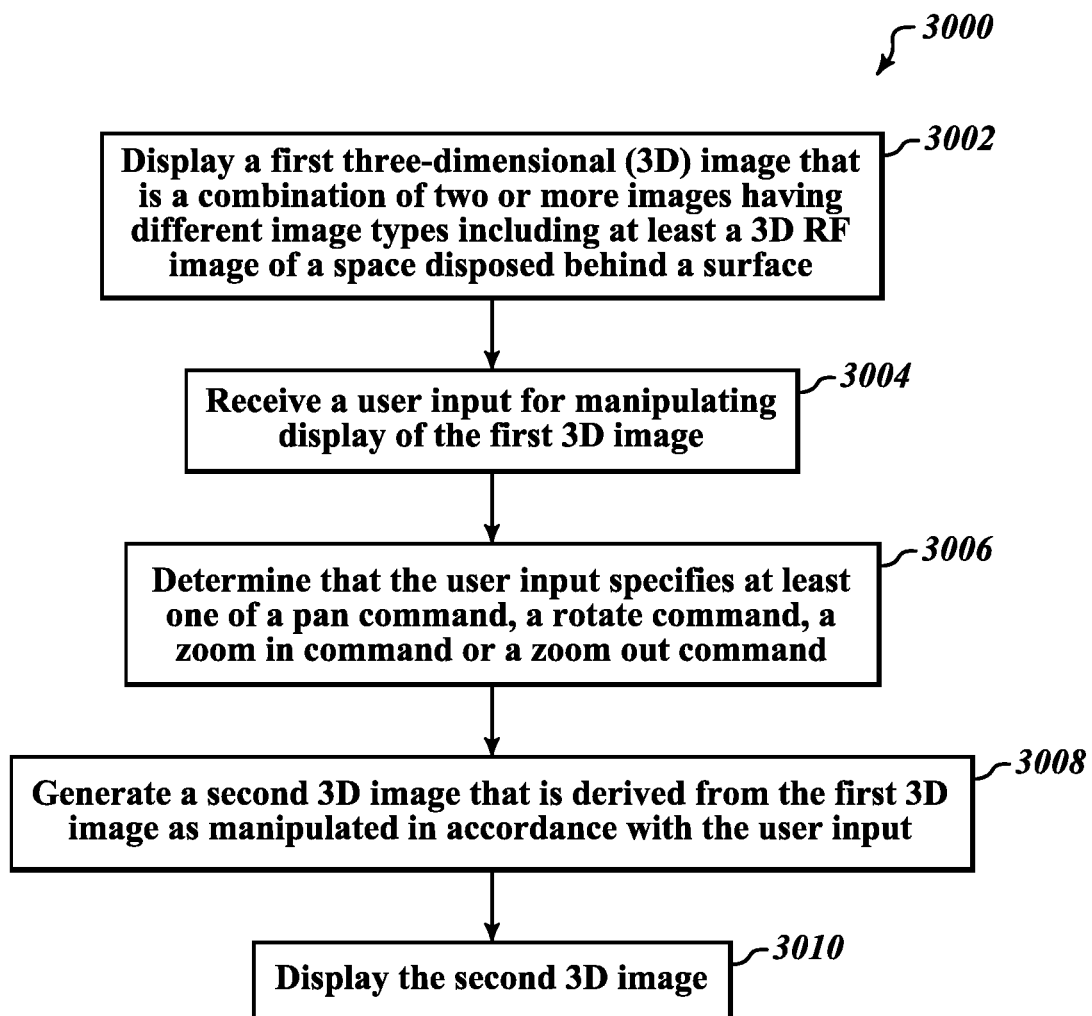
FIG. 30 shows a flow diagram of a method for manipulating a 3D image displayed by the RF imaging device.

FIG. 30 shows a flow diagram of a method for manipulating a 3D image displayed by the RF imaging device 100. In the method 3000, a display of the RF imaging device 100, such as the display 120 described with reference to FIG. 1, displays, at block 3002, a first 3D image that is a combination of two or more images having different image types including at least a 3D RF image of a space disposed behind a surface. The other image types may include an IR image or a visible light image.

An input device of the RF imaging device 100, such as the input device 116 described with reference to FIG. 1, receives a user input for manipulating a display of the first 3D image at block 3004. The input device may, for example, be a joystick or a press button, among others. The input device outputs data representing the user input to a processor, such as the processor 102 described with reference to FIG. 1. The processor, at block 3006, determines that the user input specifies at least one of a pan command, a rotate command, a zoom in command or a zoom out command. The processor, at block 3008, generates a second 3D image that is derived from the first 3D image as manipulated in accordance with the user input. The processor may output data representing the second 3D image to the display. The display, at block 3010, displays the second 3D image.

Figure 31:
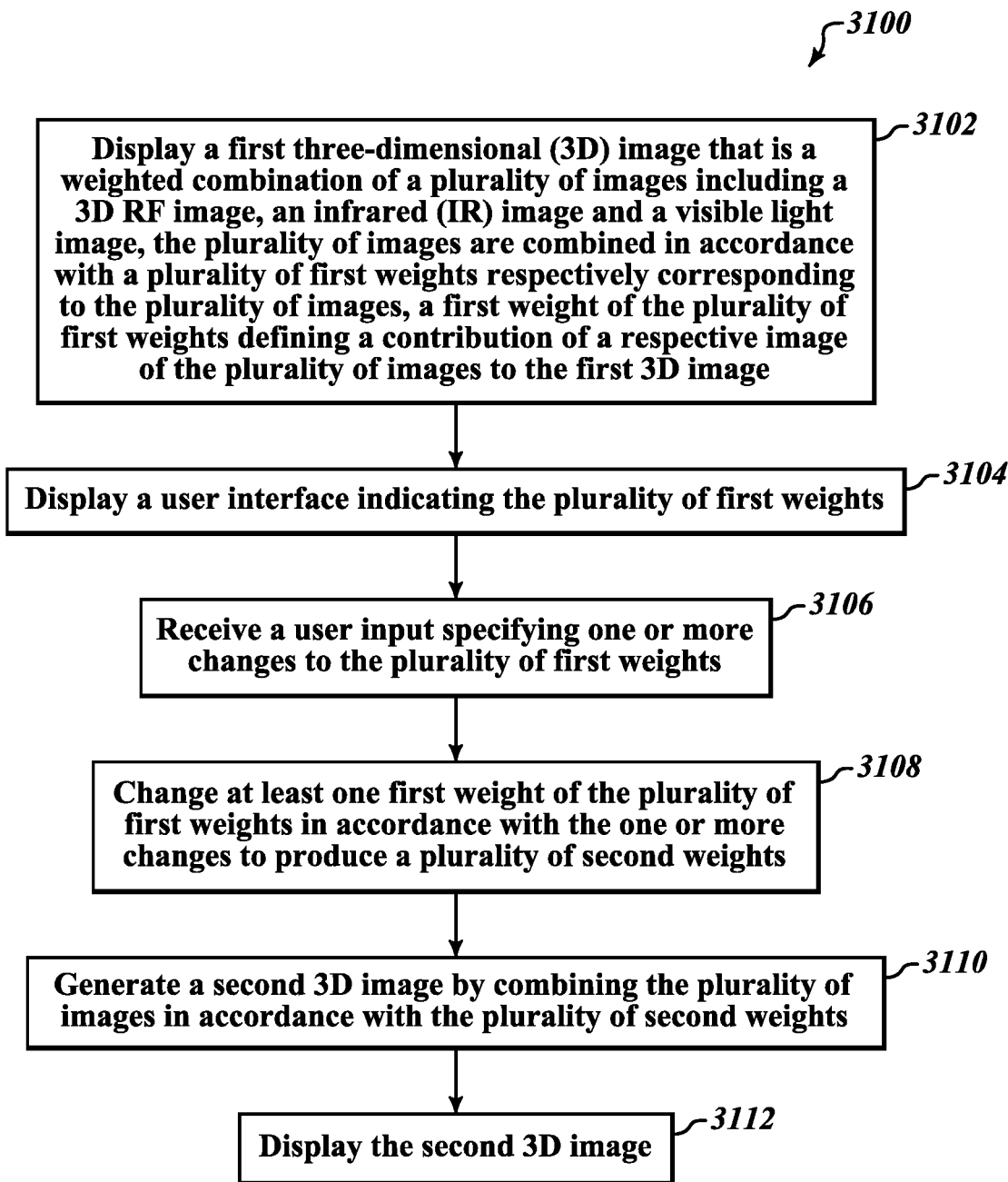
FIG. 31 shows a flow diagram of a method for presenting a user interface on a display of the RF imaging device.

FIG. 31 shows a flow diagram of a method for presenting a user interface on a display of the RF imaging device 100. In the method 3100, a display, such as the display 120 described with reference to FIG. 1, displays, at block 3102, a first 3D image that is a weighted combination of a plurality of images. The plurality of images may include, in this example, a 3D RF image, an IR image and a visible light image. The plurality of images are combined in accordance with a plurality of first weights respectively corresponding to the plurality of images.

At block 3104, the display displays a user interface indicating the plurality of first weights. The user interface may have a geometrical shape having a plurality of vertices and a user selection indicator. Each vertex of the plurality of vertices may respectively correspond to an image of the plurality of images and a distance between the user selection indicator and the vertex represents (or inversely represents) the weight of the image.

The RF imaging device 100 may include an input device, such as the input device 116 described with reference to FIG. 1. Examples of the input device include a joystick or scroll wheel, among others. The input device, at block 3106, receives a user input specifying one or more changes to the plurality of first weights. The user input may be provided by user actuation of the input device to relocate the user selection indicator to another position within the geometrical shape. The input device may output data representing the user input to a processor, such as the processor 102 described with reference to FIG. 1.

At block 3108, the processor changes at least one first weight of the plurality of first weights in accordance with the one or more changes to produce a plurality of second weights. The processor, at block 3110, generates a second 3D image by combining the plurality of images in accordance with the plurality of second weights. The processor may output data representing the second 3D image to the display. In turn, the display, at block 3112, displays the second 3D image. The location of the user selection indicator within the geometrical display indicates the plurality of second weights associated with the second 3D image.

Figure 32:
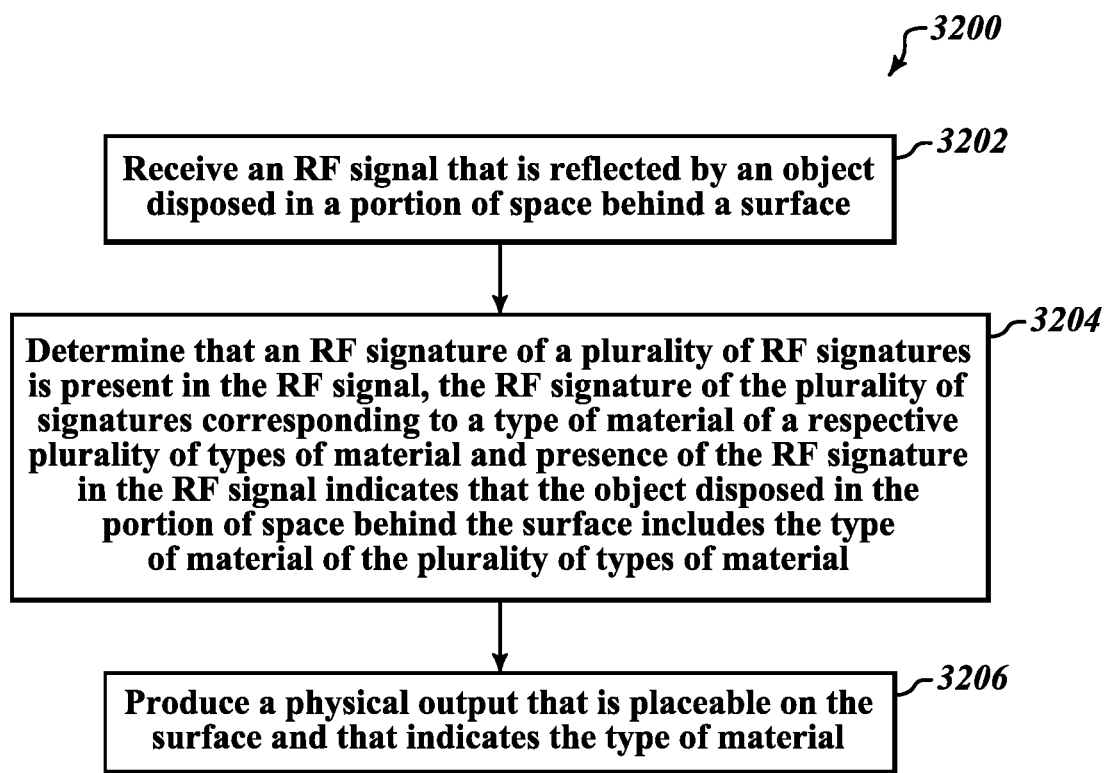
FIG. 32 shows a flow diagram of a method for producing a physical output for marking a surface by the RF imaging device.

FIG. 32 shows a flow diagram of a method for producing a physical output for marking a surface by the RF imaging device 100. In the method 3200, an RF sensor assembly, such as the RF sensor assembly 122 described with reference to FIG. 1 herein, receives, at block 3202, an RF signal that is reflected by an object disposed in a portion of space behind a surface. The RF sensor assembly may output data representing the RF signal to a processor, such as the processor 102 described with reference to FIG. 1.

At block 3204, the processor determines that an RF signature of a plurality of RF signatures is present in the RF signal. The RF signature of the plurality of signatures corresponds to a type of material of a respective plurality of types of material. Presence of the RF signature in the RF signal indicates that the object disposed in the portion of space behind the surface includes the type of material of the plurality of types of material. The plurality of RF signatures (or characteristics or attributes thereof) may be stored in a memory, such as the memory 114 described with reference to FIG. 1. The plurality of RF signatures may be accessible by the processor for determining whether an RF signature of the plurality of RF signatures is present in RF signals.

The processor outputs data identifying the type of material to an output device, such as the output device 118 described with reference to FIG. 1. The output device in this regard may be a marker or a label maker, among others. The output device then produces, at block 3206, a physical output that is placeable on the surface and indicates the type of material. The physical output may be a mark made with pen or marker, among others, or a label that is affixable to the surface. The physical output may be placed on the surface at a position where the RF signal was reflected.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A radio frequency (RF) imaging device comprising:
a position sensor configured to determine a position of the RF imaging device relative to a surface based on a plurality of signals respectively emitted by a plurality of position markers external to the RF imaging device and positioned at known positions on the surface, a position marker of the plurality of position markers including a transmitter configured to transmit a signal of the plurality of signals to the position sensor;
an RF sensor assembly configured to capture RF image data representing an RF image of a portion of a space behind the surface at the determined position;
an optical sensor configured to capture optical image data representing an optical image of the surface at the determined position;
an input device configured to receive data representative of a first weight associated with the RF image and a second weight associated with the optical image; and
a processor configured to produce a composite image in which at least one or more portions of the RF image and one or more portions of the optical image that correspond to the same position relative to the surface are simultaneously viewable by combining the one or more portions of the RF image and the one or more portions of the optical image such that a contribution by the one or more portions of the RF image and a contribution by the one or more portions of the optical image to the composite image are in accordance with the first weight and the second weight, respectively.

2. The RF imaging device of claim 1, further comprising a memory in which the RF image data and the optical image data are stored in association with position data derived from the determined position of the RF imaging device.

3. The RF imaging device of claim 1, wherein the RF sensor assembly captures a plurality of RF images at a respective plurality of positions relative to the surface, each RF image being an RF image of a portion of the space behind the surface at the respective plurality of positions, wherein the optical sensor captures a plurality of optical images of the surface at the respective plurality of positions, and
wherein the processor is configured to:
assemble (1) a panoramic RF image of the space behind the surface based on the plurality of RF images, and (2) a panoramic optical image of the surface based on the plurality of optical images; and
produce a composite image in which at least one or more portions of the panoramic RF image and one or more portions of the panoramic optical image that correspond to the same position relative to the surface are simultaneously viewable.

4. The RF imaging device of claim 3, wherein the processor is configured to assemble the panoramic RF image by collating the plurality of RF images of the space behind the surface at the respective plurality of positions, and to assemble the panoramic optical image by collating the plurality of optical images of the surface at the respective plurality of positions.

5. The RF imaging device of claim 4, wherein collating the plurality of RF images includes identifying RF image data in the plurality of RF images at different positions relative to the surface and assembling the RF image data at each position to form the panoramic RF image, and
wherein collating the plurality of optical images includes identifying optical image data in the plurality of optical images at different positions relative to the surface and assembling the optical image data at each position to form the panoramic optical image.

6. The RF imaging device of claim 5, further comprising a memory in which (1) the RF image data forming the panoramic RF image is stored in association with position data indicating the respective positions of the RF image data relative to the surface, and (2) the optical image data forming the panoramic optical image is stored in association with position data indicating the respective positions of the optical image data relative to the surface.

7. The RF imaging device of claim 1, further comprising a tilt sensor that determines an orientation of the RF imaging device relative to the surface when the RF image data and the optical image data are captured, wherein the orientation specifies a rotation of the respective RF image and optical image about an axis in relation to the surface, and wherein the RF image data and the optical image data are adjusted based on the specified rotation so that the RF image and the optical image have a common orientation relative to the surface.

8. The RF imaging device of claim 1, wherein the RF image data representing the RF image at the determined position and the optical image data representing the optical image at the determined position are captured at different times.

9. The RF imaging device of claim 8, wherein the RF imaging device is moved to a different position relative to the surface between capturing the RF image data representing the RF image and capturing the optical image data representing the optical image.

10. A radio frequency (RF) imaging device, comprising:
a position sensor configured to capture signal data representing a plurality of signals respectively emitted by a plurality of position markers external to the RF imaging device and positioned at known positions on a surface, a position marker of the plurality of position markers including a transmitter configured to transmit a signal of the plurality of signals to the position sensor;

an optical sensor configured to capture optical image data representing an optical image of the surface;

an input device configured to receive data representative of a first weight associated with the optical image data and a second weight associated with an RF image data; and a processor operatively coupled to the position sensor and the optical sensor, wherein the processor is configured to:

receive the signal data representing the plurality of signals;

determine a position of the position sensor relative to the surface based on the known positions of the position markers and analysis of the signal data;

associate the optical image data with position data derived from the determined position of the position sensor; and produce a composite image in which one or more portions of the optical image data are simultaneously viewable with the RF image data representing an RF image of a space behind the surface at the same position relative to the surface as the optical image data, based on the position data associated with the one or more portions of the optical image data, producing the composite image including combining the one or more portions of the optical image data and the RF image data such that a contribution by the one or more portions of the optical image data and a contribution by the RF image data to the composite image are in accordance with the first weight and the second weight, respectively.

11. The RF imaging device of claim 10, further comprising a memory in which the optical image data and the RF image data are stored together in association with the position data derived from the determined position of the position sensor.

12. The RF imaging device of claim 10, further comprising a communication interface configured to transmit the composite image to a receiving device.

13. The RF imaging device of claim 10, wherein the transmitter of the position marker of the plurality of position markers is an active transmitter and is configured to transmit a signal of the plurality of signals to the position sensor, and wherein the position marker has a power source.

14. The RF imaging device of claim 10, wherein the transmitter of the position marker of the plurality of position markers is a passive transmitter that is induced to transmit a signal of the plurality of signals in response to receiving an activating signal.

15. The RF imaging device of claim 10, wherein the position of the position sensor relative to the surface is determined based on the known positions of the position markers and triangulation of the signal data.

16. The RF imaging device of claim 10, wherein the position of the position sensor relative to the surface is determined based on the known positions of the position markers and a determined time-of-flight for each of the plurality of signals transmitted from the respective position markers.

17. The RF imaging device of claim 10, wherein the optical sensor captures optical image data representing a plurality of optical images of the surface at a respective plurality of positions, and wherein the processor is further configured to:

assemble a panoramic optical image of the surface based on the optical image data representing the plurality of optical images, wherein the optical image data in the panoramic optical image is associated with position data derived from determined positions of the position sensor corresponding to when the optical image data representing the plurality of optical images was captured; and produce a composite image in which at least one or more portions of the optical image data in the panoramic optical image are simultaneously viewable with RF image data representing the RF image of the space behind the surface captured at the same position as the optical image data in the panoramic optical image, based on the position data associated with the one or more portions of the optical image data.

18. The RF imaging device of claim 10, wherein the RF image data representing an RF image of a space behind the surface represents a three-dimensional (3D) RF image.

19. A radio frequency (RF) imaging device, comprising:

a position sensor configured to capture signal data representing a plurality of signals respectively emitted by a plurality of position markers external to the RF imaging device and positioned at known positions on a surface, a position marker of the plurality of position markers including a transmitter configured to transmit a signal of the plurality of signals to the position sensor;

an optical sensor configured to capture data representing an optical image of the surface;

an input device configured to receive data representative of a first weight associated with the data representing the optical image and a second weight associated with data representing an RF image; and a processor operatively coupled to the position sensor and the optical sensor and configured to:

determine a position of the position sensor relative to the surface based on the known positions of the position markers and analysis of the signal data;

receive the signal data representing the plurality of signals;

determine, based on the signal data, a reference position for the RF imaging device;

associate the data representing the optical image of the surface with position data derived from the determined reference position; and produce a composite image in which one or more portions of the data representing the optical image are simultaneously viewable with the data representing the RF image of a space behind the surface at the same position as the one or more portions of the data representing the optical image, based on the position data associated with the one or more portions of the data representing the optical image, producing the composite image including combining the one or more portions of the data representing the optical image and the data representing the RF image such that a contribution by the one or more portions of the data representing the optical image and a contribution by the data representing the RF image to the composite image are in accordance with the first weight and the second weight, respectively.

20. The RF imaging device of claim 19, wherein the RF imaging device further comprises a displacement sensor configured to detect a displacement of the RF imaging device relative to the reference position and to output data representing the displacement, wherein the optical sensor is configured to capture data representing a subsequent optical image of the surface after the displacement of the RF imaging device has occurred; and wherein the processor is configured to:
receive the data representing the displacement;
determine a subsequent position of the RF imaging device based on the data representing the displacement and the reference position; and
associate the data representing the subsequent optical image with position data derived from the determined subsequent position of the RF imaging device.

21. The RF imaging device of claim 20, wherein the processor is further configured to:
assemble a panoramic optical image of the surface based on the data representing the optical image at the reference position and each subsequent position of the RF imaging device, wherein the data in the panoramic optical image is associated with position data derived from the reference position or a subsequent position of the RF imaging device corresponding to when the data representing the optical image or the subsequent optical image was captured; and produce a composite image in which at least one or more portions of the data in the panoramic optical image are simultaneously viewable with RF image data representing the 3D RF image of the space behind the surface at the same position as the data in the panoramic optical image, based on the position data associated with the one or more portions of the data in the panoramic optical image.

22. The RF imaging device of claim 19, wherein the data representing an RF image of a space behind the surface represents a three-dimensional (3D) RF image.

* * * * *